(12) United States Patent
Alajbegovic et al.

(10) Patent No.: US 12,070,588 B2
(45) Date of Patent: Aug. 27, 2024

(54) INJECTOR AND INJECTION METHOD THEREFOR

(71) Applicant: InocuJect Corp., Ottawa (CA)

(72) Inventors: Ales Alajbegovic, Ann Arbor, MI (US); Edward Tate, Grand Blanc, MI (US); Norman Viner, Squamish (CA); Maddison Albert, Hancock, MA (US); John Edward Campbell, Hazel Park, MI (US); Gary P. Kobinger, Galveston, TX (US); Julian Billie Stoller, Montpelier, VT (US)

(73) Assignee: InocuJect Corp., Ottawa (CA)

(*) Notice: Subject to any disclaimer, the term of this patent is extended or adjusted under 35 U.S.C. 154(b) by 0 days.

(21) Appl. No.: 18/242,899

(22) Filed: Sep. 6, 2023

(65) Prior Publication Data
US 2024/0075215 A1 Mar. 7, 2024

Related U.S. Application Data

(60) Provisional application No. 63/404,261, filed on Sep. 7, 2022.

(51) Int. Cl.
*A61M 5/315* (2006.01)
*A61M 5/32* (2006.01)

(52) U.S. Cl.
CPC ...... *A61M 5/31576* (2013.01); *A61M 5/3295* (2013.01)

(58) Field of Classification Search
CPC ............. A61M 5/3295; A61M 5/3297; A61M 5/3298; A61M 5/155; A61M 5/31576; A61M 37/0015; A61M 2037/0023; A61M 2037/003; A61M 2037/0038; A61M 2037/0046; A61M 2037/0061; A61M 2037/0076; A61M 2037/0084;
(Continued)

(56) References Cited

U.S. PATENT DOCUMENTS

| | | |
|---|---|---|
| 2005/0165358 A1 | 7/2005 | Yeshurun et al. |
| 2014/0128818 A1 | 5/2014 | Ogura et al. |

(Continued)

FOREIGN PATENT DOCUMENTS

| | | |
|---|---|---|
| CA | 3009189 A1 | 7/2017 |
| WO | WO-2020061679 A1 | 4/2020 |

*Primary Examiner* — Robert J Utama
*Assistant Examiner* — Leah J Swanson
(74) *Attorney, Agent, or Firm* — Teitelbaum & Bouevitch; Neil Teitelbaum

(57) ABSTRACT

An injector is disclosed for injecting an injectable substance into at least one of the epidermal tissue and the dermal tissue of a subject. The injector includes an outer housing and a control member disposed within the outer housing. A needle head, which is configured to support a plurality of needles, is operatively coupled to the control member. First means are provided in communication with the control member and are configured to be driven by the control member for converting a movement of the control member into a movement of the needle head along an injection direction and toward an injecting position of the needle head. Second means are configured to move the needle head in a direction having a component that is normal to the injection direction and absent movement of the outer housing relative to the skin of the subject.

17 Claims, 59 Drawing Sheets

(58) Field of Classification Search
CPC ...... A61M 2202/30; A61M 2005/1585; A61M 2005/342; A61M 2005/3289; A61M 2205/10; A61M 2205/103; A61M 2205/105; A61M 5/2053; A61B 17/205; A61B 17/20; A61D 1/02; A61D 1/025
See application file for complete search history.

(56) References Cited

U.S. PATENT DOCUMENTS

| | | | |
|---|---|---|---|
| 2014/0343481 A1* | 11/2014 | Ignon | A61M 5/3298 604/21 |
| 2019/0009084 A1* | 1/2019 | Stadelmann | A61N 1/327 |
| 2019/0351205 A1 | 11/2019 | Ford et al. | |
| 2022/0280385 A1* | 9/2022 | Converse | A61M 5/2046 |
| 2023/0211139 A1* | 7/2023 | Niven | A61M 37/0076 606/186 |

* cited by examiner

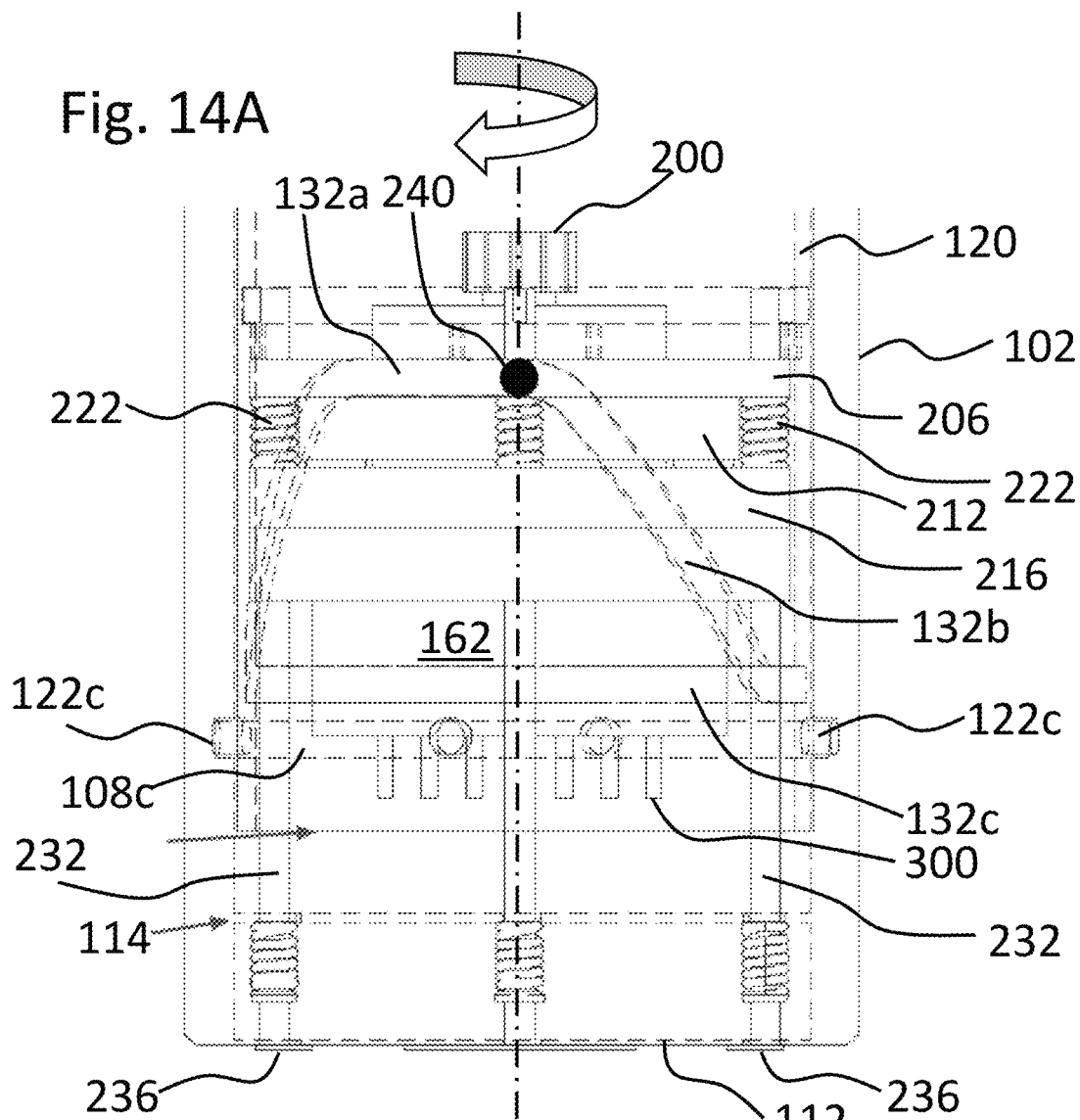
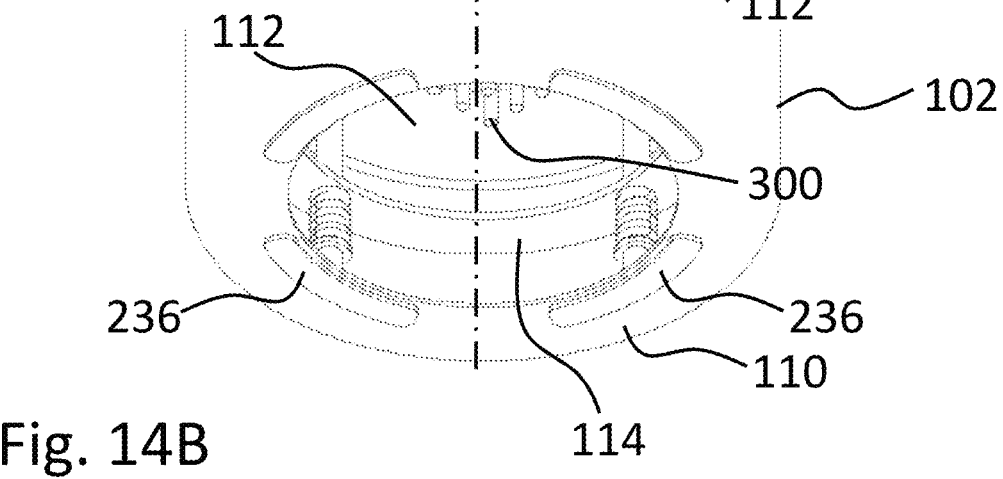
Fig. 14A
Fig. 14B

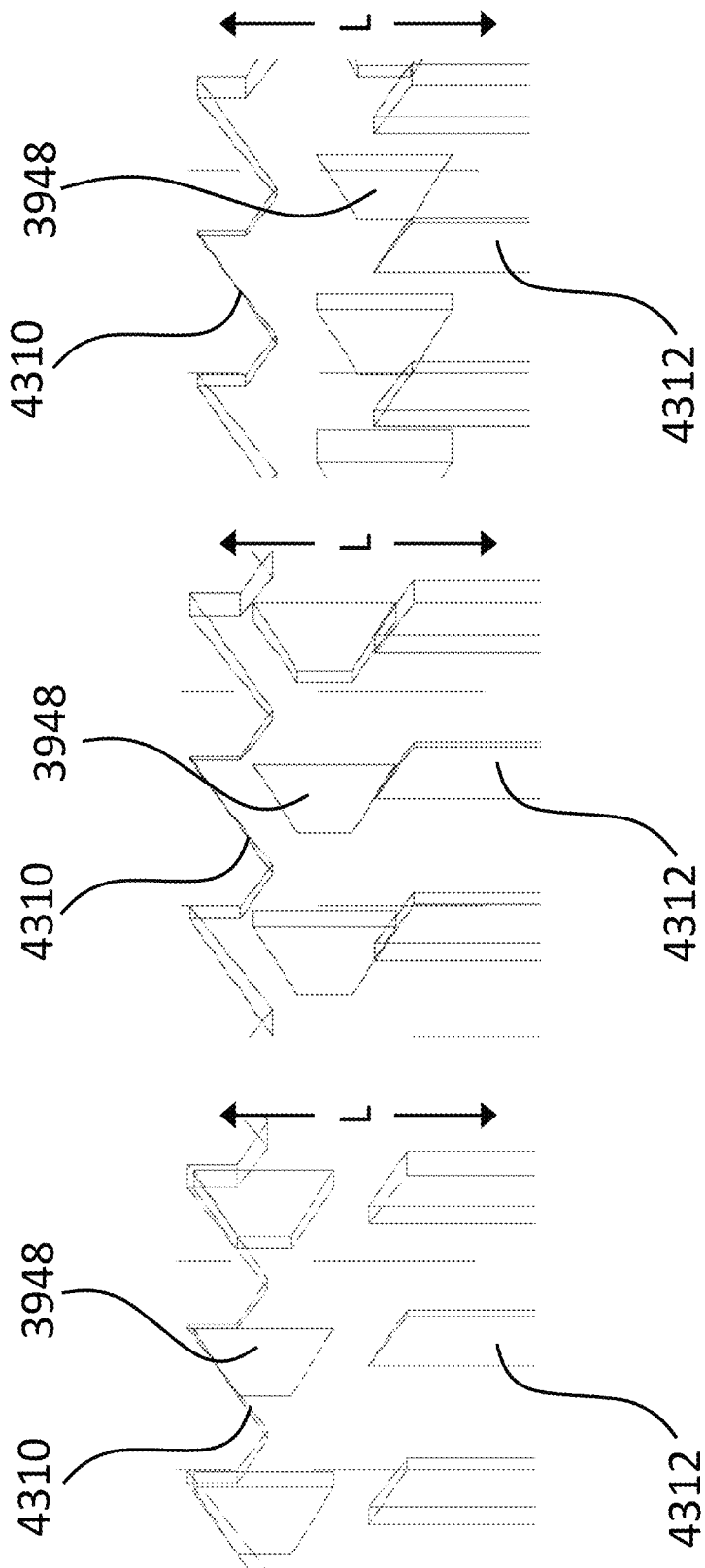

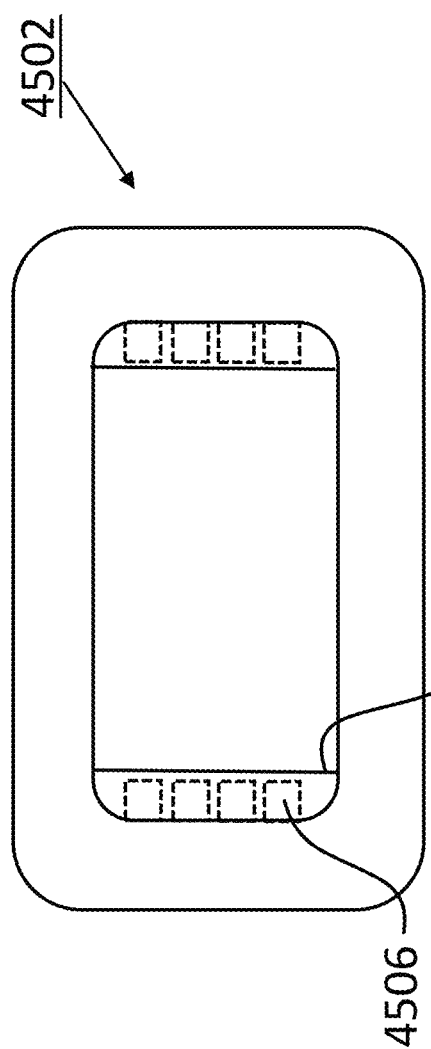
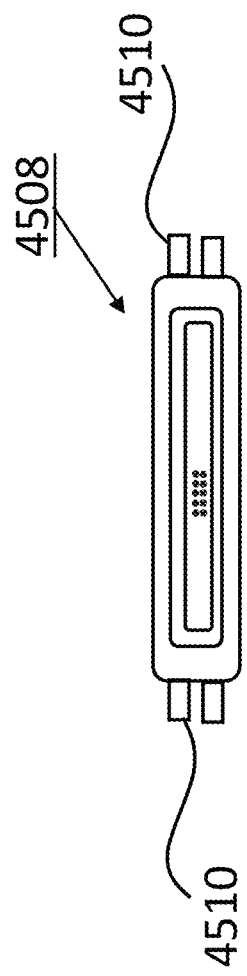
Fig. 45G
Fig. 45H

INJECTOR AND INJECTION METHOD THEREFOR

REFERENCE TO RELATED APPLICATION

This application claims the benefit of U.S. Provisional Patent Application No. 63/404,261 filed on Sep. 7, 2022, the entire contents of which is incorporated herein by reference.

FIELD

This disclosure relates to a device and method for administering injections to mammalian subjects, and more particularly to an injector and injection method for injecting a substance into the epidermal/dermal tissue of mammalian subjects.

BACKGROUND

Vaccines are a crucial defence in the fight against the spread of infectious diseases in populations. Vaccines also offer protection at the individual level by preventing infection entirely or by reducing the severity of the illness. Diseases such as smallpox and polio, to name just a few, have been largely or entirely eradicated thanks to successful vaccination campaigns in the past. More recently, mass immunization has played a crucial role in limiting the impact of the COVID-19 pandemic despite widespread pushback over concerns about the immediate side-effects and potential long-term effects of the vaccines. As will be more or less apparent, vaccines that are considered to be safe and effective can provide a benefit to society as a whole and can reduce the demands that are placed on health care systems, even without 100% uptake within a population.

Vaccines are typically administered either intramuscularly or subcutaneously, but other administration routes are known, including oral administration, intradermal administration, and transcutaneous administration. Subcutaneous administration of a vaccine is performed using a needle long enough to reach the adipose layer under the skin (hypodermis), and as the name implies an intramuscular administration of a vaccine is performed using a needle long enough to reach the muscle under the adipose layer. Conventional syringes used for subcutaneous or intramuscular vaccinations can inject large volumes of vaccine solution, which often exceeds 1 ml and includes suitable adjuvants to enhance the body's immune response to the antigen in the vaccine solution. These types of injections can produce localized discomfort and swelling at the injection site, as well as more serious side-effects including fever, chills, and body aches.

Subcutaneous and intramuscular vaccination techniques also have other known drawbacks or limitations. Typical devices used for subcutaneous and intramuscular injections are hypodermic syringes, which present a stick-injury risk, have a dead volume that results in wasted vaccine, may require a relatively large amount of vaccine to trigger a suitable immune response, cause patient anxiety due to fear of needles, and must be administered by a trained nurse, pharmacist, doctor etc., thereby limiting the number of people that can be vaccinated in a short period of time. Further, muscle tissue has a low density of immune cells and is thus not an optimal site for immunization.

In contrast, skin tissue contains a broad array of antigen-presenting cells (APCs), which are likely to affect the magnitude, duration, and orientation of antigen-specific immune memory, and represents a potentially superior vaccine delivery route. Human skin has a surface area of approximately 2 $m^2$ and is around 2.5 mm thick on average, making it the largest organ of the human body. The skin has two broad tissue types, the epidermis, and the dermis. The epidermis is a continually keratinizing stratified epithelium. The outermost layer of skin is the stratum corneum (horny layer) and functions as the primary barrier. The stratum corneum is a 15-30 cell thick layer of non-viable but biochemically active corneocytes. The other three strata of the epidermis (*S. granulosum, S. spinosum, S. basale*) all contain keratinocytes at different stages of differentiation, melanocyte producing melanin which protects the skin from UV rays, as well as the immune Langerhans cells and dermal dendritic cells. The term epidermal vaccination refers to a vaccination method targeting the epidermis after passing through the horny layer with a micro-needle. These semi-invasive techniques can target Langerhans cells and sometimes dermal dendritic cells, depending on the depth reached.

The dermis is a dense, fibrous, and elastic tissue, which serves as the solid support for the skin. The rich vascularization of the dermis by blood and lymphatic vessels facilitates recruitment of immune cells (Langerhans cells, neutrophils, monocytes, monocyte derived DCs, memory T cells etc.) and recirculate and activate through the activity of multiple locally produced inflammatory chemokines and cytokines. Intradermal vaccination designates the delivery of an antigen directly into the dermis with either a syringe and a needle or a micro-needle, or with a pressure injector. The intradermal route targets mainly dermal dendritic cells, and macrophages.

Performing an epidermal injection or an intradermal injection requires considerable skill if administered with traditional syringes in order to deliver the vaccine at the targeted depth. Depending on the device that is being used to perform the injection, the application of too much or too little force, or the angle of the device being too steep or too shallow relative to the skin, it is possible that the vaccine will either flow back out onto the outer surface of the skin or will be transported to lower tissues under the dermis. The lack of reproducibility of these types of injections, especially between subjects of different ages, can be a problem.

Various injection devices, which are capable of delivering vaccines or other medicaments from a container to a target injection site, are known in the art. Selection of a suitable injection device for a particular vaccine depends on many factors, including the target injection site for the vaccine, the age of the vaccine recipient, the skill level of the individuals administering the vaccine, etc. That being said, known injection devices can be placed into one of two very broad categories—manual devices and auto-injectors. In a manual device, the user must provide the mechanical energy that is required to drive the fluid through the needle. This is typically done via some form of button or plunger that has to be continuously pressed by the user during the injection. There are numerous disadvantages associated with this approach. If the user stops pressing the button or plunger, then the injection will also stop. This means that the user can deliver an underdose if the device is not used properly (i.e., the plunger is not fully pressed to its end position). In addition, the required force that must be applied to the button or plunger may be too high for the user, in particular if the user is elderly or has dexterity problems. Further, the extension of the button or plunger may be too great and thus it can be inconvenient for the user to reach when fully extended. The combination of injection force and button or plunger extension can cause trembling or shaking of the hand, which in turn increases discomfort for the subject receiving the injection as the inserted needle moves within the target tissue. Additionally, manual devices such as syringe needles often must be filled in a manual fashion with a vaccine or other medicament from a vial. This adds an extra step, which can be significant in the case of large-scale vaccinations. Manual filling can also pose a risk of contaminating the syringe.

Auto-injector devices aim to make self-administration of injected therapies feasible for patients. Current therapies delivered by means of self-administered injections include drugs for diabetes (both insulin and newer GLP-1 class drugs), migraine, hormone therapies, anticoagulants etc. Auto-injectors are devices which completely or partially replace the manual activities that are involved in performing an injection using standard syringes. These activities include removal of a protective syringe cap, insertion of a needle into a subject's skin, injection of the vaccine or other medicament, removal of the needle, shielding of the needle and preventing reuse of the device. Each of these activities have an associated, but often unrecognized cost, associated therewith when performed using a manual injection device. Triggering of the auto-injector may be performed by numerous means, for example a trigger button or the action of the needle reaching its injection depth. In some devices the energy to deliver the fluid is provided by a spring.

As will be apparent, the task of selecting the best injection site and the best type of injection device for administering a particular vaccine is quite complicated. This task can be complicated even further if there is a need to incorporate the use of supplemental techniques to facilitate the delivery and/or uptake of the injected substance. One such supplemental technique is electroporation, which involves the application of brief electrical pulses that result in the creation of aqueous pathways within the lipid bi-layer membranes of mammalian cells. This allows the passage of even large molecules, including DNA plasmids, through the cell membrane, which would otherwise be less permeable. Injection devices that are capable of performing electroporation are also known in the art.

Although various auto-injector devices are known, none currently provides an optimized approach for delivering vaccines or other medicaments to the dermal/epidermal layer. Most of the known devices are simple in design and do not incorporate all of the functionality that is necessary to permit safe and reproducible injections by untrained users or by users with limited training. More particularly, known devices are not capable of advancing the needle or needle array, injecting the full dose of vaccine or other medicament every time, performing electroporation, optionally performing other supplemental techniques, and retracting the needle or needle array in a timed sequence beginning with the activation of the injection device. Nor do they have a robust way of activating the ever-present dormant potential to respond to offending antigens due to a repeated mechanical stimulation, puncture/trauma of the Langerhans and other immune cells that can be activated through complex not fully understood cytokine release. It would therefore be beneficial to provide an improved auto-injector that overcomes at least some of the limitations of the prior art.

SUMMARY OF EMBODIMENTS

In accordance with an aspect of at least one embodiment there is provided an auto-injector for injecting an injectable substance into at least one of the epidermal tissue and the dermal tissue of a subject, the auto-injector comprising: an outer housing; a control member disposed within the outer housing; a needle array comprising a plurality of needles, the needle array movable between a retracted position in which the needles are disposed entirely within the outer housing and an extended position in which the needles are disposed at least partially outside the outer housing; first means configured to be driven by the control member during injecting of the injectable substance, wherein movement of the control member is converted into translational movement of the needle array between the retracted position and the extended position; and second means configured to produce an oscillatory translational motion of the needle array when the needle array is in the extended position.

In an embodiment the control member is a rotatable control member comprising a control cylinder having a first control groove formed along an inner surface thereof and the first means comprises a follower plate coupled to the needle array, the follower plate including a protrusion seated within the first control groove, wherein rotation of the rotatable control member guides the protrusion along the first control groove including a portion thereof having a component along the length direction of the auto-injector for producing the translational movement of the needle array between the retracted position and the extended position In an embodiment an energy source is provided in communication with the rotatable control member and in communication with the second means for respectively providing energy to rotate the rotatable control member and to produce the oscillatory translational motion of the needle array.

In an embodiment the energy source includes a torsion spring configured to store mechanical potential energy and a flywheel for converting the mechanical potential energy released from the torsion spring into stored rotational kinetic energy.

In an embodiment the energy source includes an electric motor and a DC electrical power supply or an AC electrical power supply in electrical communication with the electric motor.

In an embodiment the second means includes a rotatable plate disposed in a stacked arrangement with a stationary plate, the stationary plate having a grooved surface facing the rotatable plate and defining a series of depressions and ridges, and further includes a pair of spherical spacer elements retained within openings formed in the rotating plate, and wherein each of the pair of spherical spacer elements are guided over the ridges between respective adjacent pairs of depressions when the rotatable plate rotates such that a separation distance between the rotatable plate and the stationary plate varies in an oscillatory fashion over time.

In an embodiment a plunger assembly is provided including a plunger and a gas cylinder that contains a known volume of a gas prior to injecting the injectable substance.

In an embodiment an interface is provided for receiving a container containing the injectable substance, the interface fluidly coupled to the gas cylinder via a first conduit, and the interface fluidly coupled to the needle array via a second conduit.

In an embodiment the known volume of gas is equal to a combined volume of the first conduit, the second conduit, the container received within the interface, and a dead volume of the needle array.

In an embodiment the interface includes a housing that is keyed or shaped to receive only a correspondingly keyed or shaped container, and wherein the keying or shaping is specific to a known injectable substance or to a known set of injectable substances.

In an embodiment an electric current source is provided in electrical communication with at least some needles of the needle array via a conductor, for providing an electroporation current to the at least one of the epidermal tissue and the dermal tissue of the subject during injecting the injectable substance, wherein said at least some needles are hollow or solid needles fabricated from an electrically conductive material.

In an embodiment the control cylinder further includes a second control groove and a third control groove each formed along the inner surface of the control cylinder, wherein the second control groove controls movement of the plunger and the third control groove controls actuation of the electric current source, and wherein the shapes of the first, second and third control grooves are configured to control the translational movement of the needle array, the movement of the plunger, and the actuation of the electric current source in a pre-determined timed-sequence for injecting the injectable substance.

In an embodiment a sealing skirt or gasket is arranged at an injecting end of the outer housing for forming a seal against the subject's skin during injecting of the injectable substance, wherein the seal is substantially gas-tight such that a partial vacuum is formed above the subject's skin when the needle array is moved from the extended position to the retracted position, whereby the partial vacuum produces a suction effect.

In accordance with an aspect of at least one embodiment there is provided an auto-injector for injecting an injectable substance into at least one of the epidermal tissue and the dermal tissue of a subject, comprising: a rotatable control cylinder having a plurality of control grooves formed along an inner surface thereof and having a plurality of alignment protrusions projecting outwardly away from an outer surface thereof, a housing disposed in a spaced-apart concentric arrangement with the rotatable control cylinder and extending along at least a portion of a length of the rotatable control cylinder, the housing comprising a plurality of alignment grooves formed along an inner surface thereof for receiving the alignment protrusions of the rotatable control cylinder when the auto-injector is in an assembled condition; a needle array comprising a plurality of needles; first means configured to rotate the rotatable control cylinder relative to the outer housing during injecting of the injectable substance, wherein rotational movement of the rotatable member is converted into translational movement of the needle array between the retracted position and the extended position; and second means configured to produce an oscillatory translational motion of the needle array when the needle array is in the extended position, wherein during use the needles of the needle array extend beyond the skin-contacting end of the auto-injector and penetrate the subject's skin to a predetermined target depth when the needle array is in the extended position.

In accordance with an aspect of at least one embodiment there is provided an injector for injecting an injectable substance into at least one of the epidermal tissue and the dermal tissue of the skin of a subject, the injector comprising: an outer housing; a control member disposed within the outer housing; a needle head configured to support a plurality of needles; first means in communication with the control member and configured to be driven by the control member for converting a movement of the control member into a movement of the needle head along an injection direction and toward an injecting position of the needle head; and second means configured to move the needle head in a direction having a component that is normal to the injection direction and absent movement of the outer housing relative to the skin of the subject.

In accordance with an aspect of at least one embodiment there is provided an auto-injector for injecting an injectable substance into at least one of the epidermal tissue and the dermal tissue of a subject, including: an outer housing; a needle array including a plurality of needles and being movable between a retracted position in which the needles are disposed entirely within the outer housing and an extended position in which the needles are disposed at least partially outside the outer housing; a plunger member in fluid communication with a source of the injectable substance; a control cylinder having a plurality of grooves formed along an inner surface thereof and comprising at least: a plunger control groove; and a needle array control groove; and means for rotating the control cylinder relative to the outer housing, the plunger member, and the needle array; wherein the control cylinder is in mechanical communication with the needle array via the needle array groove and is in mechanical communication with the plunger member via the plunger control groove, and wherein the plunger control groove and the needle array control groove are individually shaped in both the circumferential direction and in the longitudinal direction of the control cylinder for converting rotational motion of the control cylinder into predetermined translational motions of the plunger member and of the needle array, respectively, and wherein the shapes of the plunger control groove and of the needle array control groove cooperate to define a timing sequence of the predetermined translational motions of the plunger member and of the needle array during an injection event.

In accordance with an aspect of at least one embodiment there is provided an auto-injector for injecting an injectable substance into at least one of the epidermal tissue and the dermal tissue of a subject, comprising: an outer housing; a needle array comprising a plurality of needles, the needle array being movable between a retracted position in which the needles are disposed entirely within the outer housing and an extended position in which the needles are disposed at least partially outside the outer housing; a flywheel disposed within the outer housing for storing rotational kinetic energy; an oscillator element rotationally coupled to the flywheel for converting a first portion of the stored rotational kinetic energy into an oscillatory translational movement of the needle array; a gear system coupled to the flywheel; a control cylinder comprising: a circumferential ring gear formed on an inner surface thereof, the ring gear engaging gears of the gear system for transferring a second portion of the stored rotational kinetic energy into rotational motion of the control cylinder; and a plurality of control grooves formed on the inner surface thereof; and a plate member fixedly coupled to the needle array, the plate member having a protrusion extending therefrom that is received in a first control groove of the plurality of control grooves, wherein rotation of the rotatable control member guides the protrusion along the first control groove including a portion thereof having a component along the length direction of the auto-injector for producing the translational movement of the needle array between the retracted position and the extended position.

In accordance with an aspect of at least one embodiment there is provided a method for injecting an injectable substance into at least one of the epidermal tissue and the dermal tissue of a subject using an injector, the method comprising: placing an injecting end of the injector into contact with an area of the subject's skin, the injector containing a single dose of the injectable substance having a dose volume; triggering an automatic injection sequence of the injector, wherein the automatic injection sequence comprises: moving a needle array comprising a plurality of needles along an injection direction and penetrating the subject's skin at a first plurality of locations; injecting a first portion of the dose volume into the subject's skin at the first plurality of locations; at least partially withdrawing the plurality of needles from the subject's skin; moving the needle array comprising the plurality of needles along a direction having a component that is normal to the injection direction; moving the needle array comprising the plurality of needles along the injection direction and penetrating the subject's skin at a second plurality of locations, at least some of the second plurality of locations being different from at least some of the first plurality of locations; and injecting a second portion of the dose volume into the subject's skin at the second plurality of locations, wherein the auto-injector is in contact with the same area of the subject's skin during performance of the entire automatic injection sequence, such that the entire dose volume of the injectable substance is injected absent moving the auto-injector along the subject's skin.

In accordance with an aspect of at least one embodiment there is provided a method for injecting an injectable substance into at least one of the epidermal tissue and the dermal tissue of a subject using an auto-injector, the method comprising: placing an injecting end of the auto-injector in contact with an area of the subject's skin, the auto-injector containing a single dose of the injectable substance having a dose volume; triggering an automatic injection sequence of the auto-injector, wherein the automatic injection sequence comprises; extending a needle array of the auto-injector along a length direction of the auto-injector from a retracted position to an extended position in which needles of the needle array penetrate the subject's skin to a target depth; controllably depressing a plunger member to transfer the injectable substance from a storage container to the needle array; continuing to depress the plunger member to inject the entire dose volume of the injectable substance into the subject's skin via the needle array; during the step of continuing to depress the plunger, moving the needle array with an oscillatory translational motion along the length direction of the auto-injector; and retracting the needle array of the auto-injector along the length direction of the auto-injector from the extended position back to the retracted position, wherein the auto-injector is held in contact with the same area of the subject's skin during performance of the entire automatic injection sequence, such that the entire dose volume of the injectable substance is injected absent moving the auto-injector along the subject's skin.

In accordance with an aspect of at least one embodiment there is provided an auto-injector for injecting an injectable substance into at least one of the epidermal tissue and the dermal tissue of a subject, the auto-injector comprising: an outer housing, containing: an interface for receiving a container with an internal volume containing the injectable substance; a needle array comprising a plurality of needles and being in fluid communication with the interface via a conduit; means for extending the needle array between a retracted position and an extended position in which the plurality of needles is at least partially outside the outer housing; an oscillator element for moving the needle array in an oscillating fashion and in a direction that is generally normal to the subject's skin when the needle array is in the extended position; an electric current source in electrical communication with the needle array via a conductor for providing an electroporation current to the at least one of the epidermal tissue and the dermal tissue of the subject during injecting the injectable substance; and a plunger assembly in fluid communication with the interface for pressurizing the volume of the container when moved from an initial position to a depressed position, to move the injectable substance out of the container and to the needle array via the conduit, wherein an injecting end of the outer housing includes a seal element for forming a substantially gas-tight seal against the subject's skin, and wherein after injecting the injectable substance the plunger assembly is configured to return to the initial position thereof to draw gas from the injecting end of the outer housing through the conduit to create an area of reduced pressure above the subject's skin and thereby produce a suctioning effect.

In accordance with an aspect of at least one embodiment there is provided an auto-injector for injecting an injectable substance into at least one of the epidermal tissue and the dermal tissue of a subject, the auto-injector comprising: an outer housing having a sealing element disposed at a skin-contacting end thereof for forming a substantially gas-tight seal when the sealing element is placed into contact with the subject's skin; a needle array comprising a plurality of needles; means for moving the needle array between a retracted position within the outer housing and an extended position in which the plurality of needles is at least partially outside the outer housing; means for moving the needle array in an oscillatory fashion when the needle array is in the extended position; means for applying an electroporation current via at least some needles of the needle array when the needle array is in the extended position; a plunger assembly for providing the injectable substance to the needle assembly under pressure, when the needle assembly is in the extended position, and for creating an area of reduced pressure within the skin-contacting end of the outer housing, when the needle assembly is moved from the extended position to the retracted position.

In accordance with an aspect of at least one embodiment there is provided a method for injecting an injectable substance into at least one of the epidermal tissue and the dermal tissue of a subject using an auto-injector, the method comprising: placing an injecting end of the auto-injector in contact with an area of the subject's skin, the auto-injector containing a single dose of the injectable substance having a dose volume; triggering an automatic injection sequence of the auto-injector, wherein the automatic injection sequence comprises; penetrating the subject's skin to a target depth with needles of a needle array of the auto-injector; injecting the entire dose volume of the injectable substance into the subject's skin via the needle array absent moving the auto-injector along the subject's skin; during injecting, moving the needle array with an oscillatory translational motion along a direction substantially normal to the subject's skin; during injecting, applying an electroporation current via at least some of the needles of the needle array; forming a region of reduced pressure at the injecting end of the auto-injector for applying suction to the subject's skin prior to moving the injecting end of the auto-injector out of contact with the area of the subject's skin; and moving the needle array of the auto-injector to the retracted position in which the needles of the needle array are out of contact with the subject's skin.

BRIEF DESCRIPTION OF THE DRAWINGS

Exemplary embodiments will be described in accordance with the drawings, which are not drawn to scale, and in which:

FIG. 14A is a simplified side view showing the needle control sub-assembly of FIG. 9 in a fully retracted position within the control cylinder of FIG. 3 and the external housing of FIG. 2.

FIG. 14B is a simplified partial bottom perspective view showing the needle control sub-assembly of FIG. 9 in the fully retracted position.

37A shows the needles extending into the epidermis prior to injection of the injectable substance; FIG. 37B shows the injectable substance within the dermis and close to the injecting tips of the needles; FIG. 37C shows the injectable substance after spreading within the dermis; FIG. 37D shows the injectable substance after spreading within the dermis to a target depth; and FIG. 37E shows a response by the Langerhans cells to the injection of the injectable substance into the dermis.

FIGS. 45A-E is a series of illustrations showing the interactions between the external protrusions of the needle head and the two sets of internal protrusions of the rotation drive housing during the oscillatory motion of the needle head, in which: FIG. 45A shows the interactions prior to the start of the oscillatory motion; FIG. 45B shows the interactions at a first time after the start of the oscillatory motion; FIG. 45C shows the interactions at a second time after the start of the oscillatory motion; FIG. 45D shows the interactions at a third time after the start of the oscillatory motion; and FIG. 45E shows the interactions at a fourth time after the start of the oscillatory motion.

FIG. 45G is a top view showing a linear drive housing in isolation.

FIG. 45H is a top view showing a needle head for use with the linear drive housing.

DETAILED DESCRIPTION OF THE DRAWINGS

Figure 1:
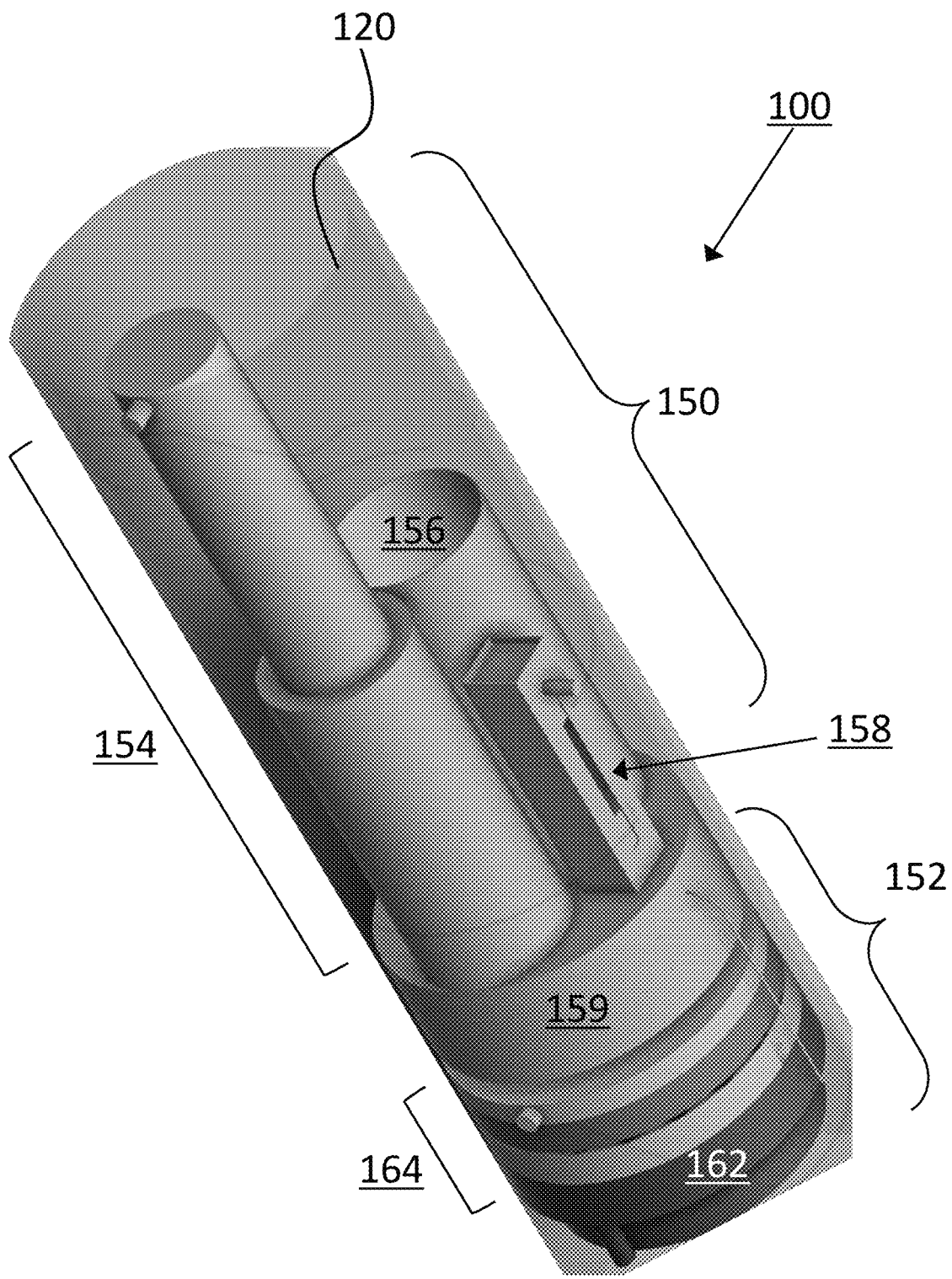
FIG. 1 is a simplified perspective view showing the main features of an injector according to an embodiment.

While the present teachings are described in conjunction with various embodiments and examples, it is not intended that the present teachings be limited to such embodiments. On the contrary, the present teachings encompass various alternatives and equivalents, as will be appreciated by those of skill in the art. All statements herein reciting principles, aspects, and embodiments of this disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

1. Definitions

The term "electroporation" as used herein refers to the use of a transmembrane electric field pulse to induce microscopic pathways (pores) in a bio-membrane. The pores allow biomolecules such as plasmids, oligonucleotides, siRNA, drugs, ions, and water to temporarily pass from one side of the cellular membrane to the other.

The term "minimally invasive" refers to the limited penetration of the needles into the skin layers of the subject. Preferably, the needles penetrate the stratum corneum and enter into the epidermal layer and depending on the needle design and pressure used it may be optimal for the needle to remain in the epidermis or extend to the dermis but to not extend to the subcutaneous layer. The maximum penetration depth of the needles preferably does not exceed, as per IONAID, 2.58 mm. In some embodiments the automatic injector is equipped with sets of needles having different lengths, and the penetration depth is preferably in the range between about 0.2 mm and about 2.5 mm.

The term "injectable substance" refers to a liquid containing an active agent such as for instance a vaccine or another medicament that is to be delivered to a subject via an injection into one or more layers of the subject's skin tissue. The injectable substance may include suspended solid particles, or it may be a homogeneous liquid. The injectable substance may include other components in addition to the active agent, such as for instance adjuvants. Alternatively, the injectable substance does not include adjuvants. The vaccine type may be selected from the following: a DNA vaccine; a messenger RNA (mRNA) vaccine; Virus-like particle (VLP) vaccine; an inactivated vaccine; a live-attenuated vaccine; a subunit, recombinant, polysaccharide, or conjugate vaccine; a toxoid vaccine; a viral vector vaccine; a cancer vaccine or any other antigen specific producing vaccine therapeutic and/or disease preventing or immune modulating (for example, allergy mitigating) technology.

The term "subject" refers to a mammalian living organism receiving an injection using the auto-injector. The subject may be a human or another type of mammal. In the case of self-injection, the subject is a human and is also the user or the operator of the injector.

The terms "top" and "upper" and similar equivalents, as used herein, are intended to refer to the specific orientation of the injector as depicted in the drawings. Similarly, the terms "bottom" and "lower" and similar equivalents are also intended to refer to the specific orientation of the injector as depicted in the drawings. These terms and their similar equivalents are merely labels of convenience, which are used to facilitate a better understanding of the disclosed embodiments, and which are not intended to imply any particular orientation of the injector during an actual injection.

The terms "outer housing" as used herein refers to a housing that is disposed outwardly of the rotatable control member (control cylinder). In some embodiments an "outer housing" may be an outermost housing. In other embodiments additional housings may be disposed outwardly of an "outer housing." An "outer housing" may be a housing that is continuous along the length direction of the injector, or an "outer housing" may be two or more discontinuous housing-portions that collectively form the "outer housing."

The term "oscillatory translational motion" as used herein refers to a movement of a component or an assembly over a first distance along a first direction with a subsequent movement of the component or the assembly over a second distance along a second direction. In some embodiments "oscillatory translational motion" consists of a single movement along the first direction followed by a single movement along the second direction, i.e., a single oscillation. In some embodiments "oscillatory translational motion" includes at least two such single oscillations. In some embodiments "oscillatory translational motion" includes 2 to 100 such single oscillations. In some embodiments, the second direction is opposite the first direction. In some embodiments, the second distance is substantially the same as the first distance such that there is a net zero movement of the component or assembly after the "oscillatory translational motion." In some embodiments the second distance is greater than or less than the first distance.

The terms "auto-injector" and "automatic injector" as used herein refer to an injector device that, once it has been triggered, performs a predetermined series of steps for injecting an injectable substance into a subject. In some embodiments, the subject may trigger the "auto-injector" or "automatic injector" to perform a self-injection. In some embodiments a user may trigger the "auto-injector" or "automatic injector" to perform an injection into someone else.

2. Injector

The present disclosure is directed to an injector device, which in some embodiments may be an auto-injector or an automatic injector, having a needle array that is extendable and retractable relative to an outer housing. In various embodiments, the injector performs one or more of the following:

Extending the needle array from a storage (retracted) position to an injecting (extended) position.
Oscillating the needle array along a length direction of the injector (i.e., substantially normal to the subject's skin) while the needle array is in the injecting position.
Transferring an injectable substance from a storage container to the needle array.
Injecting the injectable substance into the epidermal and/or dermal tissue of the subject via the needle array.
Applying an electric current for inducing electroporation during and/or after injection of the injectable substance into the epidermal and/or dermal tissue of the subject.
Forming an area of reduced pressure (mild or partial vacuum) above a site of the injection during retracting of the needle array back into the storage position.

In various embodiments, the injector is an auto-injector that may require 0.5-5 seconds to perform an injection, preferably 1-3 seconds to perform an injection, more preferably no more than about 2 seconds to perform an injection. In various embodiments, oscillating the needle array along the length direction of the auto-injector includes translating the needle array over a distance of 0.1 mm to 3.0 mm, preferably about 0.5 mm between reversing direction during each oscillation. In various embodiments, the injectable substance is transferred and injected under pressure provided by a plunger assembly and using a precisely calibrated amount of a gas to displace all of the injectable substance from the auto-injector and into the subject's skin. A control assembly, for example a rotating grooved-cylinder, controls various sub-assemblies of the auto-injector to ensure the injection of the injectable substance is matched with the deepest needle penetration into the skin. In various embodiments, an electric current for inducing electroporation (i.e., the electroporation current) is applied as a single pulse, or as a pulse train comprising a plurality of pulses that are either of the same or varying duration and/or intensity. In various embodiments at least some of the needles of the needle array are fabricated from an electrically conductive material and are used for applying the electroporation current. In various embodiments, the needles of the needle array are fabricated from a non-conducting material and separate electrodes, also referred to as solid needles, are provided within the needle array for applying the electroporation current. In various embodiments, the mild or partial vacuum is sufficient to apply suction to (i.e., cupping of) the subject's skin.

Referring now to FIG. 1, shown is a simplified perspective view showing the various elements, sub-assemblies and/or assemblies of an injector in the form of an auto-injector 100 according to an embodiment. The auto-injector 100 that is shown in FIG. 1 is a specific and non-limiting example, which is suitable for, e.g., performing an automatic injection of an injectable substance, such as for instance a vaccine solution or another medicament. The auto-injector 100 is configured for injecting the injectable substance into the skin tissue of a subject, and more specifically into the epidermal tissue below the stratum corneum. Of course, the auto-injector 100 may be modified and adapted to be suitable for other purposes such as, e.g., withdrawing fluids from the tissues of the subject, injecting vaccine solutions or other medicaments at different depths including depths that are suitable for subcutaneous and intramuscular injections, and even measuring voltages or currents for interrogating the tissues of the subject, etc. As will be apparent, modified versions of the auto-injector 100 may not need to perform all of the functions that are listed in the previous paragraphs, or alternatively such modified versions of the auto-injector may need to perform functions in addition to the ones that are listed in the previous paragraphs.

Figure 2:
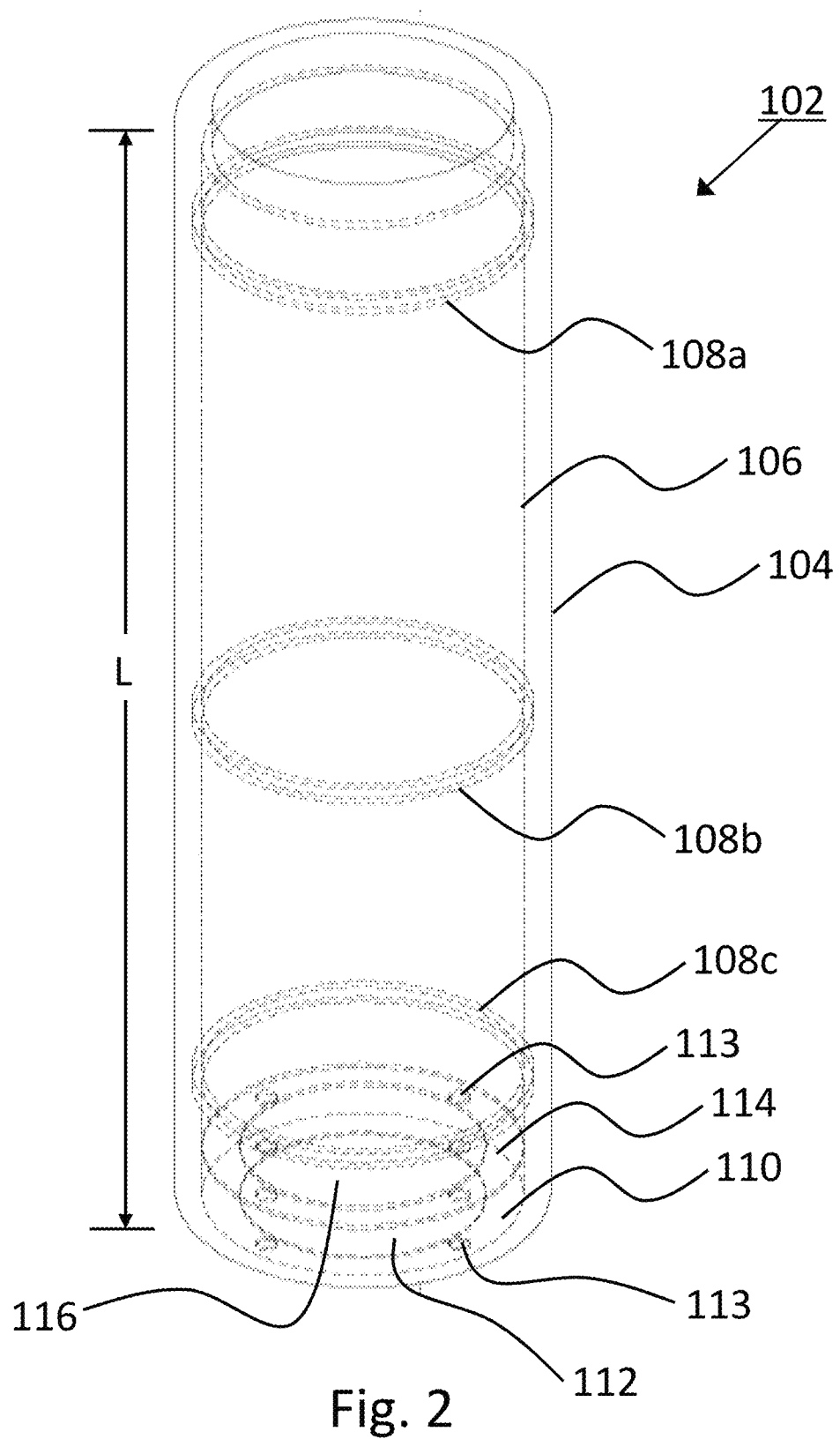
FIG. 2 is a simplified perspective view showing the external and internal features of an outer housing according to an embodiment.

The auto-injector 100 comprises an outer housing 102, which is not shown in FIG. 1 for improved clarity, but which is shown in FIG. 2. In the specific and non-limiting example described herein, the outer housing 102 is generally cylindrical in shape and has an outer surface 104 for being gripped by a user when an injection is being administered to the subject. The outer housing 102 may be fabricated from a suitable hard plastic material or from another suitable material such as for instance a metal or a ceramic material, and may include various ergonomic features, including curved surfaces and/or textured surfaces, rubbery gripping inserts, etc., to facilitate gripping by the user. In the specific example that is shown in FIG. 2 the outer housing 102 is approximately 13 cm in length and approximately 2.5 cm in diameter and is capable of being easily gripped by most users. Other form factors may be envisaged for the auto-injector 100, including a computer mouse-like shaped device that is gripped in the palm of the user and pressed against the subject's skin.

Referring still to FIG. 2, the internal surface 106 of the outer housing 102 has a plurality of circumferential grooves formed therein. In the specific example that is shown in FIG. 2 there are three circumferential grooves 108a-108c, which are spaced-apart along the length L of the outer housing 102. The circumferential grooves 108a-108c are configured to receive mating protrusions that are arranged along an outer surface of a rotatable control cylinder 120 (which is shown in FIG. 1 but not in FIG. 2), as is discussed below in more detail. One end of the outer housing 102, i.e., an injecting end thereof, has a radially inwardly extending end surface 110 with a central opening 112. In addition, a radially inwardly extending flange 114 with a central opening 116 is located proximate the injecting end of the outer housing 102 and is spaced apart from the radially inwardly extending end surface 110 along the length L of the outer housing 102. During an injection, a needle array (not shown in FIG. 2) passes through the central openings 112 and 116 as it moves between a retracted position and an extended position thereof. The end surface 110 and the flange 114 also have a plurality of smaller openings 113 defined therethrough. The smaller openings 113 in the end surface 110 are aligned with the smaller openings 113 in the flange 114 for receiving not illustrated actuation legs or shafts of a trigger mechanism therein. The actuation legs or shafts perform a stabilizing function in addition to their function in triggering the auto-injector 100. In particular, the actuation legs or shafts prevent relative rotational movement of the various components through which they extend.

Figure 3:
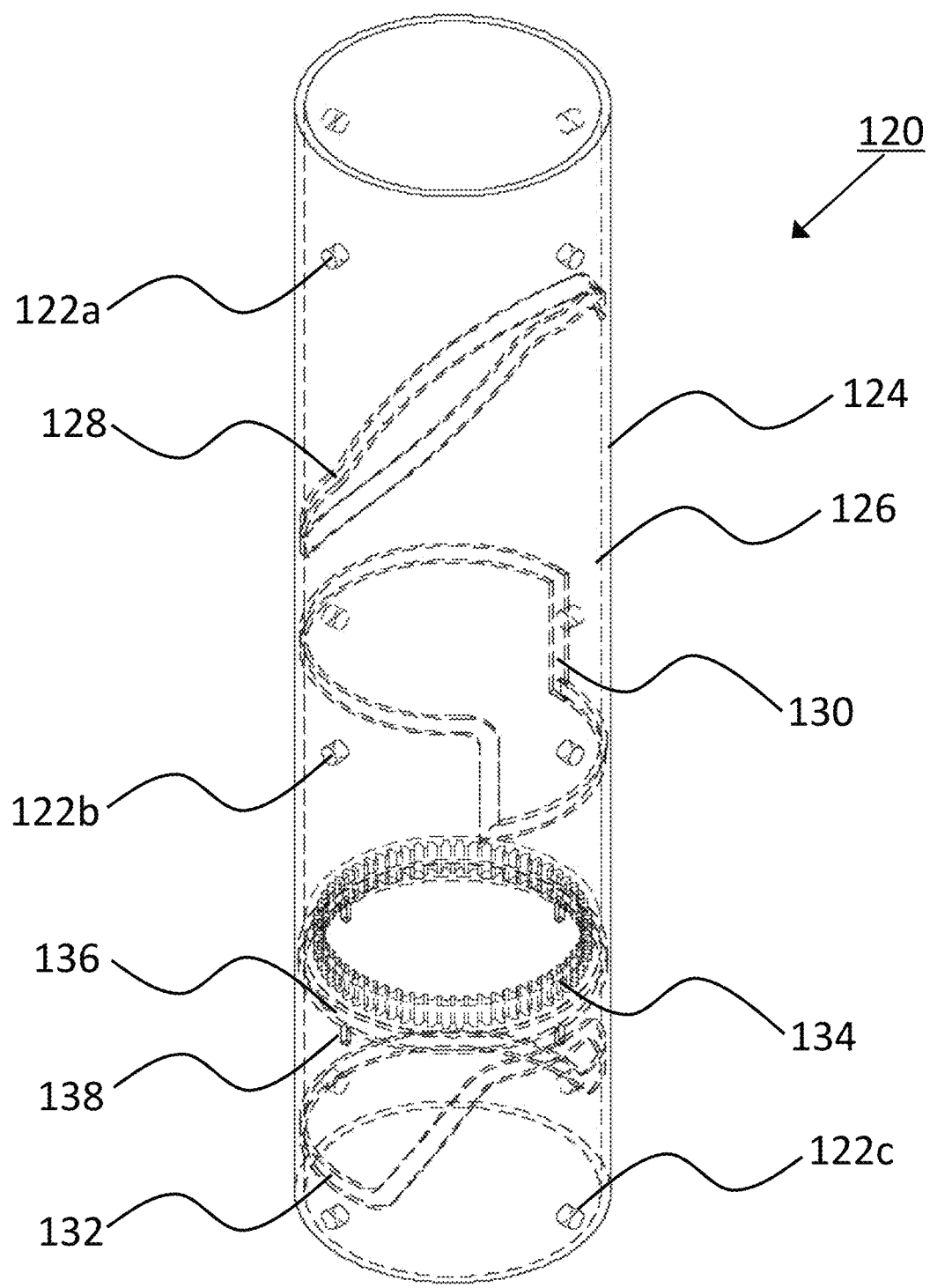
FIG. 3 is a simplified perspective view showing the external and internal features of a control cylinder according to an embodiment.
Figure 4:
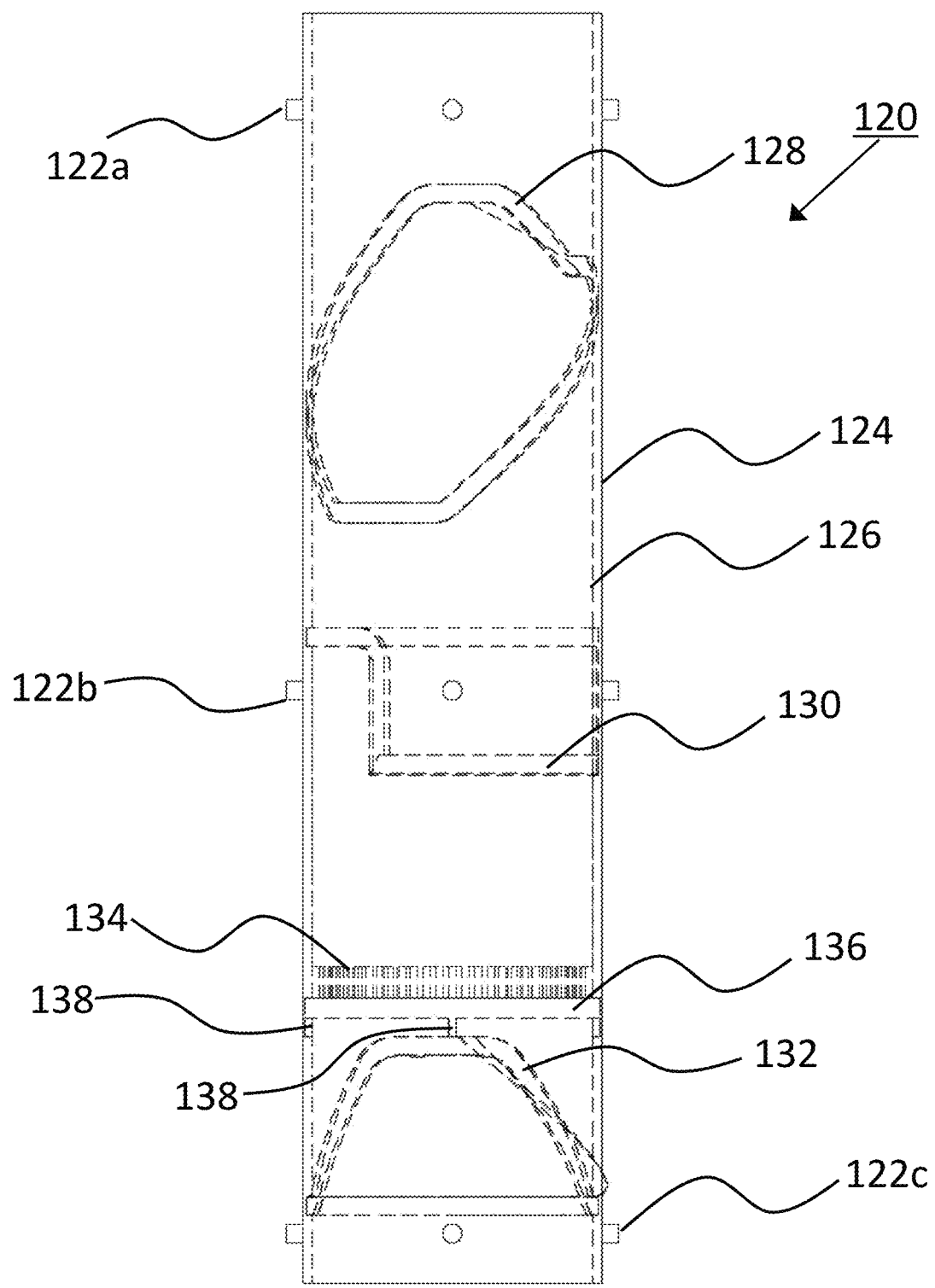
FIG. 4 is a simplified side view showing the external and internal features of the control cylinder of FIG. 3, viewed from a different point around the circumference of the control cylinder.
Figure 5:
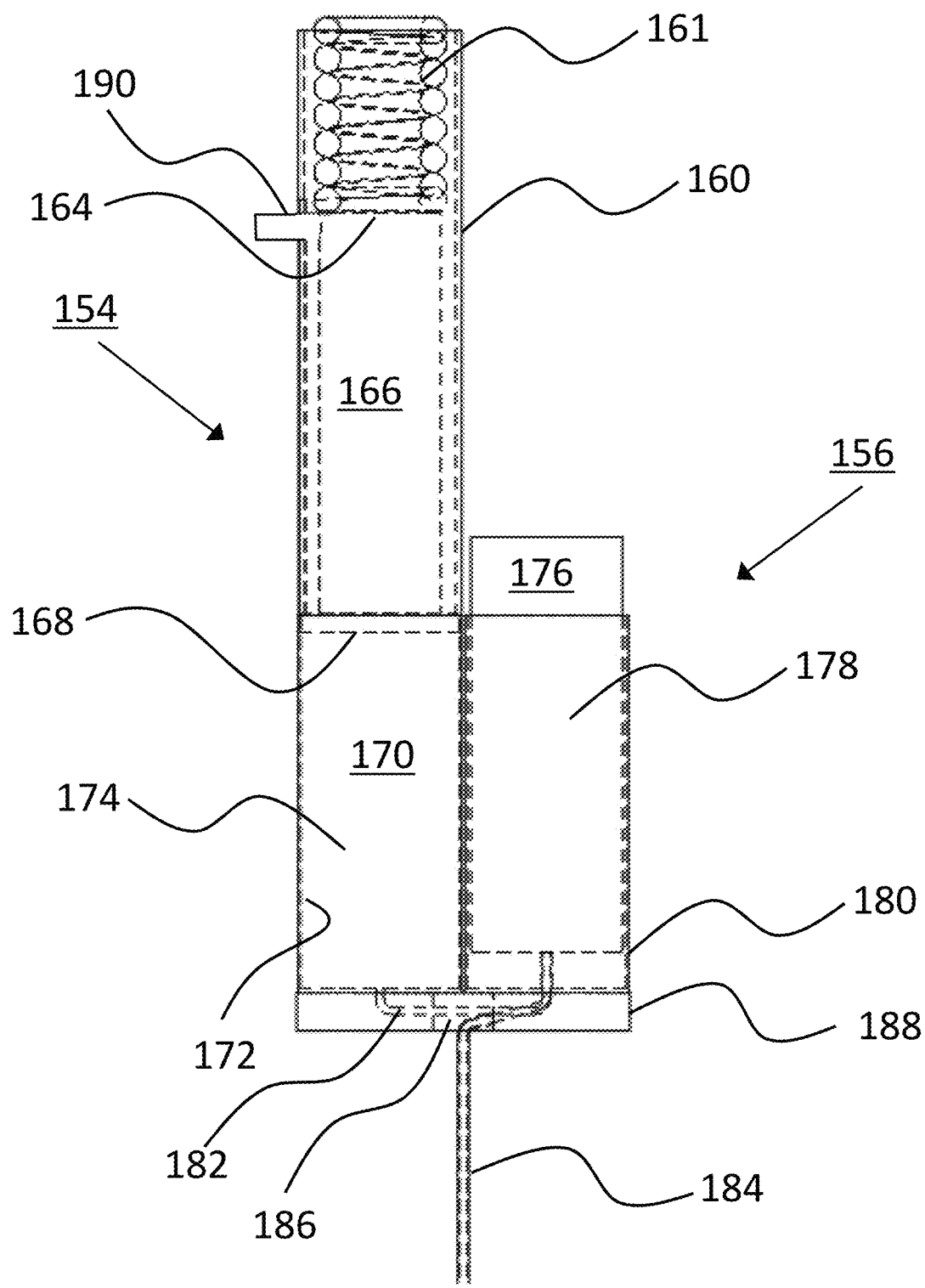
FIG. 5 is a simplified side view showing a plunger and vial interface sub-assembly according to an embodiment.
Figure 6:
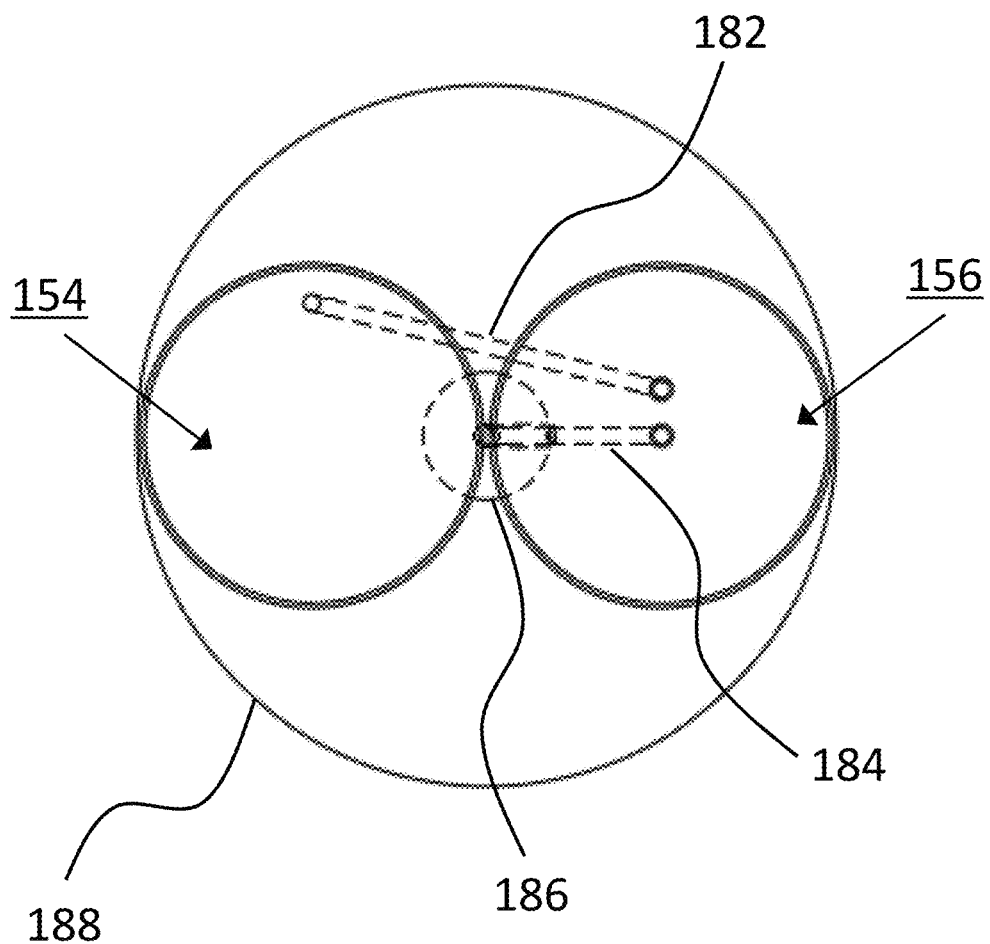
FIG. 6 is a simplified bottom view of the sub-assembly of FIG. 5.

FIGS. 3-4 show the above-mentioned control cylinder 120, which is also shown in FIG. 1 as a transparent cylinder. The control cylinder 120, which may be fabricated from a suitable hard plastic, metal or ceramic material, etc., is nested within the outer housing 102 when the auto-injector 100 is in the assembled condition. Sets of protrusions 122a-122c extend radially outwardly away from the outer surface 124 of the control cylinder 120 and are received within respective ones of the circumferential grooves 108a-108c of the outer housing 102 when the auto-injector 100 is in the assembled condition. For instance, the outer housing 102 comprises two halves that that are secured together (e.g., via welding, adhesives, and/or mechanical fasteners, etc.) around the control cylinder 120 with the protrusions 122a-122c seated within the circumferential grooves 108a-108c.

In the specific example shown in FIGS. 3-4, each set of protrusions 122a-122c includes 4 separate protrusions circumferentially spaced around the control cylinder 120 (i.e., at 900 intervals). Alternatively, at least some of the sets of protrusions 122a-122c may include more than 4 protrusions or less than 4 protrusions and/or the separate protrusions in at least some of the sets of protrusions 122a-122c may be replaced by continuous or semi-continuous ridges that are shaped to be received within respective ones of the circumferential grooves 108a-108c of the outer housing 102. The control cylinder 120 is rotatable relative to the outer housing 102 after the auto-injector 100 has been triggered but is prevented from moving in the length direction relative to the outer housing 102 by the seating of the sets of protrusions 122a-122c within the circumferential grooves 108a-108c.

Referring still to FIGS. 3-4, features that are formed along the inner surface 126 of the control cylinder 120 are shown using dashed lines. In particular, a plurality of control grooves is formed along the inner surface 126 of the control cylinder, including i) a plunger control groove 128, ii) a piezoelectric element control groove 130, and iii) a needle array control groove 132. Also formed along the inner surface 126 of the control cylinder 120 is an internal ring gear 134 and a trigger mechanism control slot 136. A plurality of notches 138 open into the trigger mechanism control slot 136. The function of the internal ring gear 134, the trigger mechanism control slot 136 and the plurality of notches 138 is described in more detail below.

Now referring now to all of FIGS. 1-4, it is shown that various elements, sub-assemblies and/or assemblies are arranged inside the control cylinder 120, which is itself nested within the outer housing 102 of the auto-injector 100. The various elements, sub-assemblies and/or assemblies have been divided into an upper group 150 and a lower group 152 as shown in FIG. 1. This division is somewhat arbitrary but provides a convenient basis for describing the structure of the auto-injector 100 and the functioning thereof. It is to be understood that the various elements, sub-assemblies and/or assemblies may be arranged differently in the auto-injector 100, especially if the form factor of the auto-injector is different from the form factor that is described in this specific and non-limiting example.

Referring again to FIG. 1, the upper group 150, in this example, includes a plunger sub-assembly 154, a vial interface 156, and a piezoelectric element 158. The lower group 152, in this example, includes an energy source and storage sub-assembly 159, a needle head 162 and a needle control sub-assembly shown generally at 164.

Referring now to FIGS. 5-8, shown are different views of the plunger sub-assembly 154 and vial interface 156. The plunger sub-assembly 154 includes a housing 160, which was omitted in for clarity FIG. 1. A compression spring 161 is disposed within the housing 160 between one end 164 of a plunger member 166 and an end surface (not shown) of the housing 160. A second end 168 of the plunger member 166 is disposed within a gas cylinder 170. A substantially gas-tight seal is formed between the second end 168 of the plunger member 166 and an inner surface 172 of the gas cylinder 170. The gas cylinder 170 has an interior volume 174 for containing a suitable gas, such as for instance air. Alternatively, another suitable gas may be provided in the interior volume 174. Suitable gases include gases that are not irritating to human skin, non-toxic, non-combustible, etc.

A vial 176 having an internal volume 178 is inserted into and retained within a vial housing 180 of the vial interface 156. The vial 176 is, e.g., a vial of up to 5 ml capacity, or another suitable capacity depending on the injectable substance being injected, containing a known amount of a prepared injectable substance, such as for instance a vaccine solution. During an injection, after the auto-injector 100 has been triggered, the compression spring 161 exerts a force on the one end 164 of the plunger member 166, which displaces the second end 168 of the plunger member 166 into the gas cylinder 170. The contents of the gas cylinder 170, such as for instance a precisely known amount of a gas, e.g., air, is forced out through a first conduit 182 fluidly connecting the gas cylinder 170 to the interior volume 178 of the vial 176. The gas flowing into the interior volume 178 of the vial 176 forces the injectable substance out of the vial 176 via a second conduit 184. The second conduit 184 is routed, via an opening 186 in a support base or plate 188, to a not illustrated needle array to be injected into the tissue of the subject. The arrangement of the first conduit 182 and the second conduit 184 relative to the plunger sub-assembly 154 and vial interface 156 is shown most clearly in the top view of FIG. 6.

A protrusion 190 extends outwardly from the plunger member 166 proximate the one end 164 thereof. As shown most clearly in FIGS. 7 and 8, the protrusion 190 is retained within a slot 192 that is formed in the housing 160. The protrusion 190 extends outwardly through the slot 192 and is received within the plunger control groove 128 formed along the inner surface 126 of the control cylinder 120 (not shown in FIGS. 5-8). Although not shown in FIGS. 5-8, the housing 160 is fixedly secured to the outer housing 102 to prevent relative rotation therebetween. Accordingly, during operation, the control cylinder 120 rotates within a space (i.e., a substantially annular space) between the inner surface 106 of the outer housing 102 and the housing 160 of the plunger sub-assembly 154. As the control cylinder 120 rotates about a longitudinal axis parallel to the length, L, of the auto-injector 100, the protrusion 190 follows along within the plunger control groove 128, and when the shape of the plunger control groove 128 permits translational movement along the length direction, L, the compression spring 161 provides a sufficient force to advance the plunger member 166 into the gas cylinder 170. Thus, the protrusion 190 follows a path that is controlled by both the plunger control groove 128 and the slot 192 formed in the housing 160 to thereby control the translational movement of the plunger 166 during an injection.

The shape of the plunger control groove 128, in combination with the direction and speed of rotation of the control cylinder 120, controls the timing, or rate of advancement and retraction, of the movement of the plunger member 166. Portions of the plunger control groove 128 that extend only in the circumferential direction of the control cylinder 120 result in no translational movement of the plunger member 166. Portions of the plunger control groove 128 that extend in both the circumferential direction and the length direction of the control cylinder 120 result in translational movement of the plunger member 166. The greater the amount of extension of the plunger control groove 128 in the length direction, the greater the resulting translational movement of the plunger member 166.

Figure 7:
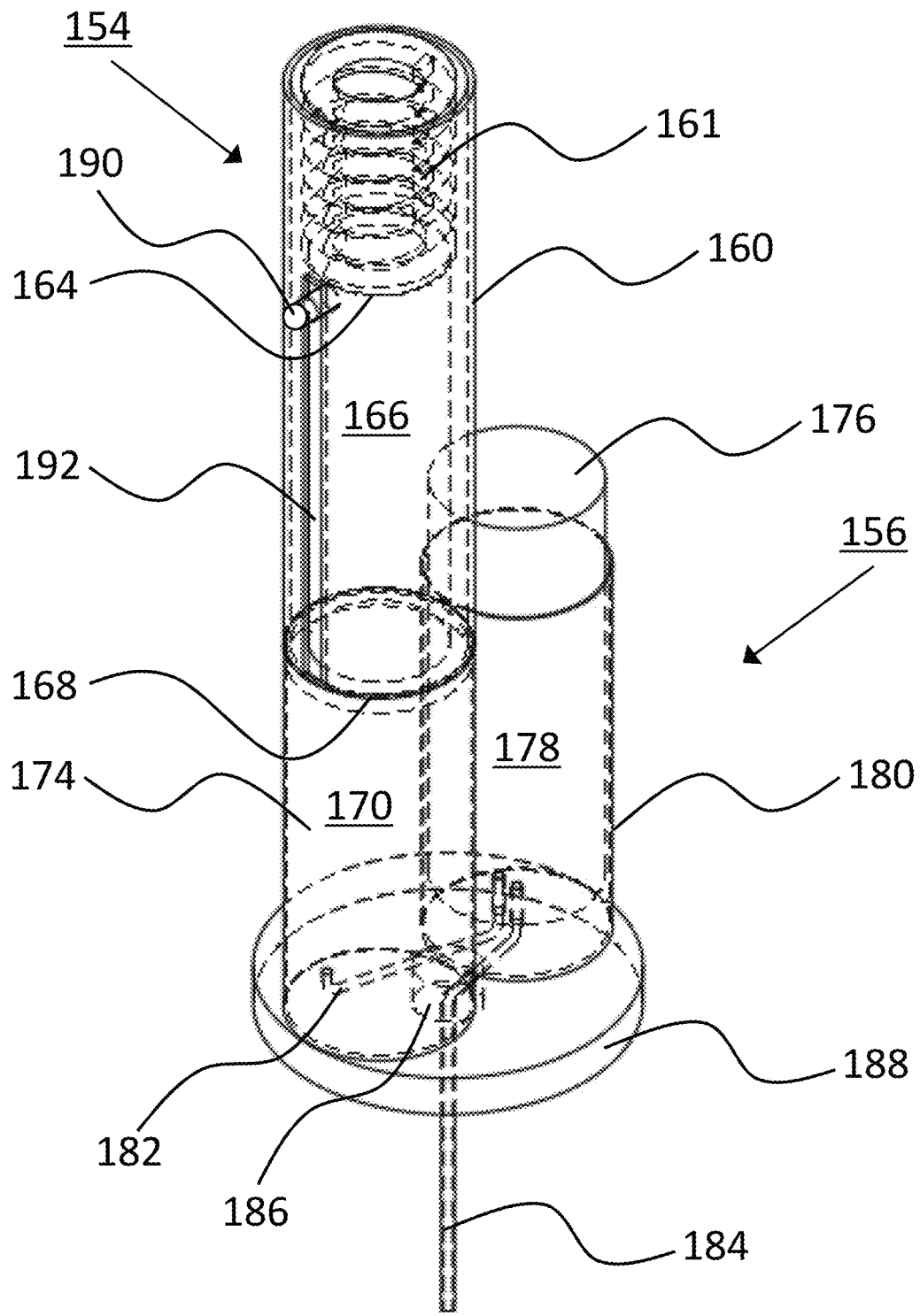
FIG. 7 is a simplified perspective view showing the sub-assembly of FIG. 5 prior to activation of the injector.
Figure 8:
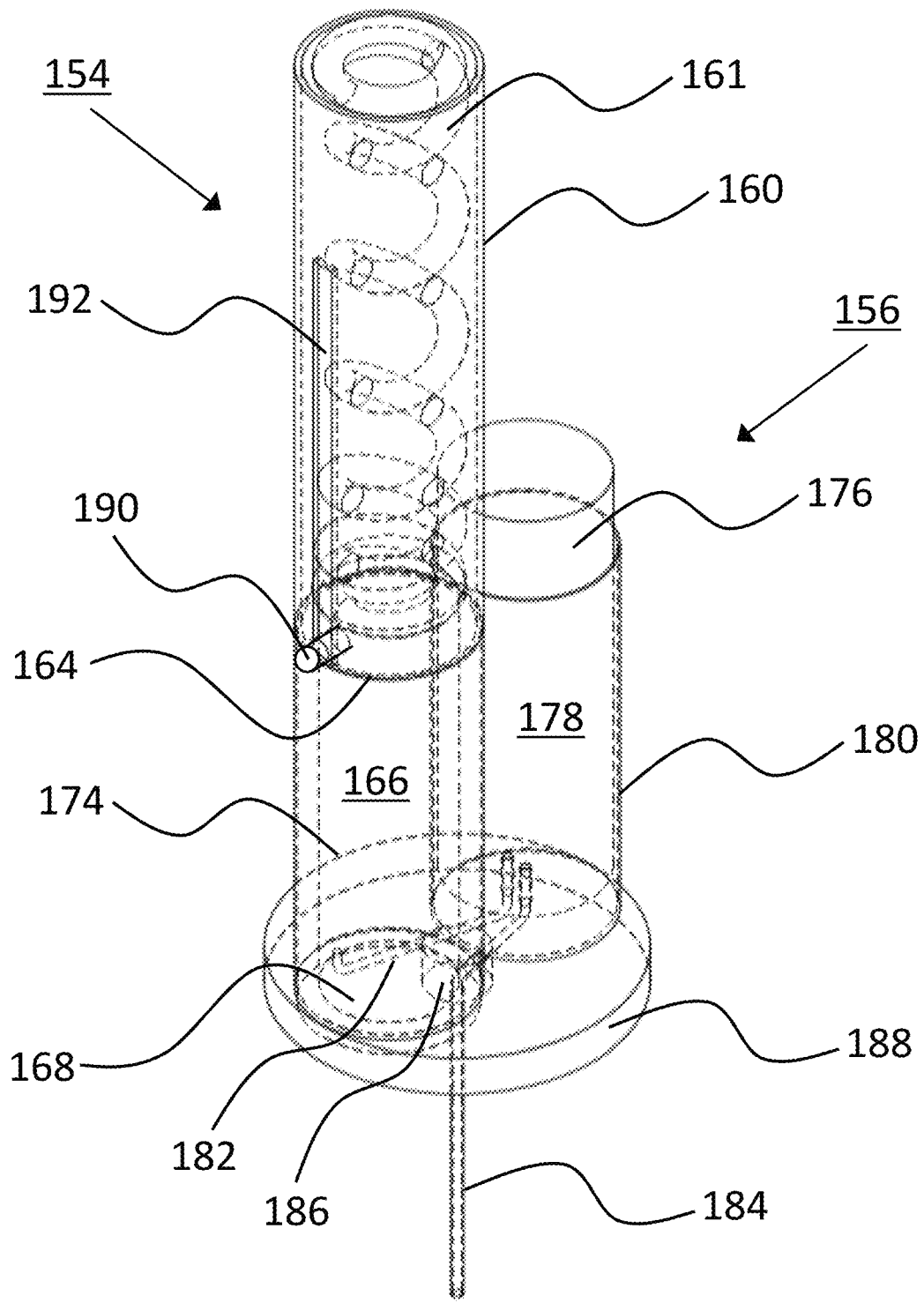
FIG. 8 is a simplified perspective view showing the sub-assembly of FIG. 5 after activation of the injector.

Now referring specifically to FIGS. 7 and 8, shown is the plunger sub-assembly 154 and the vial interface 156 before injection of the injectable substance contained in the vial 176 (FIG. 7) and after the injectable substance has been fully injected (FIG. 8). Comparing FIGS. 7 and 8, the compression spring 161 has become extended to cause the plunger member 166 to advance into the gas cylinder 170, and the second end 168 of the plunger 166 is located at the bottom of the gas cylinder 170. As discussed supra, the plunger 166 forces the gas that is initially contained in the gas cylinder 170 into the vial 176 via the first conduit 182, which in turn pressurizes the vial 176 and forces the injectable substance out of the vial 176 via the second conduit 184. The amount of gas, e.g., air, initially contained in the gas cylinder 170 is precisely calibrated to displace the full volume of the injectable substance out of the vial 176 and also out of the second conduit 184 to the not illustrated needle assembly, such that essentially no injectable substance remains in the vial 176 or second conduit 184 after injection. By precisely calibrating the amount of gas that is initially present in the gas cylinder 170 to match the internal volume 178 of the vial 176 plus the volume of the second conduit 184, it becomes possible to ensure that the auto-injector 100 has zero dead space and thereby avoid wastage of the injectable substance.

After the injectable substance has been fully injected into the subject's skin tissue, the control cylinder 120 continues to rotate and the protrusion 190 extending from the plunger member 166 continues to follow the plunger control groove 128. As shown in FIGS. 3 and 4, the plunger control groove 128 is shaped such that the plunger member 166 is returned to the initial condition shown in FIG. 7, in which the compression spring 161 is compressed and the end 164 of plunger member 166 is near the end surface of the housing 160. The action of returning the plunger member 166 to the initial condition shown in FIG. 7 has the effect of drawing air back into the gas cylinder 170 from a region above the injection site. As discussed in more detail below, when the end of the auto-injector 100 forms a seal against the subject's skin, the action of the plunger member 166 being withdrawn from the gas cylinder 170 creates a suction that results in "cupping" at the injection site. The "cupping" effect causes a mechanical shearing within the skin tissue, which aids in the distribution of the injectable substance and also aids in triggering an immune response by the subject.

Although the example auto-injector 100 described herein is configured to use e.g., a standard 2 ml vial (or up to 5 ml, or smaller than 2 ml depending on the type of injectable substance being administered) to contain the injectable substance, other alternative containers may be used instead. For instance, since injections into the skin can trigger a more robust immune response than injections into muscle tissue, and since adjuvants and other components required for intramuscular injections are not required for injections into the skin, the amount of vaccine or antigen present in the injectable substance, and the total volume of the injectable substance required, may be much smaller than 2 ml and therefore a smaller vial (e.g., 0.25 ml) may be used. Alternatively, a cartridge system may be used instead of a traditional vial. The cartridge system can have a specifically designed loading system. It is further noted that, in order to avoid accidental administration of the wrong vaccine or other medicament, the auto-injector may include safety features such as for instance keying or shaping of the housing 180 to receive only a correspondingly keyed or shaped vial/cassette etc. containing the intended vaccine or other medicament, barcode reading or blockchain technology systems etc. Accidental injection of the wrong vaccine or other medicament would therefore not be possible because the vial containing the wrong vaccine or other medicament could not be properly inserted into the housing 180.

It should also be noted that the plunger sub-assembly 154 and the vial interface 156 as described herein are provided by way of non-limiting examples only. Various modification within the capabilities of one of ordinary skill in the art are envisaged. For instance, the compression spring 161 of the plunger sub-assembly 154 may be omitted and the energy that is required to extend the plunger 166 may be provided by another suitable element such as for instance a small electrical motor.

Figure 9:
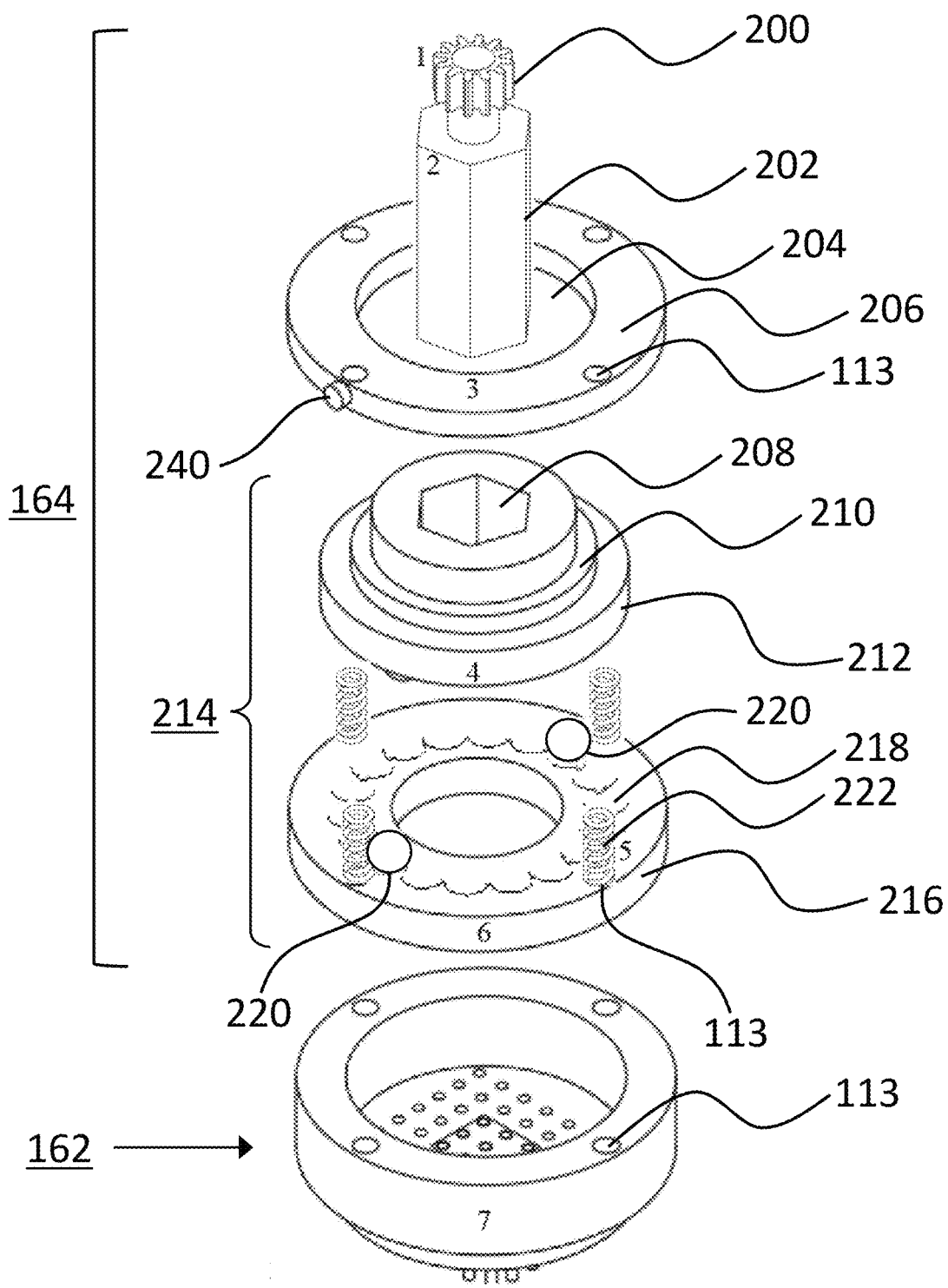
FIG. 9 is a simplified exploded view showing a needle control sub-assembly according to an embodiment.

Referring now to FIGS. 9-19, shown are different views of the needle head 162 and needle control sub-assembly 164 of a first exemplary auto-injector, and which together with the energy source and storage sub-assembly 159 make up the lower group 152 of various elements, sub-assemblies and/or assemblies shown generally in FIG. 1. In particular, FIG. 9 is an exploded view, showing the various components in the order in which they are assembled together, but in an unassembled condition. A sun gear 200, which is part of a planetary gear system of the auto-injector 100, is disposed at one end of a shaft 202. The sun gear 200 and the shaft 202 may be integrally formed, such as by a molding process, or the sun gear 200 and the shaft 202 may be separate parts that are assembled together. The sun gear 200 does not rotate relative to the shaft 202. FIG. 9 shows one possible configuration of the lower portion of the shaft 202, which in this example is generally hexagonal in a cross section taken within a plane that is normal to the length direction of the shaft 202. Alternatively, the shaft may have a cross section that is generally triangular, square, rectangular, pentagonal etc., in shape. The shaft 202 passes through a central opening 204 in a follower plate 206. A lower end of the shaft 202 is received within a complementary shaped opening 208 that is formed on an upper side 210 of an upper plate 212 of an oscillator element 214. The oscillator element 214 further comprises a lower plate 216 having an upper grooved surface 218, two spherical spacer elements 220, and a plurality of extension springs 222. When in the assembled condition, the two spherical spacer elements 220 are seated within not illustrated openings formed in the bottom side of the upper plate 212. The not illustrated openings are arranged 180° apart, such that the two spherical spacer elements 220 are positioned symmetrically onto the upper grooved surface 218 of the lower plate 216. The two spherical spacer elements 220 are e.g., metallic balls or plastic balls.

Figure 10:
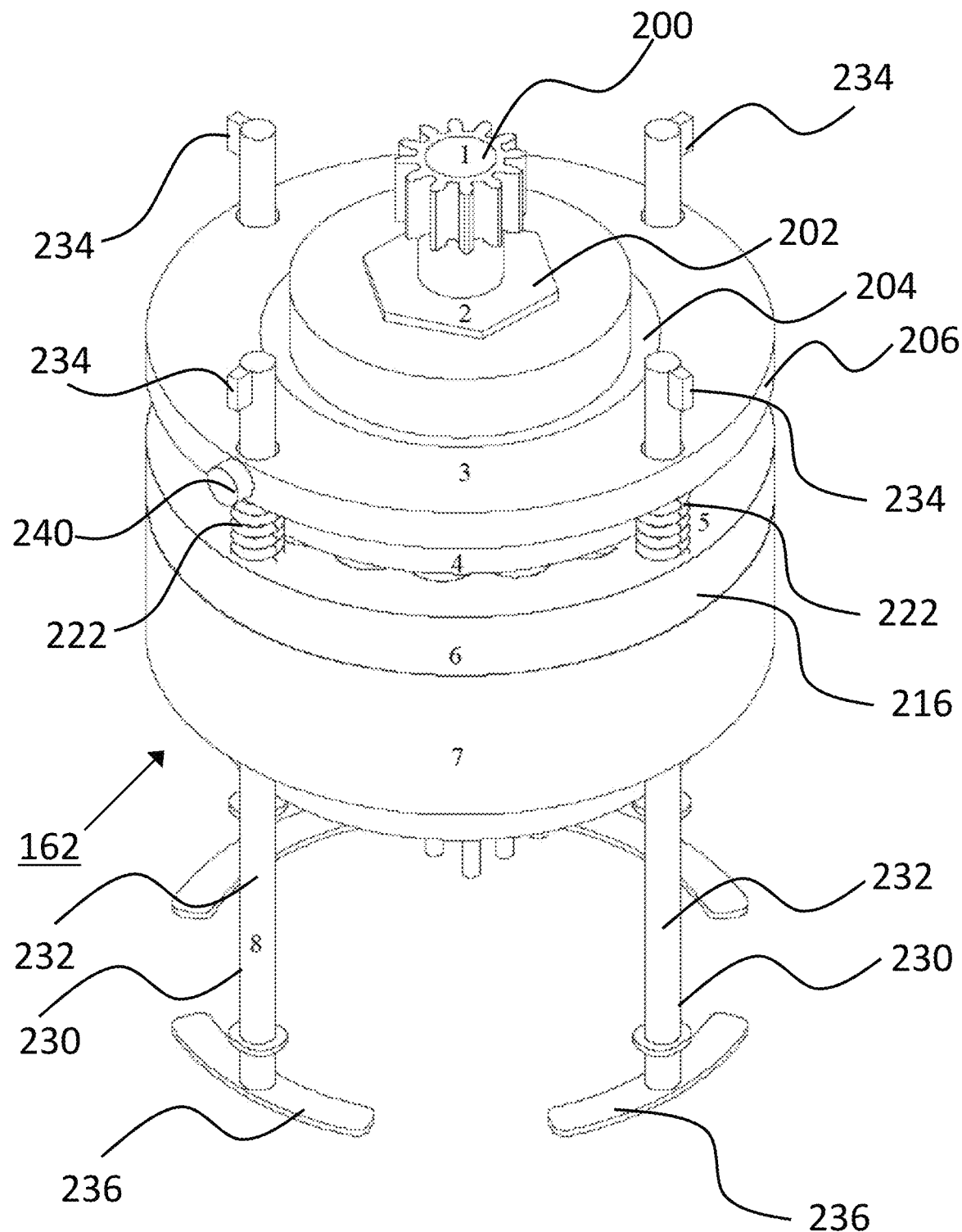
FIG. 10 is a simplified perspective view showing the needle control sub-assembly of FIG. 9 in an assembled condition.

Now referring also to FIG. 10, shown are the components of FIG. 9 in an assembled condition. FIG. 10 also shows a plurality of actuation legs 230. In the illustrated example there are four actuation legs 230, but the number of actuation legs 230 could be more than or less than four. Each actuation leg 230 has a shaft portion 232 that is configured to extend through a set of aligned openings 113 formed through the follower plate 206, the lower plate 216 of the oscillator element 214, the needle head 162, the end surface 110 of the outer housing 102, and the flange 114 of the outer housing. The shaft portions 232 prevent relative rotational movement between any of the above-mentioned elements. Also as shown most clearly in FIG. 10, the shafts 232 pass through the extension springs 222, which are disposed between the bottom side of the follower plate 206 and the upper grooved surface 218 of the lower plate 216. The upper plate 212 has a diameter that is smaller than the diameter of the follower plate 206 and of the lower plate 216. Accordingly, the upper plate 212 fits within a space between the shafts 232 and is not visible in the view that is shown in FIG. 10. Since the upper plate 212 is rigidly coupled to the shaft 202 and since the upper plate 212 is too small to be rotationally constrained by the shafts 230, any rotational motion of the shaft 202 causes corresponding rotational motion of the upper plate 212 relative to the lower plate 216 of the oscillator element 214.

Figure 11:
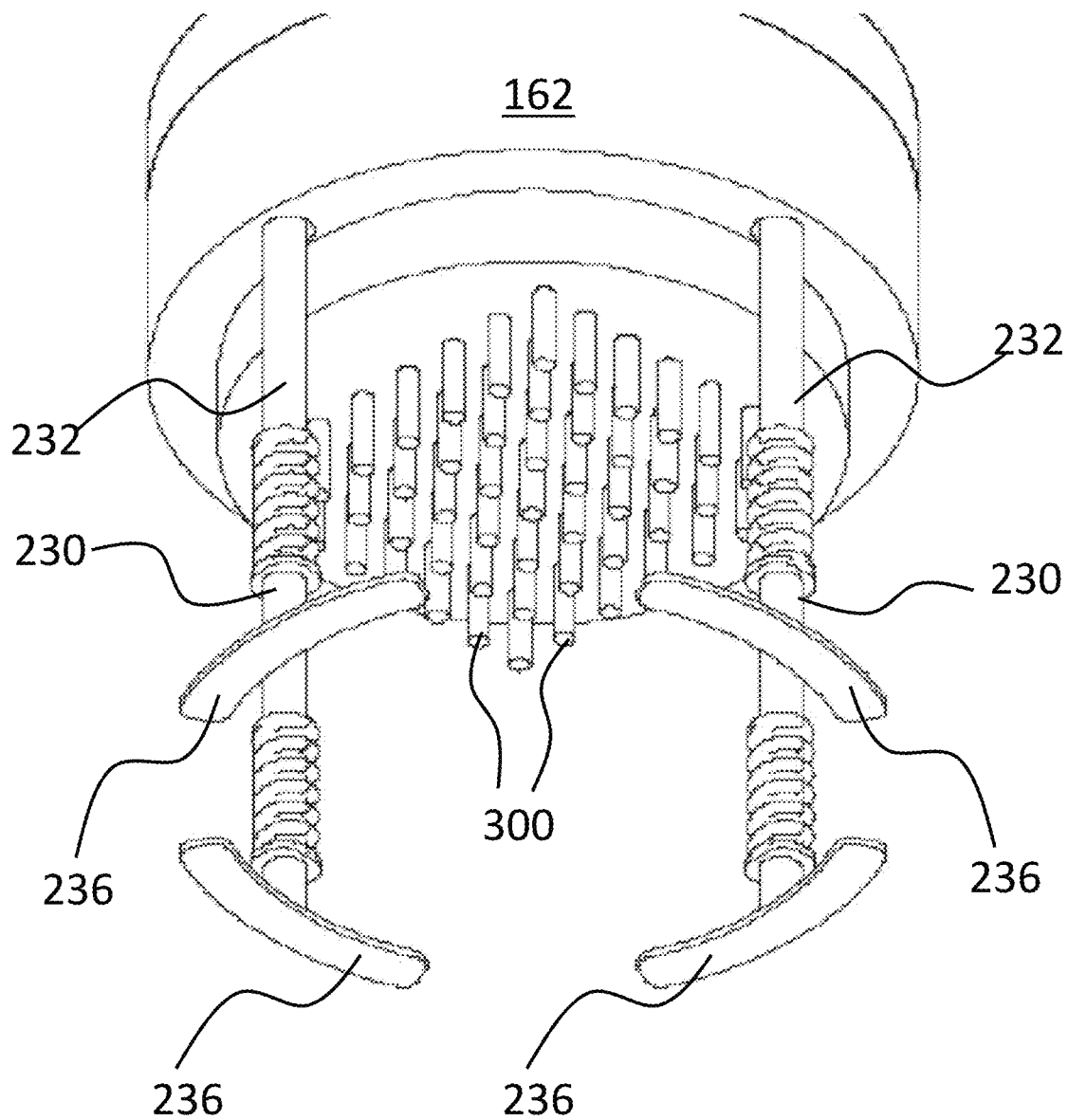
FIG. 11 is an enlarged perspective view showing one possible configuration of the needles of the needle array.

Referring now to FIG. 11, shown is a bottom perspective view of the end of the needle head 162, with four actuation legs 230 extending therefrom. The outer housing 102 and control cylinder 120 are not shown, for improved clarity. The needle head 162 includes a needle array comprising a plurality of needles 300. In this specific and non-limiting example, the needles 300 are arranged in a square array, and are distributed more-or-less symmetrically relative to a central rotational axis through the center of the needle head 162. However, other arrangements may be employed without departing from the scope of the invention.

The needles 300 may be of uniform length as shown in FIG. 11. Preferably, some of the needles are of different length than others of the needles. Providing an array of needles that includes needles of different lengths advantageously facilitates penetration of the subject's skin (avoids "bed-of-nails" effect), may compensate for slight misalignment of the auto-injector relative to the subject's skin, and allows for the injectable substance to be injected to slightly different depths within a larger volume of the subject's skin tissue. Further, the needles 300 may be of only one type, e.g., only hollow plastic needles or hollow metallic needles, or of different types, e.g., some hollow plastic needles, some hollow metallic needles and/or some solid metallic needles. The inclusion of at least some hollow and/or solid metallic needles facilitates the application of an electrical pulse to the subject's skin during electroporation.

Figure 11A:
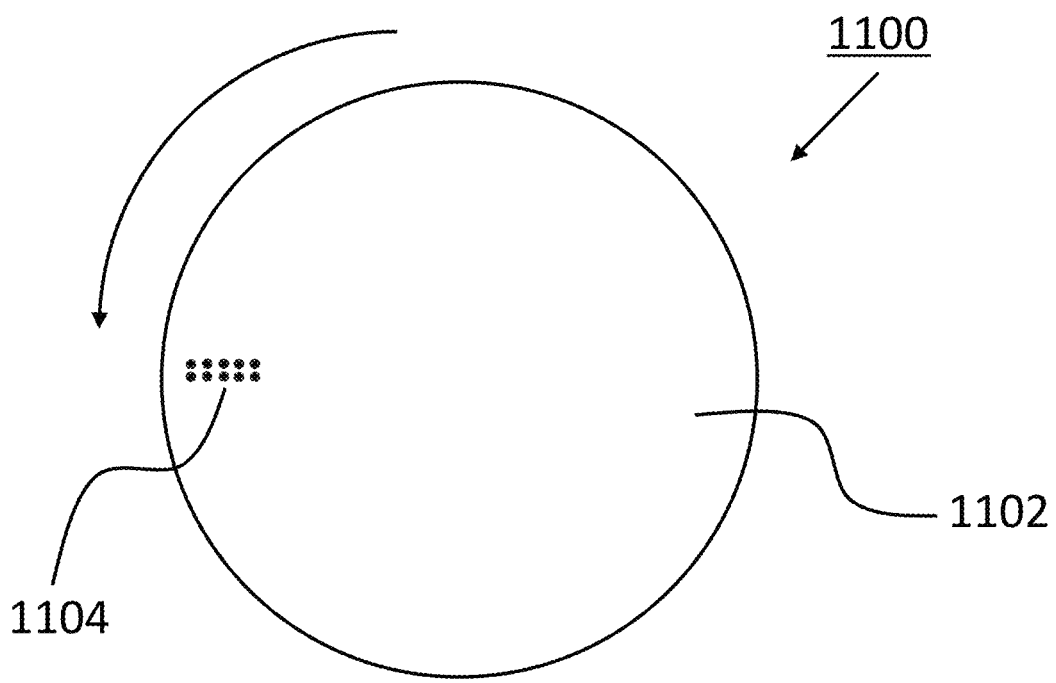
FIG. 11A is a simplified end view of a cap for being carried by a needle head, the cap having an array of needles including twelve needles arranged in two rows, optionally including both hollow and solid and/or both electrically conducting and electrically non-conducting individual needles.
Figure 11B:
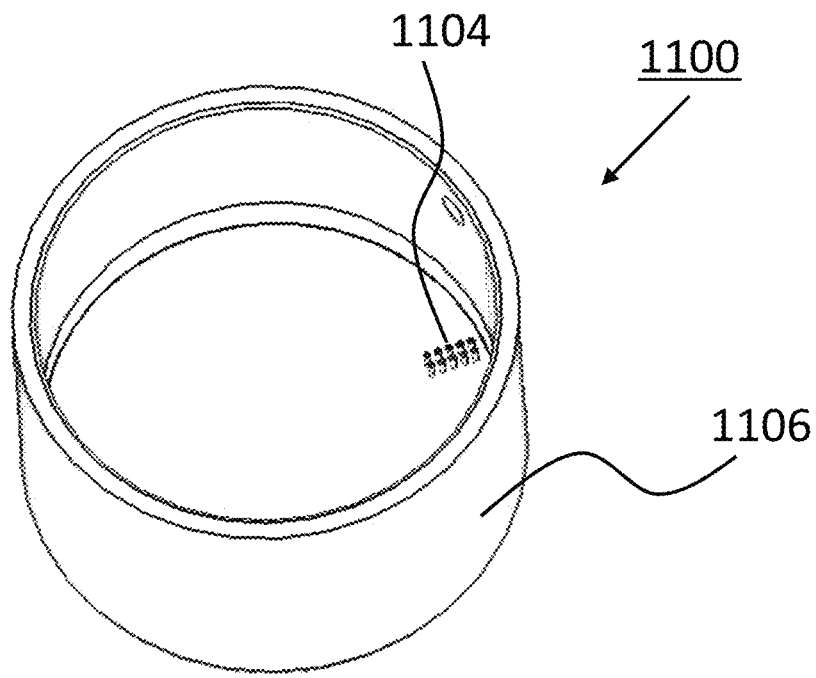
FIG. 11B is a perspective view of the cap of FIG. 11A.
Figure 11C:
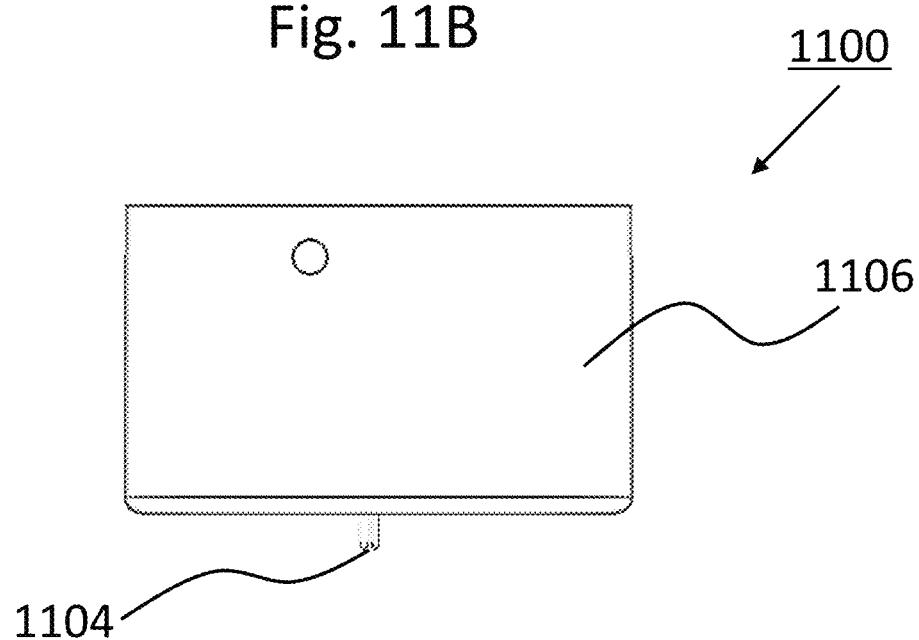
FIG. 11C is a side view of the cap of FIG. 11A.
Figure 11D:
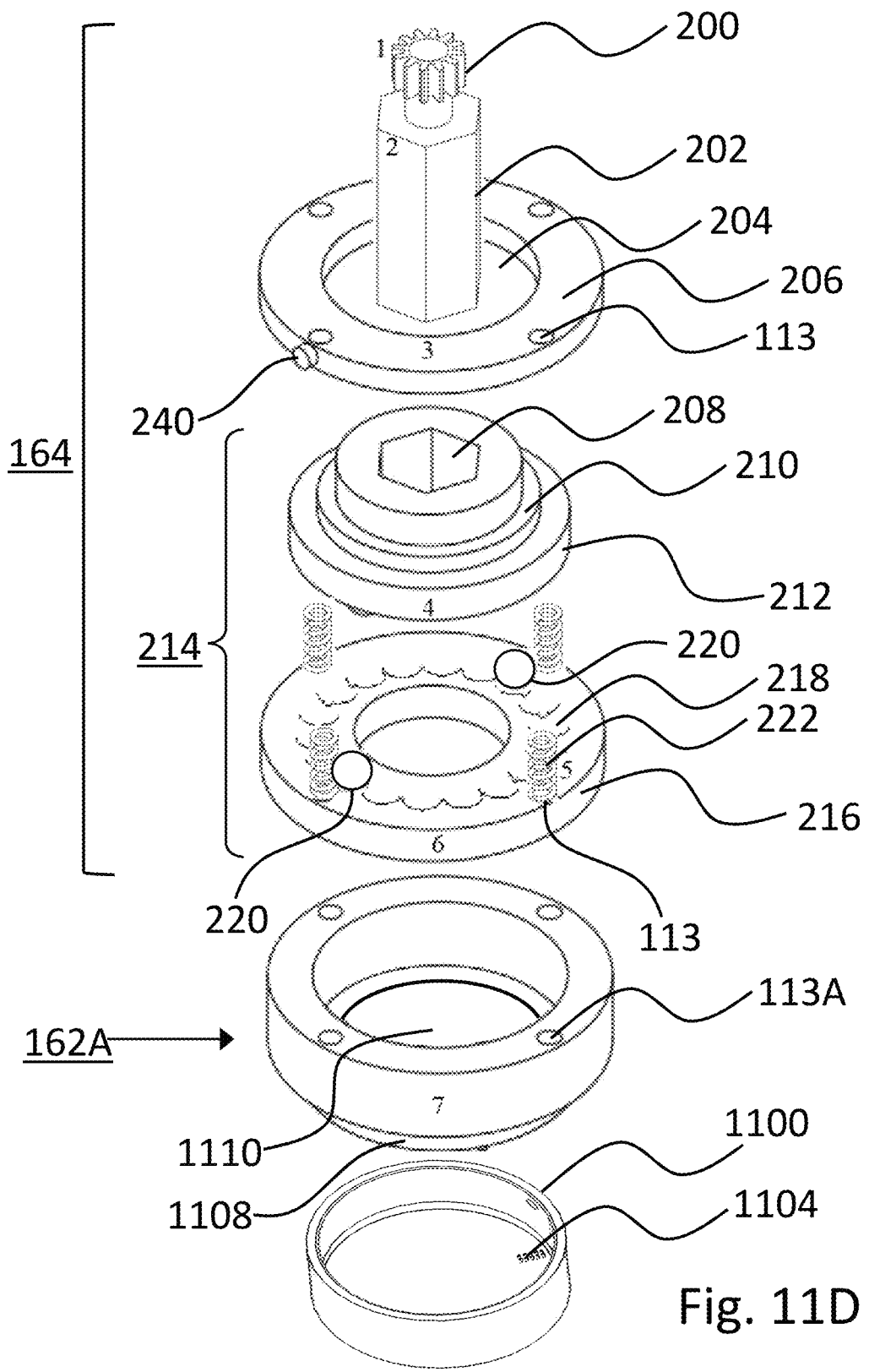
FIG. 11D is a simplified exploded view showing a needle control sub-assembly according to an embodiment in which the needle head is configured to receive a replaceable cap that carries an array of needles.

In some embodiments, the needle head 162 shown in FIG. 9 may be configured differently so as to receive a replaceable cap, such as for instance the cap 1100 that is shown in FIGS. 11A-D. As is shown in FIG. 11A, the cap 100 may have an end face 1102 with an array of needles 1104 extending therefrom, such as for instance an array of twelve needles arranged in two rows. Of course, other arrangements of the needles may be provided. As is shown most clearly in FIGS. 11B-D, the cap 1100 may be generally cup shaped with a sidewall 1106 that is sized to fit over a distal end portion 1108 of reduced diameter of the needle head 162A of FIG. 11D. Optionally, one or more sealing elements such as for instance O-rings are arranged between the outer surface of the distal end portion 1108 and the inner surface of the sidewall 1106. In the embodiment that is illustrated in FIG. 11D the needle head 162A has a central opening 1110. With the assistance of a pressurized gas, the injectable substance is provided to the array of needles 1104 via the central opening 1110 and out into the target layer of the subject's skin. Advantageously, the cap 1110 may be replaced by a new cap 1110 after injecting a predetermined number of subjects. For human subjects, the cap 1110 may be replaced by a new cap 1110 after injecting a single number of subjects. For veterinary applications, the cap 1110 may be replaced after injecting several animals or after injecting an entire herd of animals. Further advantageously, a plurality of different caps 1110 may be provided, each with different needle array configurations that are appropriate for injecting different injectable substances and/or for injecting subjects of different ages, etc.

Figure 12:
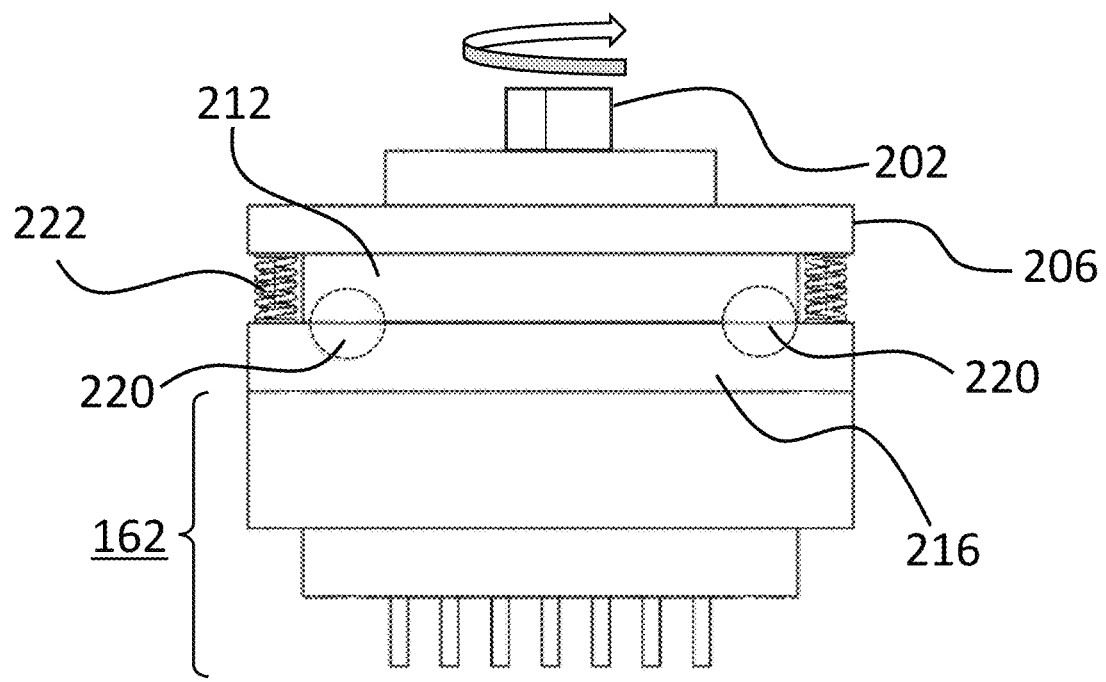
FIG. 12 is a simplified side view showing a lower portion of the needle control sub-assembly of FIG. 9 during a first portion of an oscillatory translational motion of the needle array.
Figure 13:
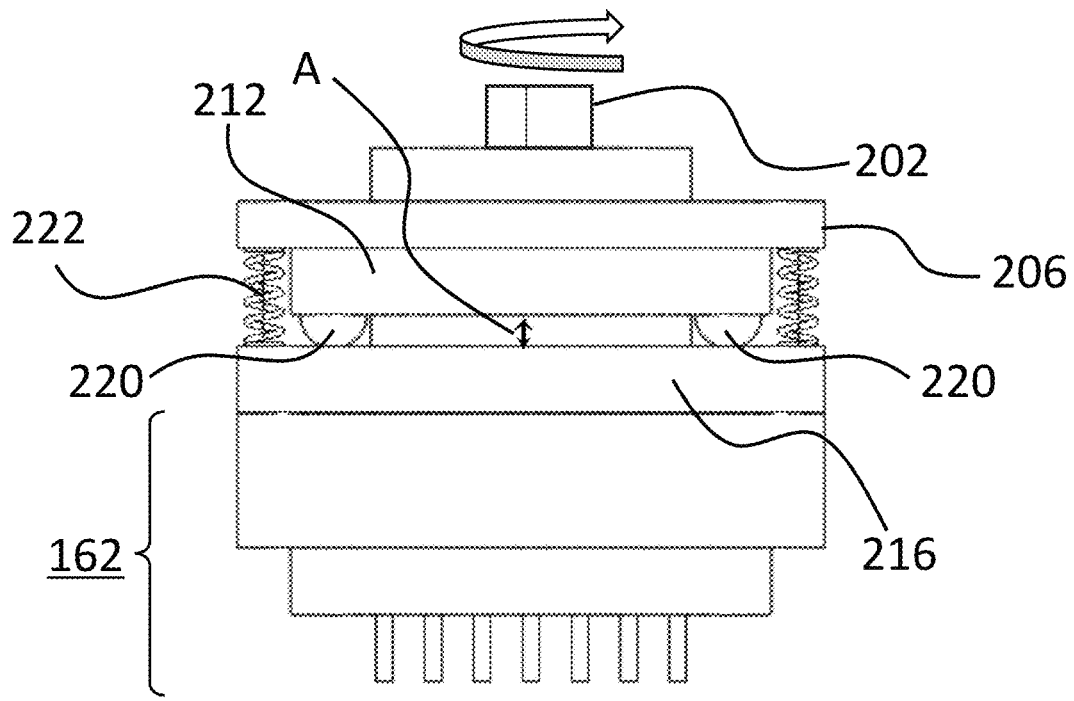
FIG. 13 is a simplified side view showing the lower portion of the needle control sub-assembly of FIG. 9 during a second portion of the oscillatory translational motion of the needle array.

Referring now to FIGS. 12 and 13, during use the upper plate 212 is caused to rotate relative to the lower plate 216 in the direction indicated by the arrows in the drawings (i.e., clockwise in this example). As the upper plate 212 rotates relative to the lower plate 216, the two spherical spacer elements 220 (shown using dotted lines in FIG. 12) that are seated in the not illustrated openings in the bottom side of the upper plate 212 are guided along a circular path around the grooved upper surface 218 of the lower plate 216, as they follow the upper plate 212. As the two spherical spacer elements 220 move along the circular path, they pass from one groove to the next along the upper grooved surface 218 of the lower plate 216. This movement of the spherical spacer elements 220 may be visualized the as spherical spacer elements 220 initially occupying a depression of one groove such that the upper plate 212 and the lower plate 216 are spaced very closely together as shown in FIG. 12, then rolling up the side of the groove to a peak and forcing the upper plate 212 and lower plate 216 away from one another as shown in FIG. 13, and then rolling down the side of the next groove to occupy the depression of the next groove such that the upper plate 212 and the lower plate 216 are once again spaced very closely together as shown in FIG. 12. The extension springs 222 act to pull the upper plate 212 and the lower plate 216 back together after they have been forced apart by the spherical spacer elements 220 passing over the peaks between respective pairs of adjacent depressions of the upper grooved surface 218.

The structural configuration of the oscillator element 214 converts the rotational motion of the shaft 202 into an oscillating translational movement of the lower plate 216 along the length direction of the auto-injector 100 relative to the upper plate 214 (as indicated by the double headed arrow "A" in FIG. 13). Since the upper plate 212 is stationary relative to the outer housing 100, the result is that the needle head 162 attached to the lower plate 216 oscillates (relative to its fully extended position) in the length direction during an injection. The oscillation rate is dependent upon at least the number of peaks and depressions formed along the upper grooved surface 218 of the lower plate 216 and the rotational rate of the upper plate 212.

The mechanism described above for producing the longitudinal oscillatory motion of the needle head 162 is merely one specific example that is suitable for use in e.g., a mechanical version of the injector 100. Other mechanisms may be envisaged for producing a similar longitudinal oscillatory motion and in some electro-mechanical embodiments a motor etc. may be used to drive the needle head 162 in this fashion.

Referring again to FIGS. 9 and 10, the follower plate 206 has a single protrusion 240 extending radially outwardly from a side edge thereof, which is used for controlling the extension and retraction of the needle head 162. When the auto-injector 100 is in the assembled condition, the protrusion 240 is received within the needle array control groove 132. During use, the control cylinder 120 rotates relative to the follower plate 206 and the protrusion 240 relatively moves within the needle array control groove 132. Some portions of the needle array control groove 132 extend only in the circumferential direction around the control cylinder 120 (see groove-portions 132a and 132c in FIGS. 14-17), which results in the needle head 162 being held at a predetermined extension position relative to the outer housing 102. Other portions of the needle array control groove 132 extend both in the circumferential direction around the control cylinder 120 and in the length direction of the along the control cylinder 120 (see groove-portions 132b and 132d), which causes the needle array of the needle head 162 to either extend from or retract into the outer housing 102.

The extension and retraction movements of the needle array 162, as controlled by the needle array control groove 132, are described in more detail below, with specific reference to FIGS. 14-17.

FIG. 14A is a simplified side view showing a portion of the auto-injector 100 proximate the needle array control groove 132. FIG. 14B is a bottom perspective view showing the position of the needles 300 of the needle array in FIG. 14A relative to the central opening 112 at the injecting end of the outer housing 102. In FIG. 14A, the protrusion 240 on the follower plate 206 is within a first groove-portion 132a of the needle array control groove 132. The first groove-portion 132a extends only in the circumferential direction around the control cylinder 120 (i.e., there is no component along the length direction of the auto-injector). As the control cylinder 120 rotates in the indicated direction, the protrusion 240 remains at the same location along the length of the control cylinder 120. As a result, the needle head 162 remains in its initial, retracted position for a predetermined length of time, which is based on the length of the first groove-portion 132a and the rotation rate of the control cylinder 120, after the auto-injector 100 is triggered. The needles 300 of the needle head 162 are initially shielded within the outer housing 102 and are set back by a safe distance from the central opening 112 at the injecting end of the outer housing. By way of a specific and non-limiting example, the needles 300 may be set back by approximately 2.5 cm from the central opening 112. This configuration reduces the risk of accidental stick injuries prior to placing the auto-injector 100 into contact with subject's skin.

Figures 15A, 15B:
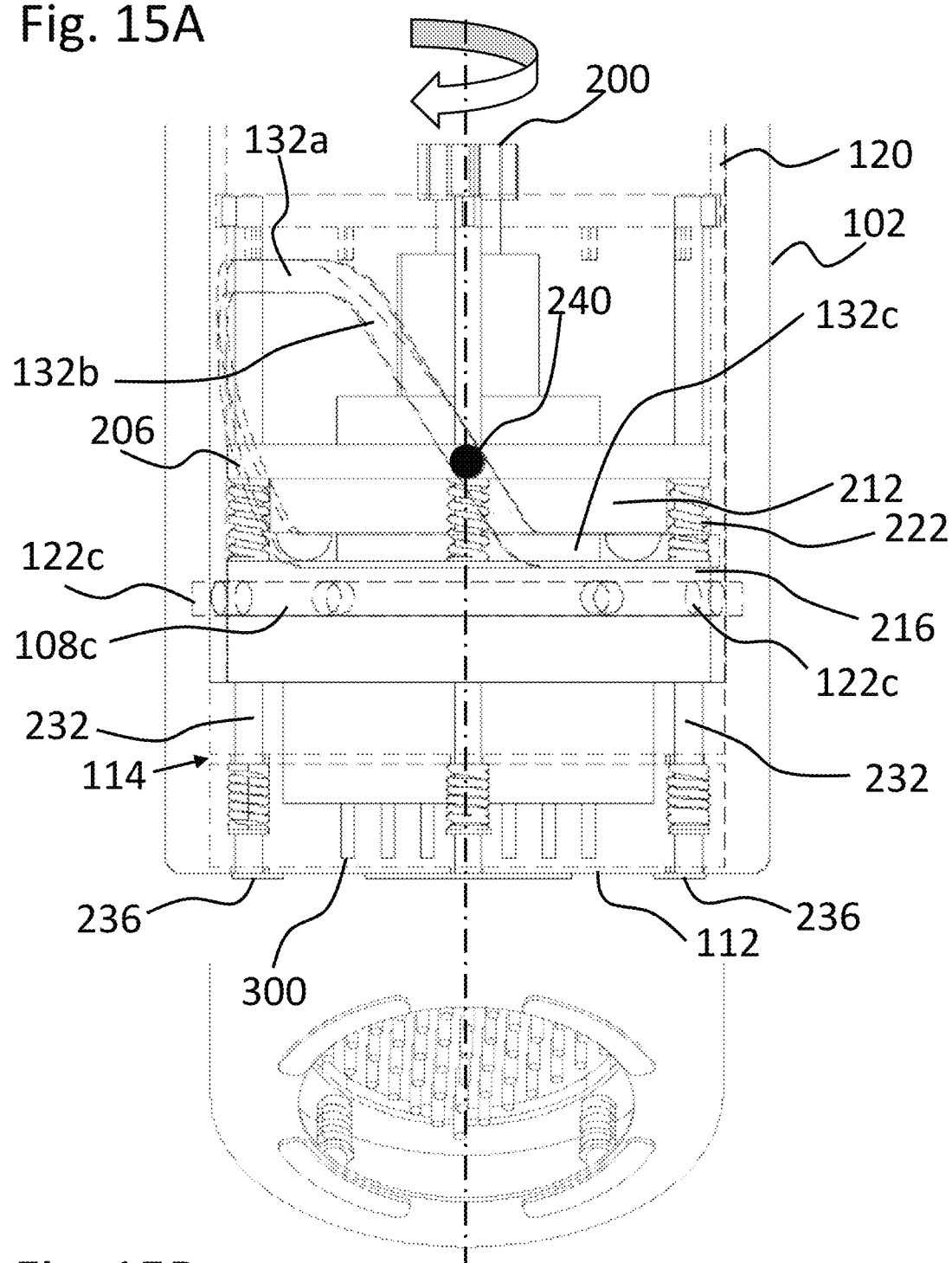
FIG. 15A is a simplified side view showing the needle control sub-assembly of FIG. 9 in a first intermediate position within the control cylinder of FIG. 3 and the external housing of FIG. 2, during the movement of the needle array toward the subject's skin.
FIG. 15B is a simplified partial bottom perspective view showing the needle control sub-assembly of FIG. 9 in the first intermediate position.

FIG. 15A is a simplified side view showing a portion of the auto-injector 100 proximate the needle array control groove 132. FIG. 15B is a bottom perspective view showing the position of the needles of the needle array in FIG. 15A, relative to the central opening 112 at the injecting end of the outer housing 102. In FIG. 15A, the protrusion 240 on follower plate 206 is within a second groove-portion 132b of the needle array control groove 132. The second groove-portion 132b extends both in the circumferential direction around the control cylinder 120 and also in the longitudinal direction along the length L of the control cylinder 120 (i.e., there is a component along the length direction of the auto-injector). When the control cylinder 120 rotates in the direction that is indicated in FIG. 15A, the needle array control groove 132 moves relative to the protrusion 240 on the follower plate 206. This relative movement causes the protrusion 240 to be displaced in the longitudinal direction, i.e., toward the injecting end of the outer housing 102. The follower plate 206 moves with the protrusion 240, which causes the follower plate 206, the oscillator element 214 and the needle head 162 to slide along the shaft portions 232 of the actuating legs 230 in the direction of the injecting end of the outer housing 102. This movement extends the needles 300 of the needle head 162 toward the central opening 112 at the injecting end of the outer housing and into contact with the subject's skin (not shown).

Figures 16A, 16B:
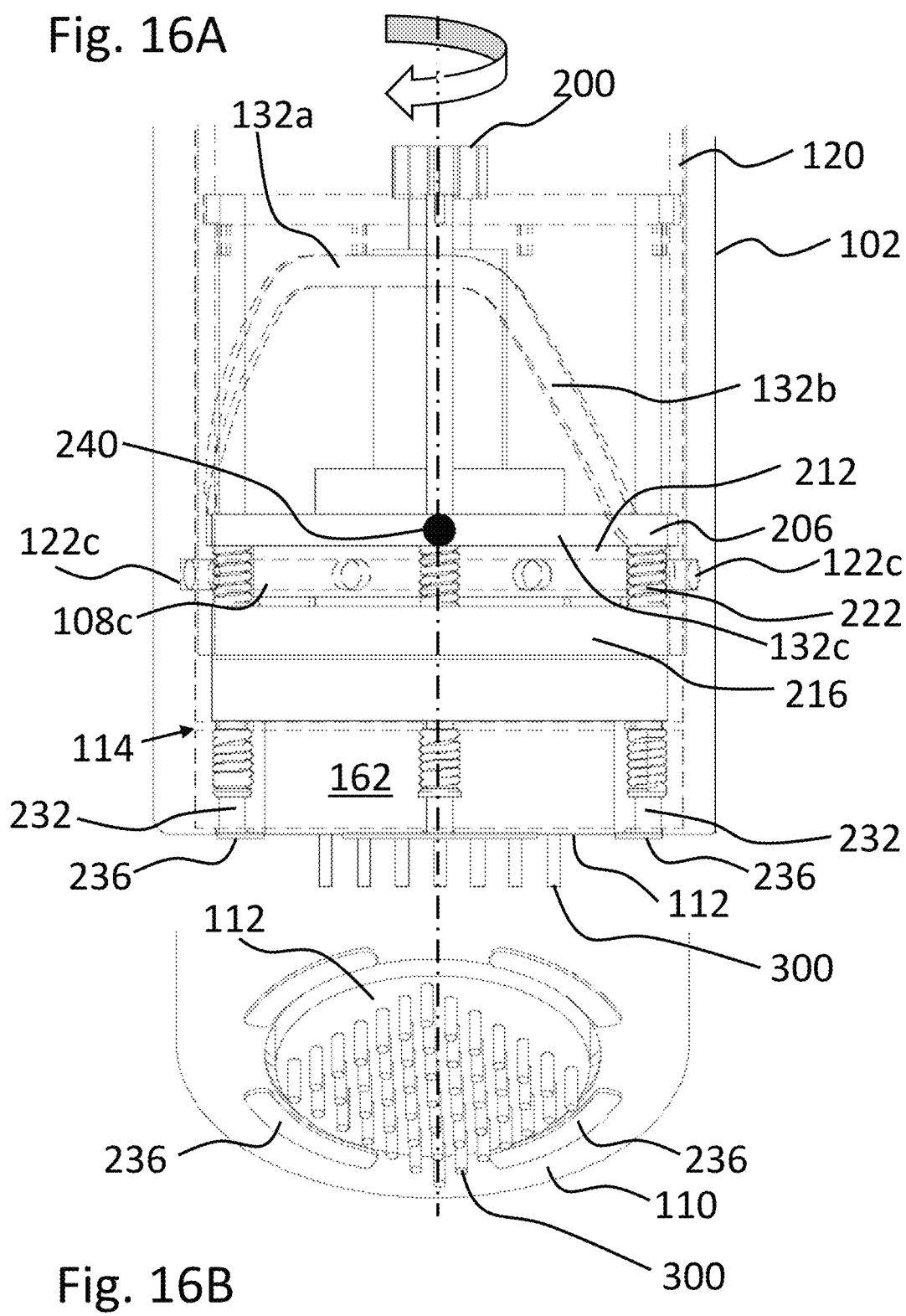
FIG. 16A is a simplified side view showing the needle control sub-assembly of FIG. 9 in a fully extended position within the control cylinder of FIG. 3 and the external housing of FIG. 2.
FIG. 16B is a simplified partial bottom perspective view showing the needle control sub-assembly of FIG. 9 in the fully extended position.

FIG. 16A is a simplified side view showing a portion of the auto-injector 100 proximate the needle array control groove 132. FIG. 16B is a bottom perspective view showing the position of the needles of the needle array in FIG. 16A, relative to the central opening 112 at the injecting end of the outer housing 102. In FIG. 16A, the protrusion 240 on the follower plate 206 is within a third groove-portion 132c of the needle array control groove 132. The third groove-portion 132a extends only in the circumferential direction around the control cylinder 120 (i.e., there is no component along the length direction of the auto-injector). As a result, the needle head 162 remains in the extended position for a predetermined length of time, which is based on the length of the third groove-portion 132c and the rotation rate of the control cylinder 120. The needles 300 of the needle array penetrate into the subject's skin (not shown) during this time and undergo the oscillatory translational movement that is induced by the oscillator element 214. Also, during this time, the injectable substance is injected into the subject's skin tissue via at least some of the needles 300 of the needle array. The oscillatory translational movement, when present, may cause the needles 300 of the needle array to repeatedly penetrate into and withdraw out of the subject's skin tissue. During this oscillatory translational movement, the needles 300 may also be moved in a direction that is substantially parallel to the surface of the subject's skin, such as for instance via a rectilinear or curvilinear translational movement of the needles 300, such that at least some of the needles 300 penetrate a portion of the subject's skin that was not penetrated previously, and which results in the injectable substance being injected into a larger volume of the subject's skin tissue.

Figures 17A, 17B:
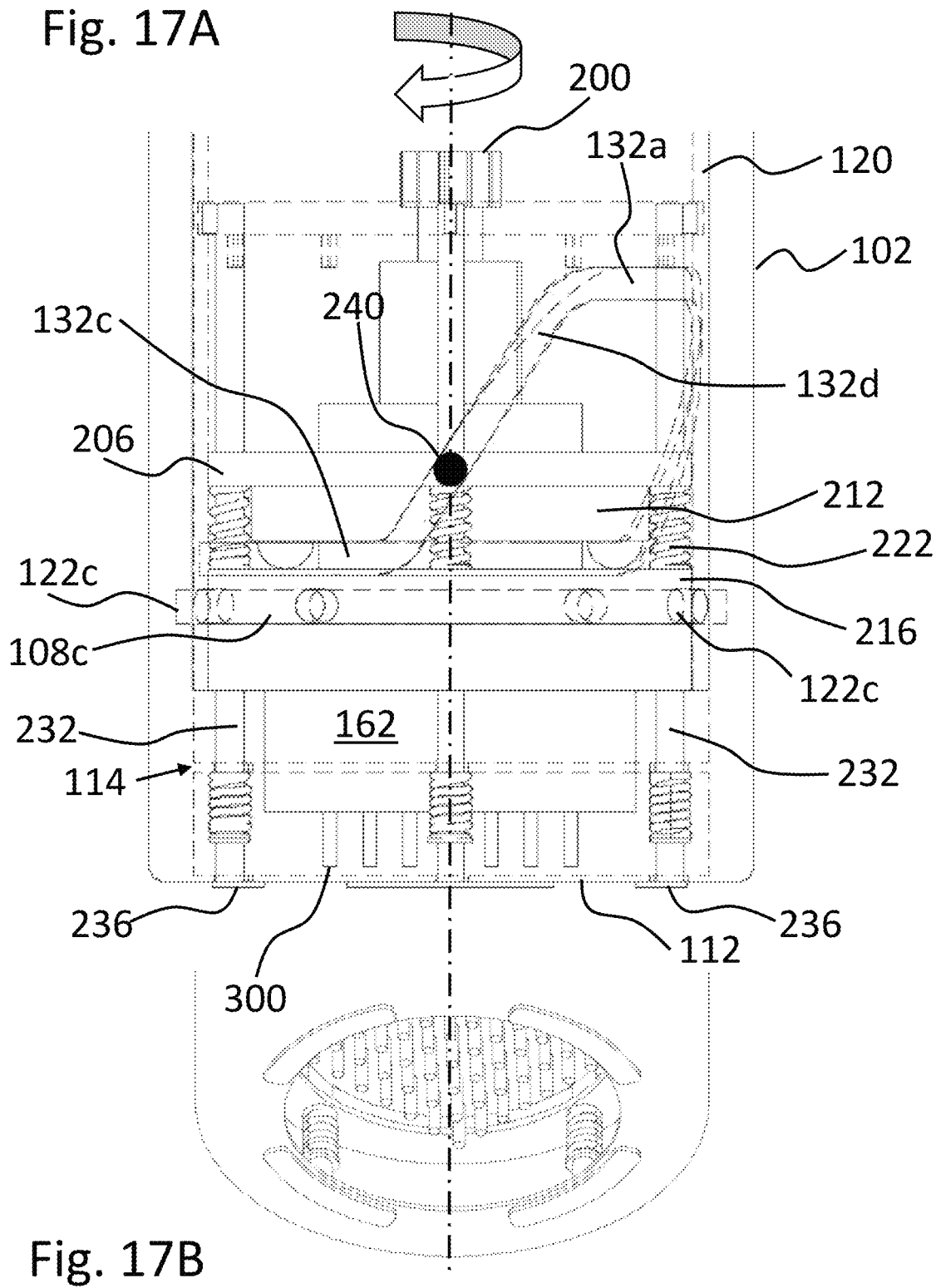
FIG. 17A is a simplified side view showing the needle control sub-assembly of FIG. 9 in a second intermediate position within the control cylinder of FIG. 3 and the external housing of FIG. 2, during movement of the needle array away from the subject's skin.
FIG. 17B is a simplified partial bottom perspective view showing the needle control sub-assembly of FIG. 9 in the second intermediate position.

FIG. 17A is a simplified side view showing a portion of the auto-injector 100 proximate the needle array control groove 132. FIG. 17B is a bottom perspective view showing the position of the needles of the needle array in FIG. 17A, relative to the central opening 112 at the injecting end of the outer housing 102. In FIG. 17A, the protrusion 240 on follower plate 206 is within a fourth groove-portion 132d of the needle array control groove 132. The fourth groove-portion 132d extends in both the circumferential direction around the control cylinder 120 and also in the longitudinal direction along the length L of the control cylinder 120 (i.e., there is a component along the length direction of the auto-injector). When the control cylinder 120 rotates in the direction that is indicated in FIG. 17A, the needle array control groove 132 moves relative to the protrusion 240 on the follower plate 206. This relative movement causes the protrusion 240 to be displaced in the longitudinal direction, away from the injecting end of the outer housing 102. The follower plate 206 moves with the protrusion, which causes the follower plate 206, the oscillator element 214 and the needle head 162 to slide along the shaft portions 232 of the actuating legs 230 in the direction away from the injecting end of the outer housing 102. This movement retracts the needles 300 of the needle head 162 back through the central opening 112 at the injecting end of the outer housing and out of contact with the subject's skin (not shown). The needles 300 of the needle head 162 are returned substantially to their initial, retracted position by the time the rotation of the control cylinder 120 stops. By way of a specific and non-limiting example, the needles 300 may be retracted back approximately 2.5 cm from the central opening 112. This configuration reduces the risk of accidental stick injuries after the auto-injector 100 has been used to perform an injection.

The relative shapes of the plunger control groove 128 and of the needle array control groove 132 cooperate to define the timing of the various steps of the injection. The shapes of the grooves are designed such that the needles of the needle head 162 are properly extended from the outer housing 102 and the needles of the needle head are at the correct depth within the subject's skin before the vaccine is transferred from the vial 176 to the needles 300 of the needle head 162 via the second conduit 184. The shapes of the grooves must also account for the delay between depressing the plunger and the vaccine arriving at the needles 300 of the needle head 162. In some embodiments, the plunger control groove 128 includes an intermediate portion that extends only circumferentially around the control cylinder 120. In such embodiments, a first part of the plunger control groove 128 causes partial depression of the plunger element 166 to move the injectable substance out of the vial 176 and through the second conduit 184 to the needles of the needle head 162. The intermediate portion of the plunger control groove 128 then pauses the plunger movement until the needle head 162 is positioned correctly and the needles 300 have penetrated the subject's skin to the desired depth. Finally, a second part of the plunger control groove 128 causes the plunger element 166 to be completely depressed, thereby injecting the full volume of the injectable substance that was originally in vial 176 into the tissue of the subject. As will be apparent, modifying the shapes and/or number of the grooves that are formed along the inner surface 126 of the control cylinder 120 allows different timings of different operations to be programmed to suit different applications.

In some embodiments, the initial, retracted position of the needles 300 may be much closer to the central opening 112 at the injecting end of the outer housing 102 than in the example that is illustrated in FIGS. 14A and 14B. For instance, the needles 300 may be set back by approximately 0 mm to approximately 10 mm from the central opening 112 and in some embodiments the needles 300 may be set back by approximately 0 mm to approximately 5 mm from the central opening 112. When the needles are set back from the central opening 112 by smaller distances, such as 0 mm to 10 mm or 0 mm to 5 mm, then the shape of the needle array control groove 132 is configured to produce a suitably smaller extension of the needles 300 of the needle head. Similarly, the shape of the plunger control groove 128 is configured to cooperate to define the timing of the various steps of the injection, as discussed above. In certain embodiments in which the initial, retracted position of the needles 300 is close to or within a plane of the central opening 112, a cap or other removable protective element may be provided to prevent stick-injuries. In at least some of these embodiments, the oscillator element 214 may be omitted and the needle array control groove may be configured to cause the needles 300 to be extended into the subject's skin and then subsequently retracted out of the subject's skin a single time, or multiple times, such as for instance two times, three times, four times, etc. Movement of the needles 300 may also occur, approximately within the plane of the central opening, after retracting the needles from the subject's skin or even while the needles are within the subject's skin. Such movement of the needles 300 results in injection of the injectable substance into a larger volume of skin tissue and results in more damage so as to enhance the body's natural immune response at the injection site. Optionally, the needles 300 are withdrawn further back from the central opening 112 after the injection has been completed, thereby reducing the risk of stick-injuries without requiring the user to replace a protective cap.

Figure 18:
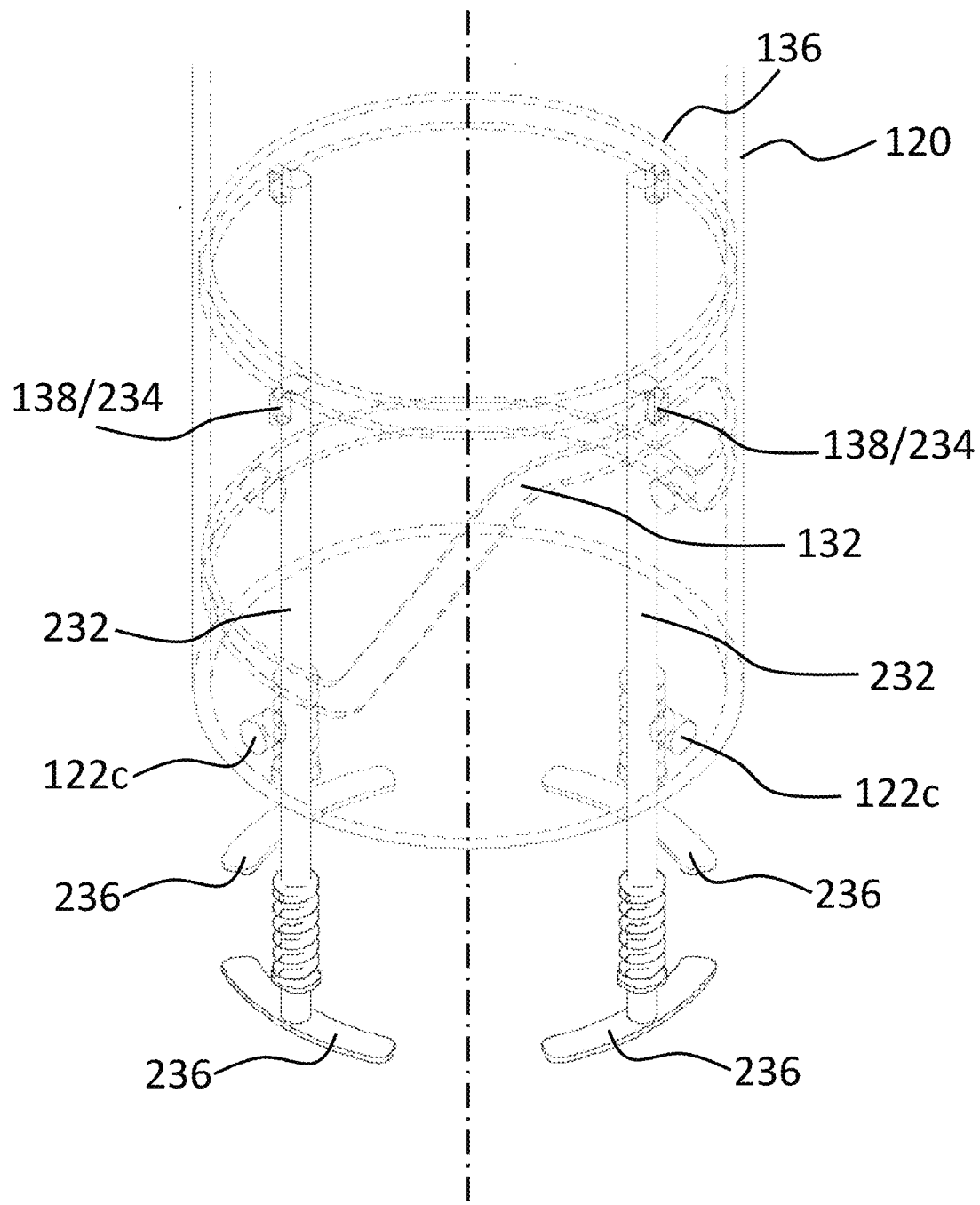
FIG. 18 shows details of the trigger mechanism components.
Figure 19:
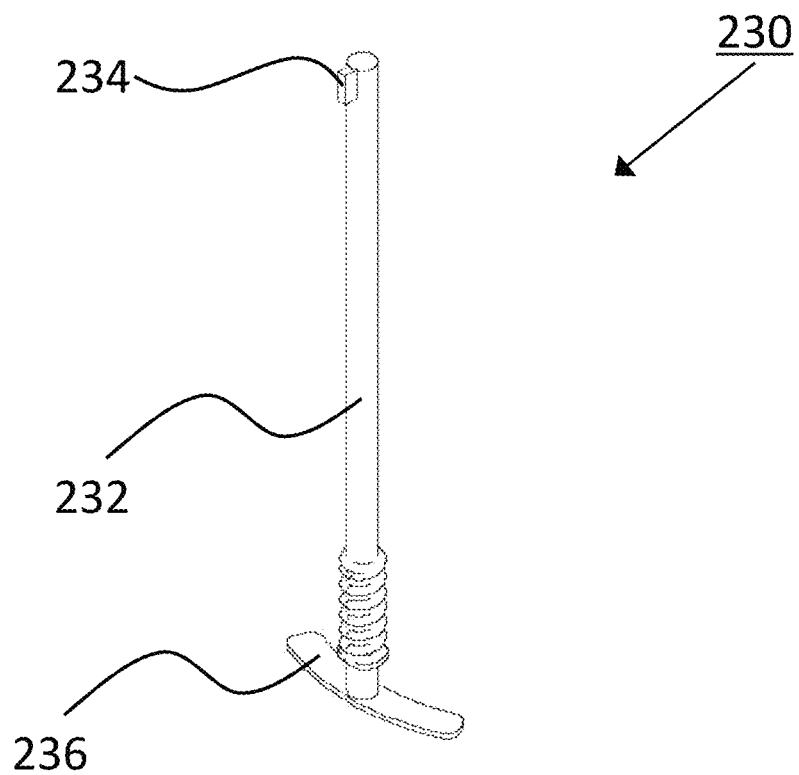
FIG. 19 is a simplified perspective view of one of the trigger and guide legs.

Now referring again to FIG. 10 and also to FIGS. 18 and 19, each of the plurality of actuation legs 230 further includes a protrusion 234 that is oriented to extend generally radially outward from the longitudinal axis of the auto-injector 100, in the assembled condition. Each protrusion 234 is shaped to be received in one of the notches 138 that opens into the trigger mechanism control slot 136 along the inner surface 126 of the control cylinder 120. When the protrusions 234 are retained in a respective one of the notches 138, the control cylinder 120 is prevented from rotating relative to the outer housing 102 or relative to the various internal components, sub-assemblies and/or assemblies that are housed within the control cylinder 120. In this condition, the auto-injector 100 is locked in its initial condition and is ready to be triggered to inject an injectable substance.

For improved clarity, FIG. 19 shows a single actuation leg 230 in isolation. As described above, the actuation leg 230 has a shaft 234 along which the follower plate 206, the oscillator element 214 and the needle head 162 slide during the extension and retraction movements. The shaft 234 also passes through the openings 113 in the end surface 110 and flange 114 of the outer housing 102, which prevents relative rotational movement between the follower plate 206, the oscillator element 214, the needle head 162 and the outer housing 102. Triggering of the auto-injector 100 is achieved, in this specific and non-limiting example, by placing the "feet" 236 at the bottom end of the actuation legs 230 into contact with the skin surface of the subject and pressing downwardly on the auto-injector 100. This causes the actuation legs to move upwardly such that the protrusions 234 move out of the notches 138 and enter into the trigger mechanism control slot 136 along the inner surface 126 of the control cylinder 120. The control cylinder 120 then becomes "unlocked" and can begin to rotate relative to the outer housing 102 and relative to the various components, sub-assemblies and/or assemblies that are housed within the control cylinder 120.

Figure 20:
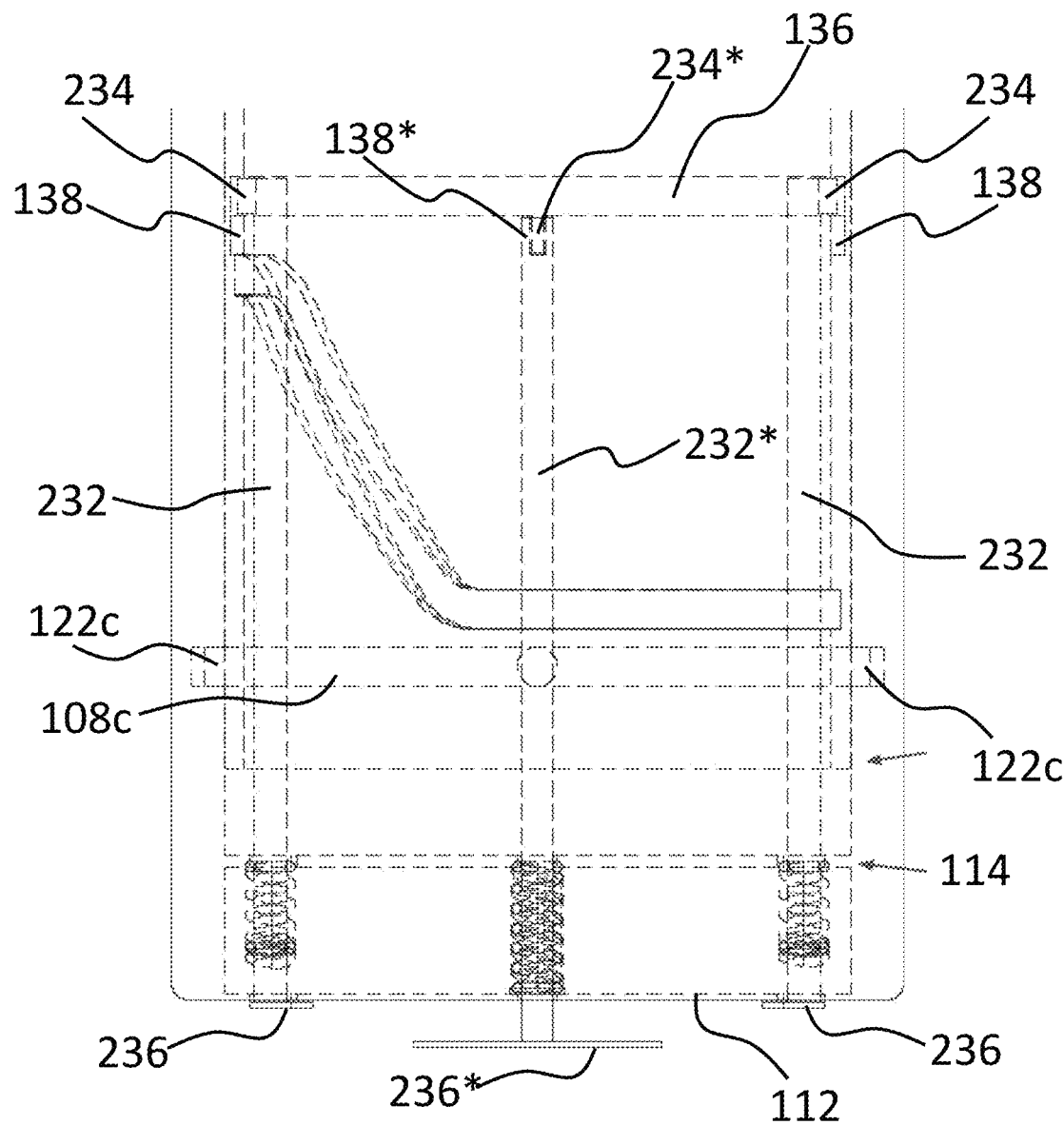
FIG. 20 shows detail of the trigger mechanism in a mis-aligned and non-triggered condition.

FIG. 20 shows the injecting end of the auto-injector 100 when the auto-injector is incorrectly positioned against the subject's skin. Since one of the feet 236* is not correctly contacting the subject's skin, the shaft 234* does not move upwardly into the auto-injector 100 and the protrusion 234* therefore remains seated within the notch 138* and does not enter into the trigger mechanism control slot 136. The protrusion 234* prevents the rotatable control cylinder 120 from rotating when the auto-injector 100 is incorrectly positioned against the subject's skin, thereby ensuring that the injection occurs only when the auto-injector 100 is correctly positioned for delivering the injectable substance to the target depth within the subject's skin.

Although the feet 236 are shown as separate elements at the end of the respective shafts 234 of the actuation legs 230, in some embodiments the feet 236 are joined to form a continuous contact surface encircling the central opening 112. The material forming the contact surface is preferably sufficiently flexible to allow the shafts 234 to move independently of one another, which is necessary to prevent triggering when the auto-injector 100 is positioned incorrectly. If a rigid material is used to form the contact surface in this alternative implementation, then the shafts may only move as a unit and the auto-injector may be triggered even when not positioned correctly on the subject's skin.

Figure 20A:
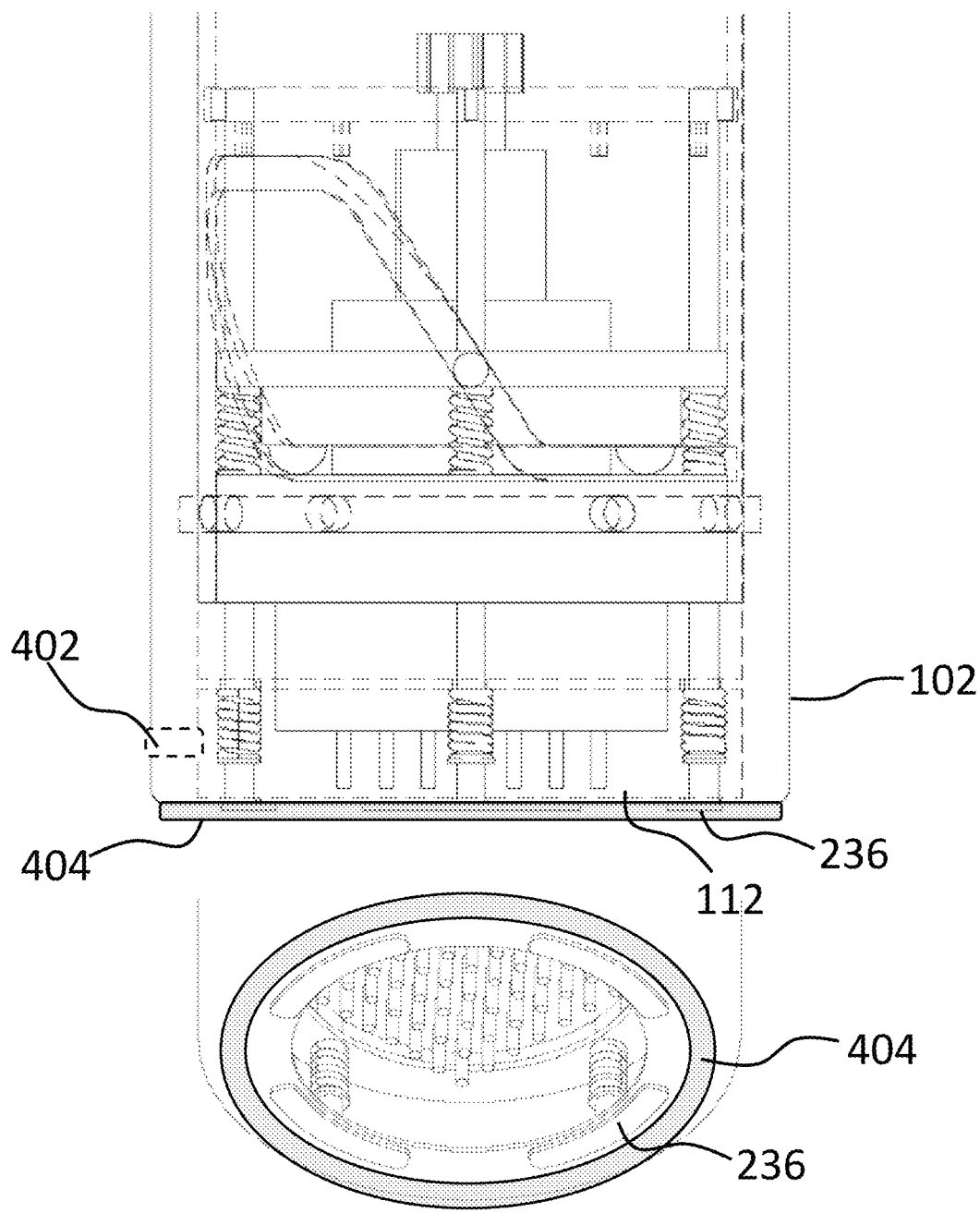
FIG. 20A shows detail of a gasket or skirt at the injecting end of the auto-injector.

In at least some embodiments, means for sealing the injecting end of the auto-injector against the subject's skin is provided. One possible implementation of the means for sealing is shown in FIG. 20A. In this example, a skirt or gasket 404 is arranged at the injecting end of the outer housing 102. The skirt or gasket 404 is fabricated e.g., from silicone or another suitably deformable material. The skirt or gasket 404 extends from the injecting end of the outer housing 102 and forms a substantially gas-tight seal against the subject's skin, whilst still allowing the feet 236 of the actuating legs 230 to engage the subject's skin for triggering the auto-injector 100. Optionally, a one-way valve 402 is provided e.g., through the outer housing 102, to allow air within the region above the injection site to escape during extension of needles of the needle head 162 through the central opening 112.

Figure 21:
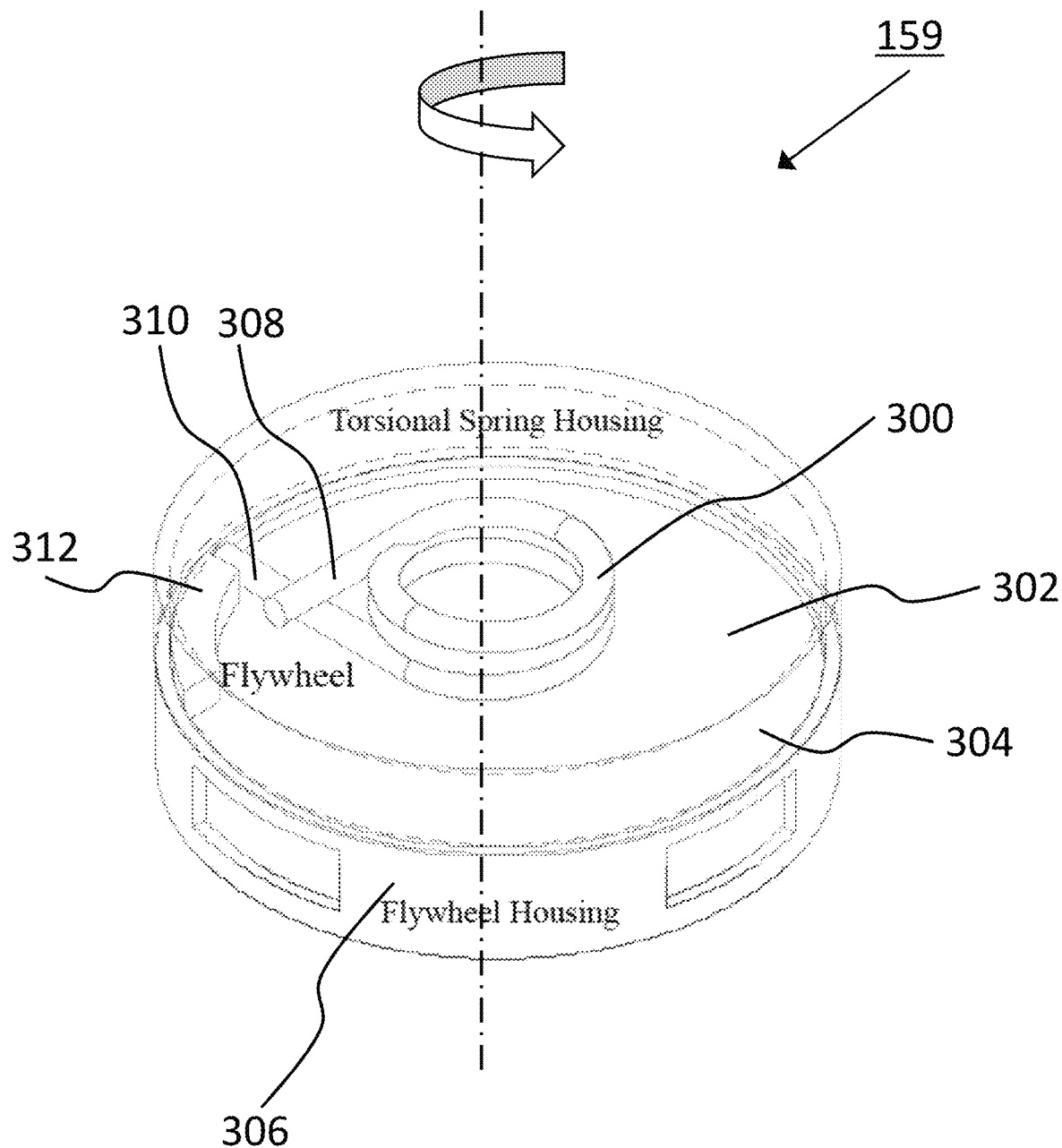
FIG. 21 is a simplified perspective view showing the arrangement of the torsion spring and flywheel disposed within respective housings.

Referring now to FIG. 21, shown is an example energy source and storage sub-assembly 159 for providing and storing the energy that is needed to rotate the control cylinder 120, which controls the movements of the plunger member 166 and needle head 162, and to rotate the upper plate 220 of the oscillator element 214. In this specific and non-limiting example, a torsion spring 300 stores mechanical potential energy, which when released is used to spin up a flywheel 302, which in turn stores rotational kinetic energy to be used during an injection operation to rotate the control cylinder 120 and upper plate 220. However, in an alternative (electro-mechanical) embodiment, the energy source and storage sub-assembly 159 may include an electric motor and a DC power supply or an AC power supply. The torsion spring 300 is contained within a torsion spring housing 304 and the flywheel 302 is contained within a flywheel housing 306. Optionally, the torsion spring housing 304 and flywheel housing 306 are replaced with a single housing that contains both the torsion spring 300 and the flywheel 306. The torsion spring housing 304 is mounted below the support base or plate 188 that was described with reference to FIGS. 5-8. Optionally, the support base or plate 188 performs a dual function and also serves as the torsion spring housing 304.

Referring still to FIG. 21, the torsion spring 300 has a fixed end 308, which is rigidly coupled to e.g., a not illustrated top surface of the torsion spring housing 304. The torsion spring 300 also has a free end 310. Prior to triggering the auto-injector 100, the free end 310 of the torsion spring 300 is held back by a ledge or protrusion 312 along the top of the flywheel 302. As is described in more detail below, the flywheel 302 is coupled to the control cylinder 120 via a planetary gear system (shown in FIGS. 23-25). Since the control cylinder 120 is initially "locked" by the protrusions 234 of the actuation legs 230 being seated within the notches 138 of the trigger mechanism control slot 136, the flywheel 302 is also initially "locked" and therefore prevented from rotating. When the auto-injector 100 is triggered, the protrusions 234 of the actuation legs 230 move out of the notches 138 and the control cylinder 120 is free to rotate. The flywheel 302 is no longer prevented from rotating, and the free end 310 of the torsion spring 300 begins to push the ledge or protrusion 312 extending from the top of the flywheel 302 in a circular direction (counter clockwise in FIG. 21).

Figure 22A:
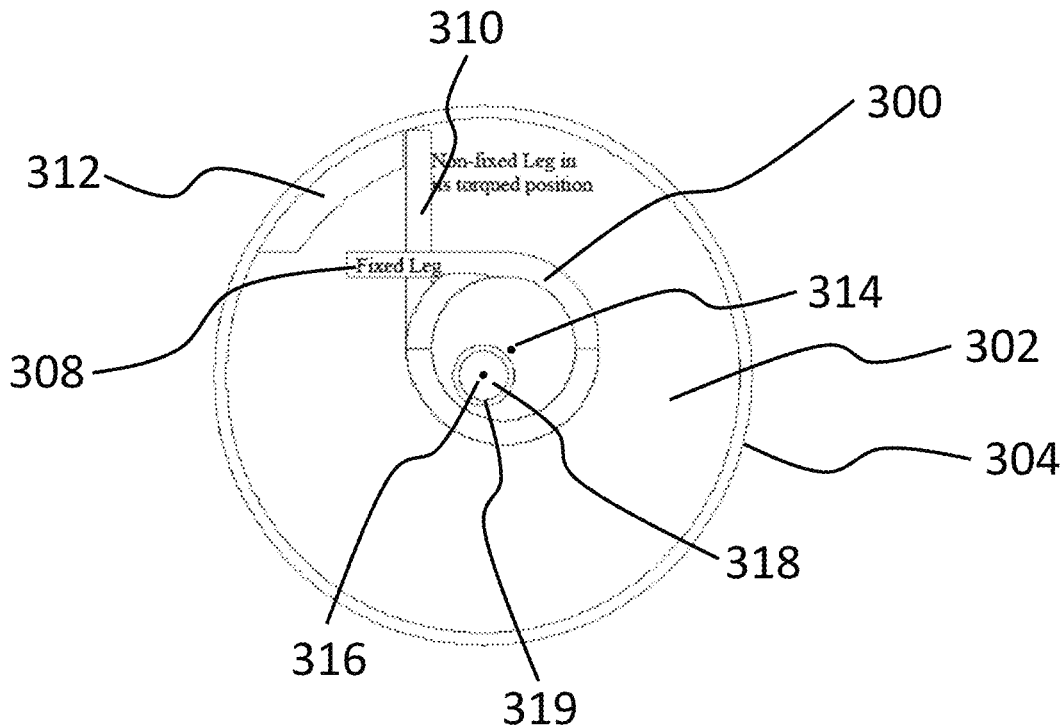
FIG. 22A is a simplified top view showing the flywheel and torsion spring arrangement prior to triggering the injector.
Figure 22B:
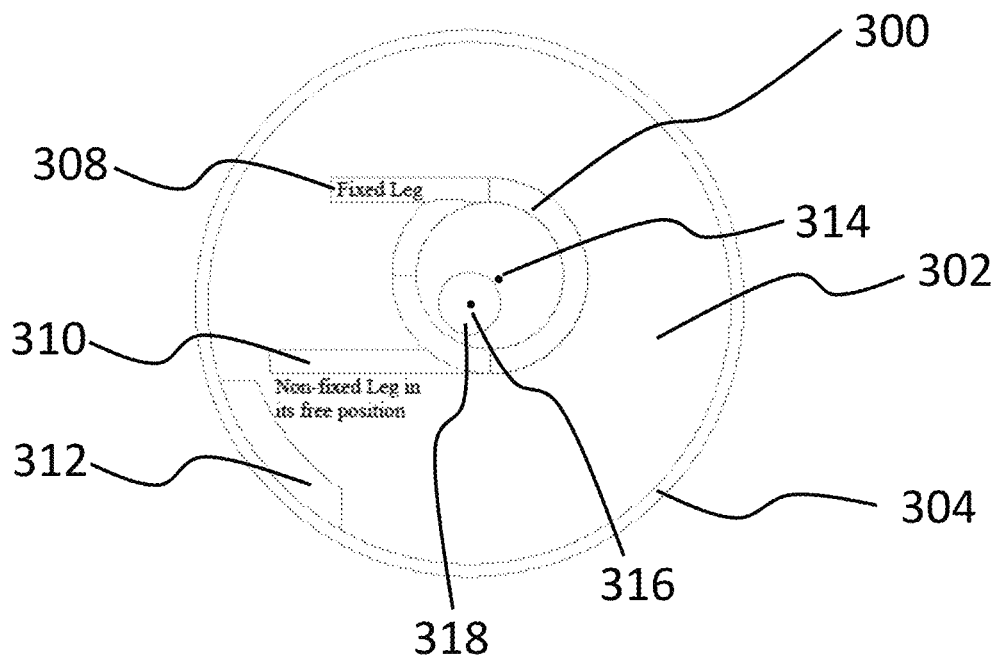
FIG. 22B is a simplified top view showing the flywheel and torsion spring arrangement after triggering the injector.

Now referring also to FIGS. 22A and 22B, shown are top views of the torsion spring 300 and flywheel 302 of FIG. 21, prior to triggering of the auto-injector 100 and after triggering of the auto-injector 100, respectively. As shown in FIG. 22A, the center 314 of the torsion spring 300 is offset from the center 316 of the flywheel 302. As a result, the torsion spring 300 only contacts the flywheel 302 while transferring energy thereto and once complete, as shown in FIG. 22B, the free end 310 of the torsion spring 300 moves out of the way of the ledge or protrusion 312 and does not interfere with the rotation of the flywheel 302. Also shown more clearly in FIGS. 22A and 22B is a central opening 318 in the flywheel housing 306, which accommodates tubing and electrical conductors, as described in more detail below.

Figure 23:
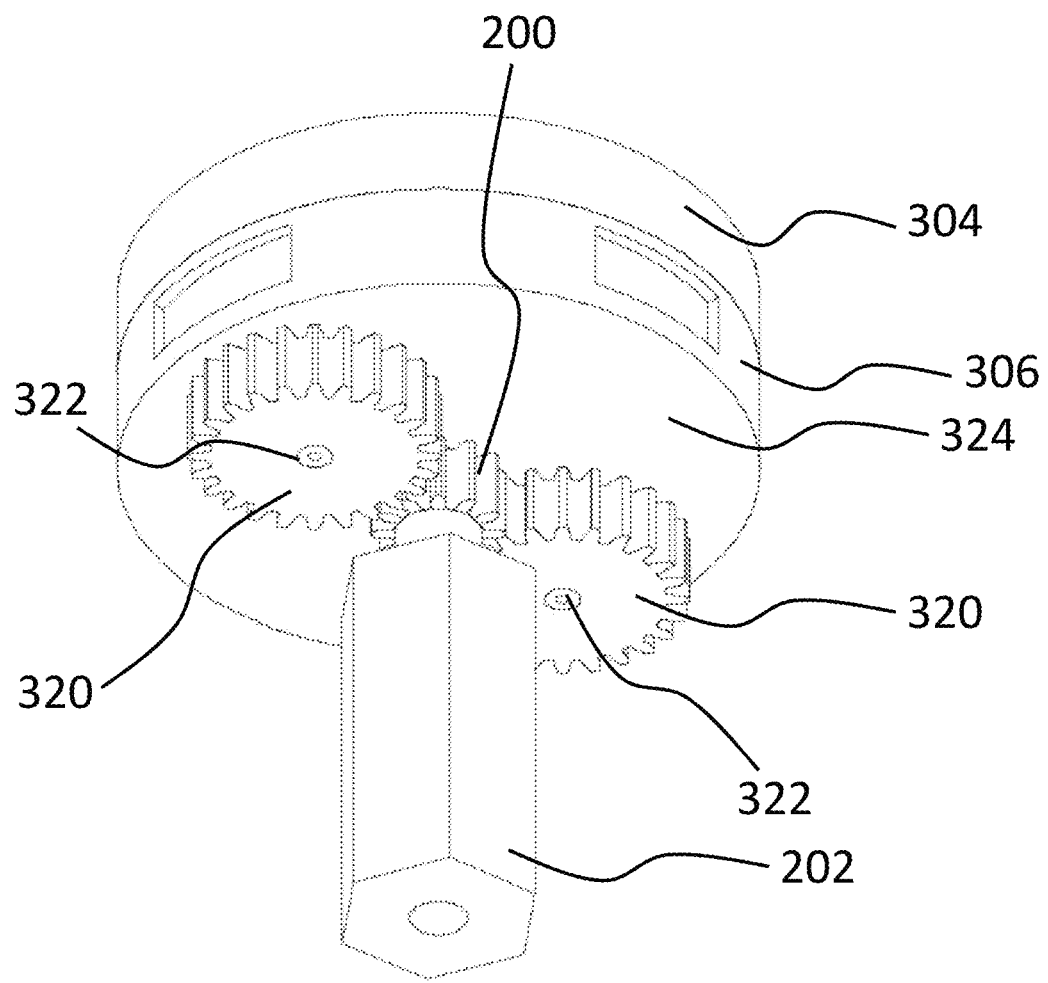
FIG. 23 is a simplified perspective view showing the underside of the flywheel housing with the planet gears and sun gear of the planetary gear system.
Figure 24:
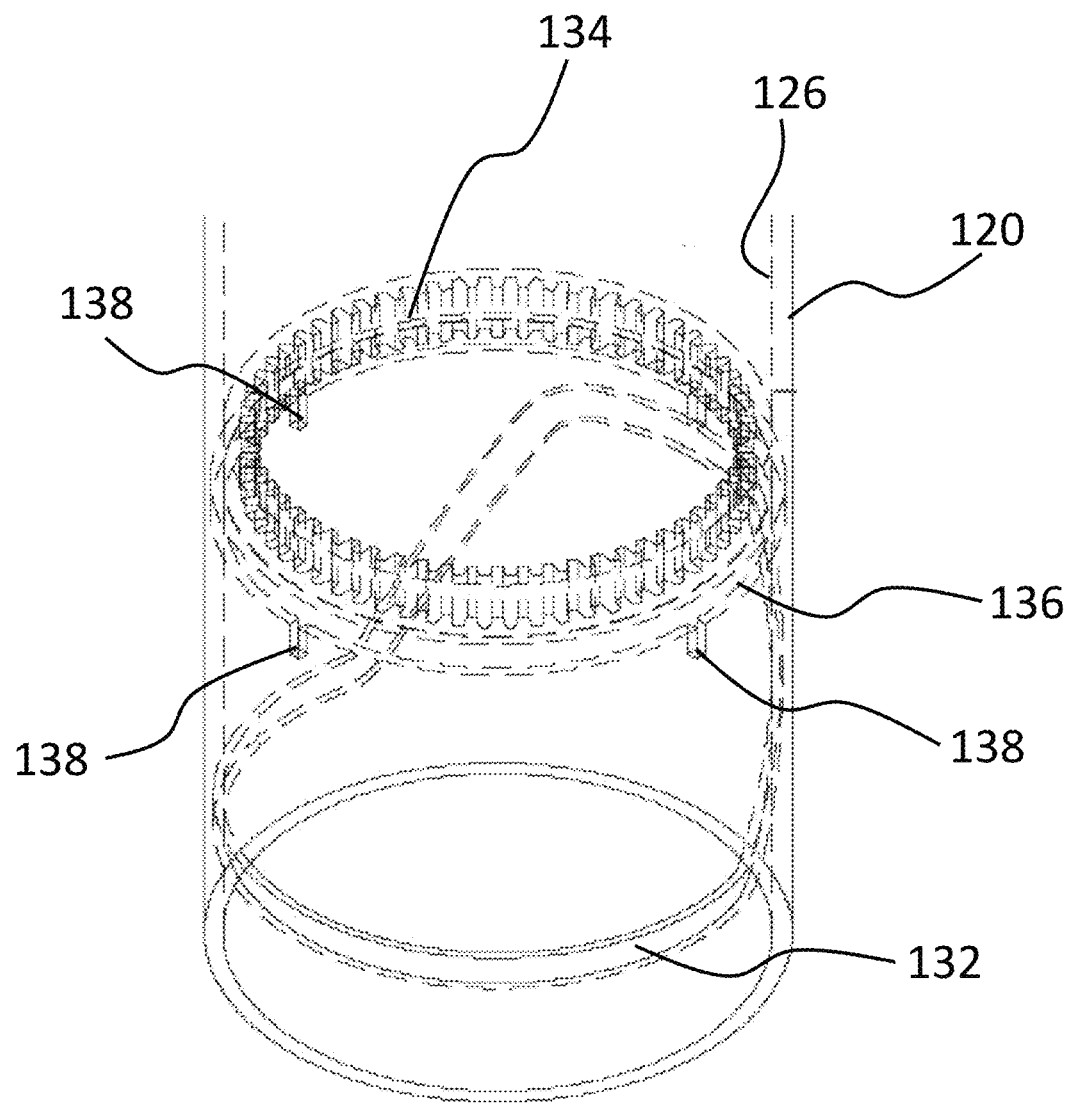
FIG. 24 is a simplified enlarged perspective view of a portion of the control cylinder having internal gear teething formed thereon.
Figure 25:
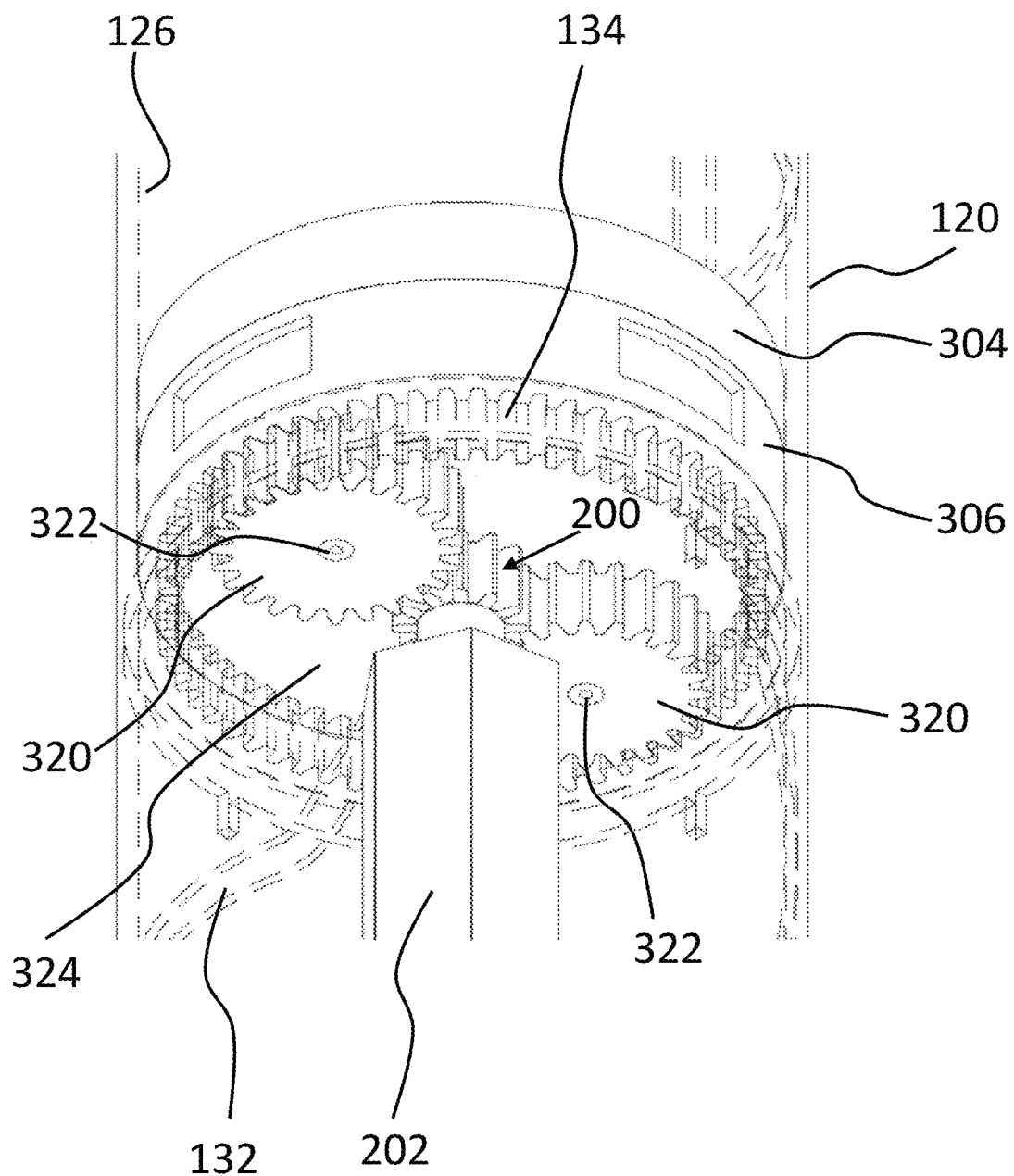
FIG. 25 is a simplified perspective view showing the elements of FIGS. 23 and 24 when the auto-injector device is in an assembled condition.

FIGS. 23-25 show details of the planetary gear system that was mentioned briefly above, which is used to transfer the stored rotational kinetic energy from the flywheel 302 to the control cylinder 120. As shown in FIG. 23, a pair of planet gears 320 are mounted on axes 322 extending from the lower surface 324 of the flywheel housing 306. The flywheel housing 306 is stationary relative to the outer housing 102, and the control cylinder 120 rotates within an annular space that is formed therebetween. The sun gear 200 is coupled to the flywheel 302, via a cylindrical-shaped connector 319 extending through the opening 318 and rotates at the same speed as the flywheel 302. When the sun gear 200 begins to rotate (e.g., counter clockwise), both of the planet gears 320 also begin to rotate about their respective axes 322, but in the opposite direction (e.g., clockwise). Since the flywheel housing 306 is stationary and the planet gears 320 are mounted to the lower surface 324 of the flywheel housing 306, the rotational movement of the planet gears 320 causes the inner ring gear 134 (see FIG. 24) that is formed on the inner surface 126 of the control cylinder 120 to also rotate in the same direction (e.g., clockwise). Since the rotational speed of the flywheel 302 is substantially constant over the timescale of an injection, the control cylinder 120 rotates at a substantially constant speed and is capable of controlling the various movements in a predictable and reproducible manner. Optionally, the torsion spring 300 is replaced by another suitable mechanism for providing the energy to cause the flywheel to spin. Further optionally, a manual assist or fully manual operation may be envisaged. For instance, the user may pump a button or another suitable mechanism to provide supplemental energy for initiating the rotational motion of the flywheel 302 before the torsion spring 300 is released. In this case, the torsion spring 300 is not required to overcome the inertia of the flywheel and it may be possible to use a torsion spring that provides a smaller force. Alternatively, the user may pump a button or another suitable mechanism to provide all of the energy that is required to spin the flywheel 302. In this case, the torsion spring 300 may be eliminated entirely.

Referring now to FIG. 25, shown is detail of the arrangement of the sun gear 200, the planet gears 320 and the inner ring gear 134 when the auto-injector 100 is in the assembled condition. As will be apparent, a different numbers of planet gears 320 may be used, and/or planet gears 320 having a different size relative to the size of the sun gear 200 may be used, and or the planet gears 320 may be mounted to a rotating carrier instead of the stationary lower surface 324 of the flywheel housing 306, thereby supporting different relative rotational movement between the flywheel 302 and the control cylinder 120. In the example that is shown in FIG. 25, the control cylinder 120 is caused to rotate at a slower speed and in an opposite direction relative to the flywheel 302. On the other hand, the sun gear 200 and shaft 202 both rotate at the same rate and in the same direction as the flywheel 302. Since the rotational movement of the shaft 202 is directly transferred to the upper plate 212 of the oscillator element 214, and since there is a plurality of ridges between adjacent depressions defined along the grooved surface 218 (e.g., 15-30 ridges), an oscillatory translational motion in the range 10-100 Hz can be achieved. Thus, the needles 300 of the needle head 162 can be made to move up and down against the subject's skin 10-100 times per second.

Optionally, a "stop" is provided either within the planetary gear system described above or within one or more of the control grooves of the control cylinder 120, etc., to arrest the rotational motion of the control cylinder 120 after the injection has been completed and the needle array has been fully retracted back into the outer housing 102. The stop, regardless of the nature thereof, is a safety feature that is intended to prevent residual rotational kinetic energy stored within the flywheel 302 from causing the control cylinder 102 to continue rotating and thereby cause the needle array to be extended out through the injecting end of the outer housing 102 a second time.

Of course, the flywheel 302, the torsion spring 300, the planetary gear system, etc., are described in the context of a specific and non-limiting embodiment of the auto-injector 100. As will be apparent, alternative mechanisms exist to convert stored potential energy into regulated rotation of a shaft and may be used instead in different embodiments. Of course, one of skill in the art may envision various modifications to the disclosed embodiments. For instance, as discussed supra, an electro-mechanical auto-injector may comprise an electric motor powered by DC power supply or by an AC power supply, e.g., a battery. An output shaft of the motor may be coupled to e.g., the sun gear 200 shown in FIG. 23 and provide the power necessary to drive the various components of the auto-injector in a manner similar to that as described above. A suitable electronic controller may be employed to control the movements of the various components and sub-assemblies during an injection. As will be further apparent, the flywheel 306 and/or various other components may be omitted or substituted in the electro-mechanical auto-injector. Although the cost of such an electro-mechanical version of the auto-injector 100 may be higher than the purely mechanical version, such a device is nevertheless well suited for certain applications including for instance veterinary applications in which an entire herd of animals may be injected using a single device and without changing the needle array, etc.

In addition to injecting the injectable substance into the subject's skin tissue, the auto-injector 100 may also employ various supplemental techniques to promote a robust immune response by the subject. One such supplemental technique, involving the oscillatory up and down translational movement of the needle head 162, has already been discussed supra. The oscillatory translational movement of the needle head 162 causes the needles 300 to move up and down rapidly during the injection, at a rate that may be between 10-100 times per second, which causes a minimal amount of localized damage to the subject's skin tissues around the injection site. This damage serves several functions. Firstly, it promotes the distribution of the injectable substance into the subject's skin tissue. Secondly, the damage triggers a response by the various antigen-presenting cells (APCs) in the subject's skin tissue, which respond to such damage by mounting an immune response.

Another supplemental technique that may be used during an injection is electroporation. As discussed in the introduction section, electroporation involves the application of brief electrical pulses that result in the creation of aqueous pathways within the lipid bi-layer membranes of mammalian cells. This allows the passage of even large molecules, including DNA, through the cell membrane, which would otherwise be less permeable. Although the precise mechanism by which electroporation enables cell transformation has not been elucidated, a proposed theoretical model involves a portion event due to the destabilization of the membrane, followed by the electrophoretic movement of charged molecules into the cell. For electroporation to occur, the formation of pores requires that a threshold energy be achieved, and the movement produced by the electrophoretic effect depends upon both the electric field and the pulse length. In the case of DNA vaccines, electroporation has been shown to quantitatively enhance immune responses, increase the breadth of those immune responses as well as improve the efficiency of dose.

Figures 26, 27:
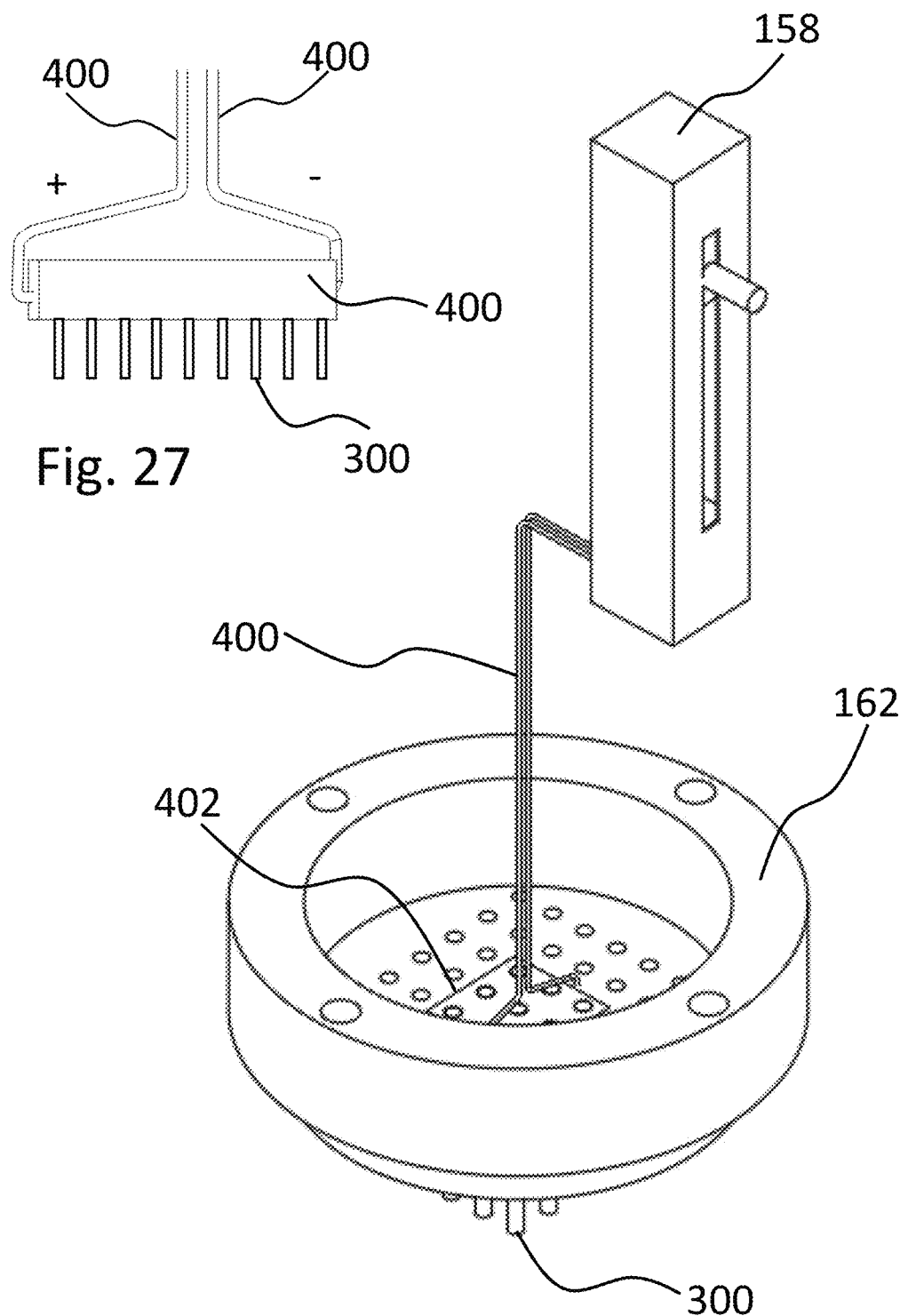
FIG. 26 is a simplified perspective view showing detail of the electroporation subassembly.
FIG. 27 is a simplified view showing detail of the electroporation subassembly connection to the needle array.

FIGS. 26-33 show various details of an electroporation sub-system that is suitable for being incorporated into the auto-injector 100. FIG. 26 is highly simplified and shows only the piezoelectric element 158 of FIG. 1, the needle array 162, and electrical connectors extending therebetween. During use, a not illustrated hammer presses on a not illustrated piezoelectric crystal in the piezoelectric element 158, which produces an electrical current that flows via the conductors 400 to the needles 300 of the needle head 162. At least some of the needles 300 within a portion 402 of the needle head 162 are electrically conductive (e.g., metallic) and conduct the electrical current into the subject's skin. Alternatively, instead of being hollow needles 300, the conductive elements of the needle head 162 may be micro-electrodes that do not carry the injectable substance into the subject's skin (i.e., "solid needles"). FIG. 27 shows a side view of the conductors 400 connected to the portion 402 of the needle head 162. In this example, all of the needles 300 are the same, i.e., hollow metallic needles for injecting the injectable substance and for applying the electrical current.

Figure 28:
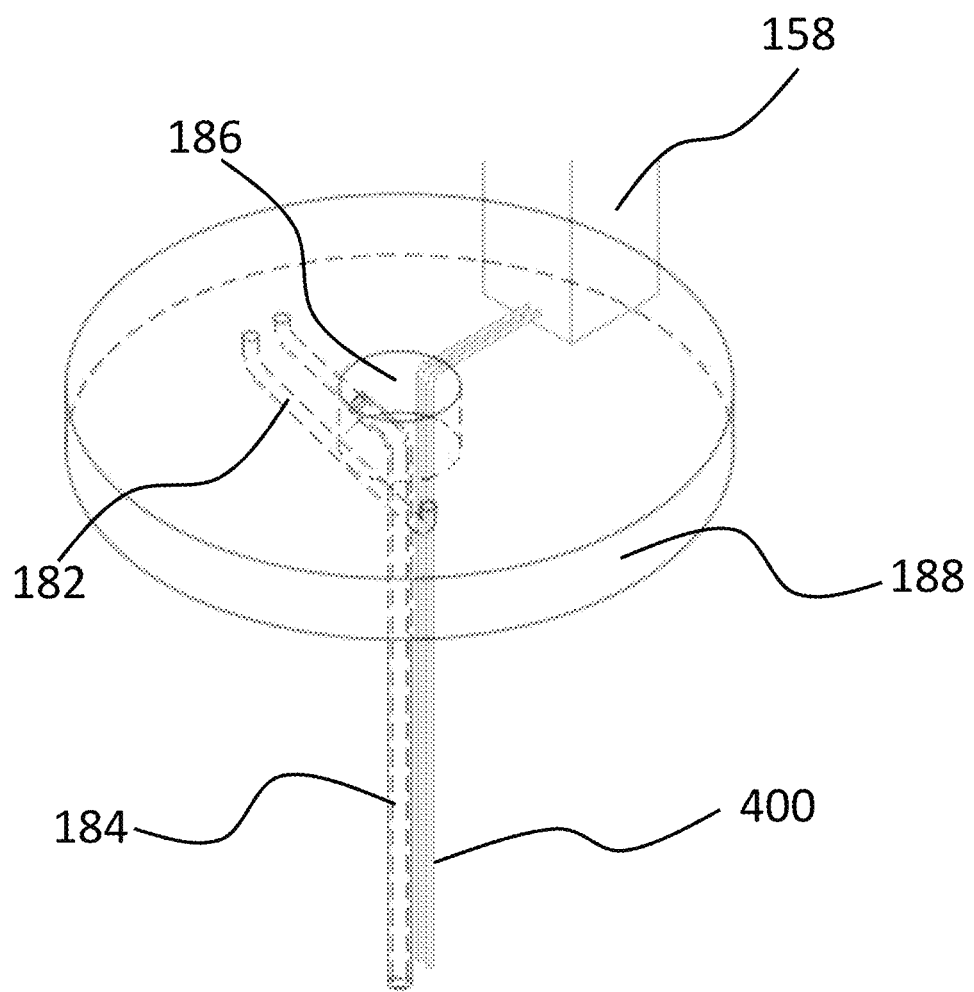
FIG. 28 is a simplified perspective view showing detail of the fluid tubing and electroporation subassembly electrical conductors.

FIG. 28 shows the conductors 400 extending from the piezoelectric element 158 through the opening 186 in the support base or plate 188 (which is shown transparent in FIG. 28 to facilitate a better understanding). Also shown in FIG. 28, using ghost lines, are the first conduit 182, which extends between gas cylinder 170 and the vial 176, and the second conduit 184, which extends between the vial 176 and the needle head 162. As such, the conductors 400 and the second conduit 184 both pass through the opening 186 and extend through respective central openings in each of the torsion spring housing 304, the flywheel housing 306, the sun gear 200, the shaft 202, the follower plate 206, and the upper plate 212 and lower plate 216 of the oscillator element 214, all the way to the needle head 162.

Figure 29:
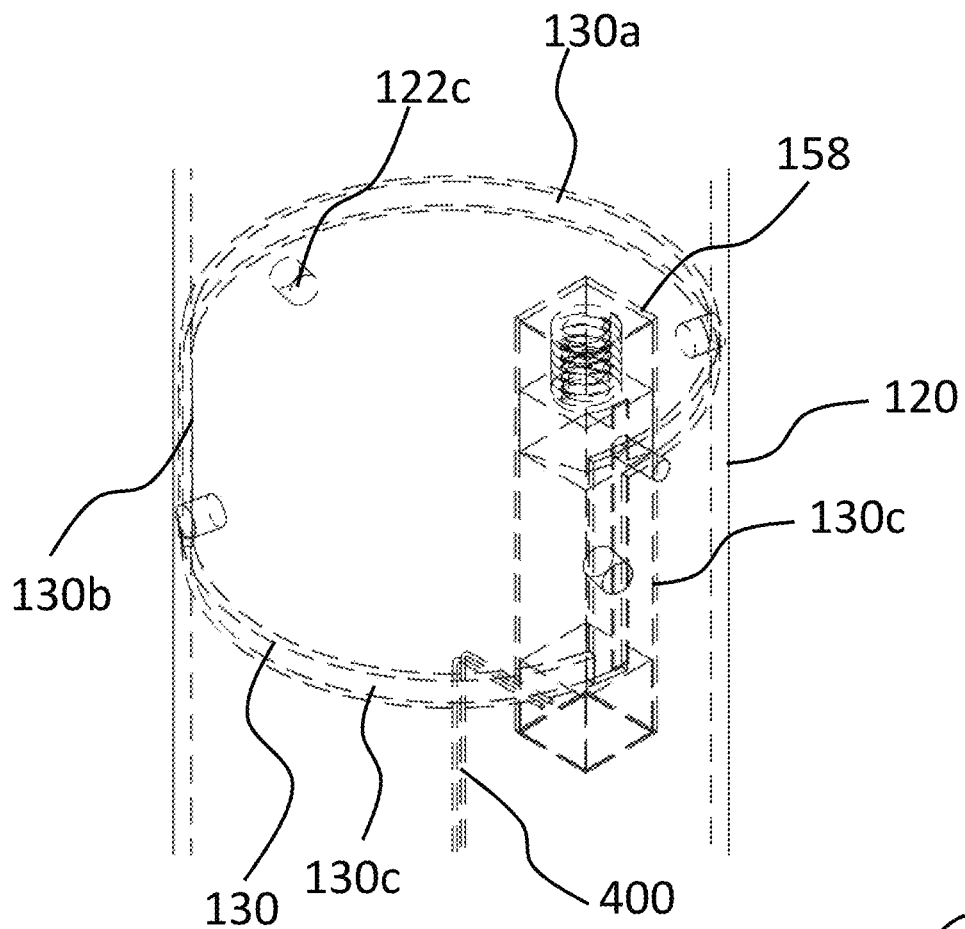
FIG. 29 is a simplified perspective view showing the piezoelectric assembly prior to electroporation initiation.
Figure 30:
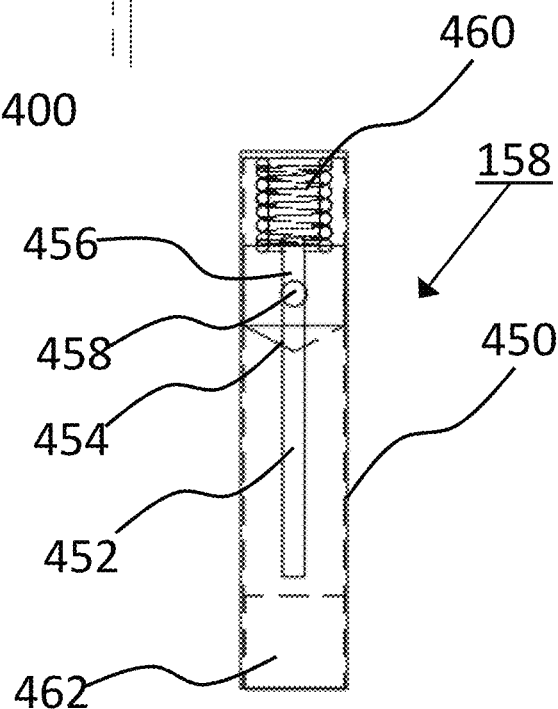
FIG. 30 is a simplified front view showing the piezoelectric assembly prior to electroporation initiation.
Figure 31:
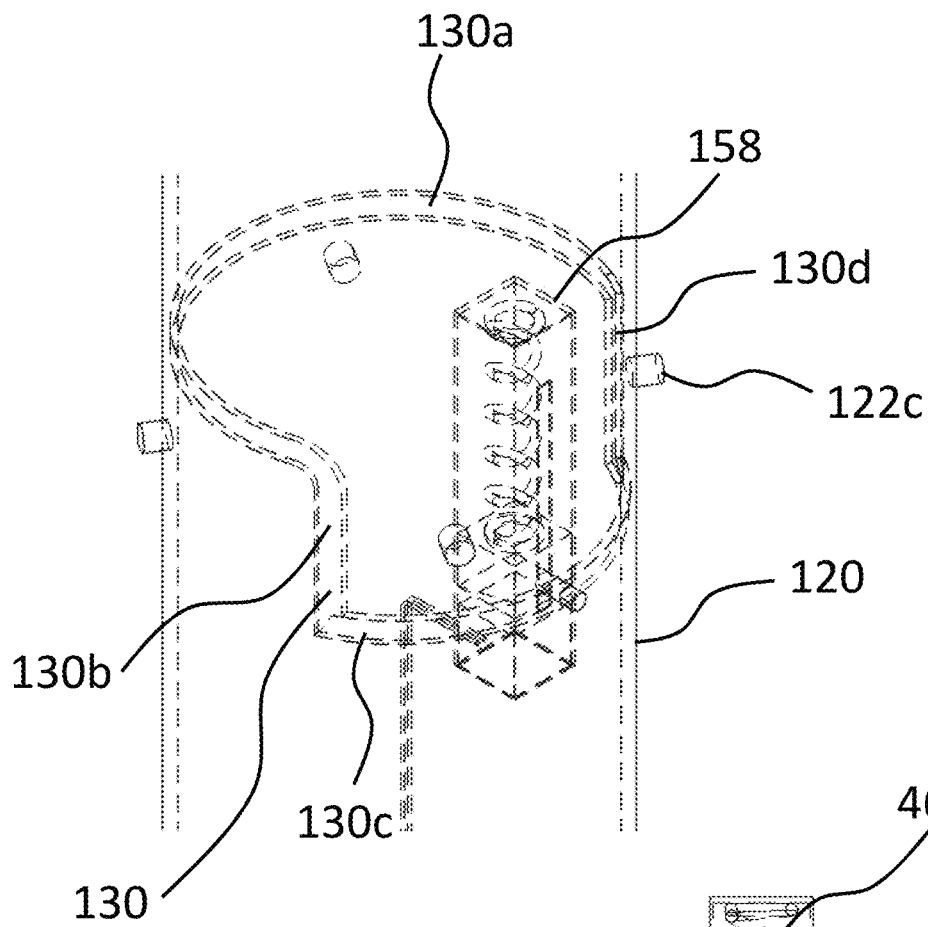
FIG. 31 is a simplified perspective view showing the piezoelectric assembly after electroporation initiation.
Figure 32:
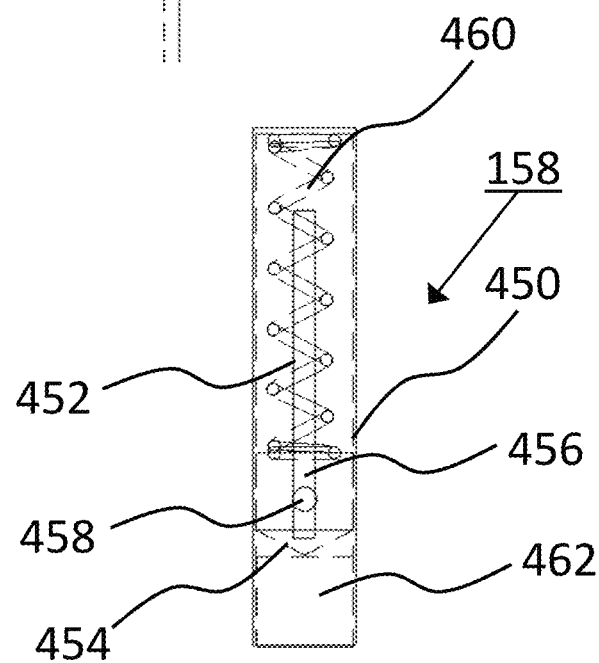
FIG. 32 is a simplified front view showing the piezoelectric assembly after electroporation initiation.

FIGS. 29 and 30 illustrate the features of the piezoelectric element 158 at a first point during the rotation of the control cylinder 120, and FIGS. 31 and 32 illustrate the features of the piezoelectric element 158 at a second point during the rotation of the control cylinder 120. Referring first to FIGS. 30 and 32, the piezoelectric element 158 has a housing 450 that may be secured to the support base or plate 188. The housing 450 has a longitudinal slot 452 defined through one side thereof. A hammer 454 is mounted on one end of a shaft 456 within the housing 450. A protrusion 458 extends outwardly from the shaft 456 through the slot 452 and is received within the piezoelectric element control groove 130 on the inner surface 126 of the control cylinder 120. A compression spring 460 is housed at an upper end of the housing 450.

Referring now to FIG. 29, during an injection the control cylinder 120 rotates relative to the piezoelectric element 158 after the auto-injector 100 has been triggered, and the protrusion 458 initially follows a first groove-portion 130*a* of the piezoelectric element control groove 130. The first groove-portion 130*a* extends only in the circumferential direction around the control cylinder 120. As the control cylinder 120 continues to rotate, the protrusion 458 eventually enters a second groove-portion 130*b* of the piezoelectric element control groove 130, which extends only in the longitudinal direction of the control cylinder. This allows the protrusion 458 to move within the slot 452 of the housing 450, which in turn allows the compression spring 460 to expand and press the hammer 454 downwardly and into contact with a piezoelectric crystal 462, which is housed at the lower end of the housing 450. The pressure that is applied to the piezoelectric crystal 462 by the compression spring 460, via the hammer 454, creates an electrical current, which flows through the conductors 400 to the needle head 162. The hammer 454 continues to be applied to the piezoelectric crystal during the time that the protrusion follows a third groove-portion 130*c* of the piezoelectric element control groove 130, which extends only in the circumferential direction around the control cylinder 120. When the rotation of the control cylinder 120 causes the protrusion to enter a fourth groove-portion 130*d* of the piezoelectric element control groove 130, the pressure is taken off the piezoelectric crystal 462 and the hammer 454. The fourth groove-portion 130*d* extends both circumferentially and longitudinally within the inner surface of the control cylinder 120, such that the protrusion 458 is guided within the slot 452 back to its initial position against the force of the compression spring 460.

The timing of the electrical pulse generated by the piezoelectric element 158 is determined by the shape of the piezoelectric element control groove 130 and the rate of rotation of the control cylinder 120. In this specific and non-limiting example, there is a single relatively long third groove-portion 130*c* during which the hammer 454 is caused to apply pressure to the piezoelectric crystal and thereby generate an electrical current. However, the shape of the piezoelectric element control groove 130 may be modified, such as for instance by providing multiple third groove-portions 130*c*, either of similar length or of different lengths, to create a pulse sequence in which an electrical current is applied to the subject's skin multiple times during an injection, with periods between the applications of electrical current during which no electrical current is applied.

In some embodiments, the electroporating pulses are associated with an electrical field that prevents damage to the cells of the epidermal tissue. In further embodiments, the electroporating pulses are associated with an electrical potential that is nearly painless. For example, the electroporating pulses are associated with an electrical potential of about 1 volt to about 30 volts, or preferably about 15 volts to about 20 volts, an electrical current of about 1 mA to about 50 mA, or preferably about 10 mA to about 15 mA, and a duration ranging from about 80 ms to about 150 ms, or preferably 100 ms, or a combination thereof. These pulses can be delivered in a series, preferably 1-10 pulses, and more preferably 1-3 pulses.

Alternatively, a system using a battery may be used to generate the electrical current. Further alternatively, the rotational motion of the flywheel 302 may be used to generate the electrical current using suitably placed magnets and conductors.

Figure 33:
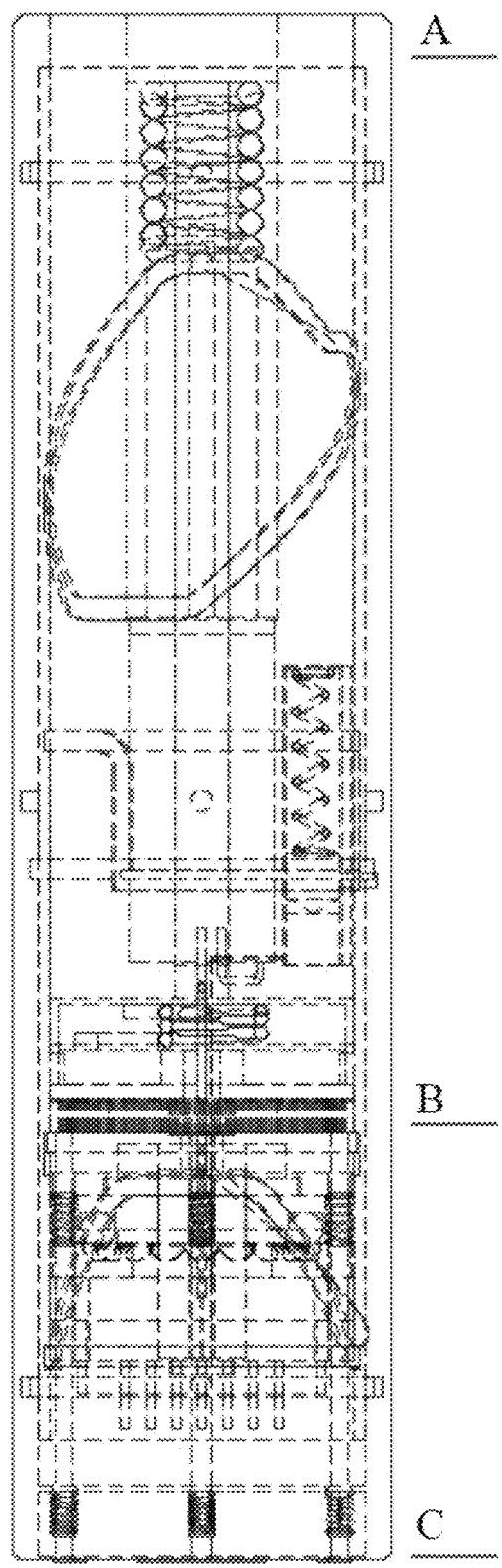
FIG. 33 is a simplified side view showing the first exemplary auto-injector device in a fully assembled condition.
Figure 34:
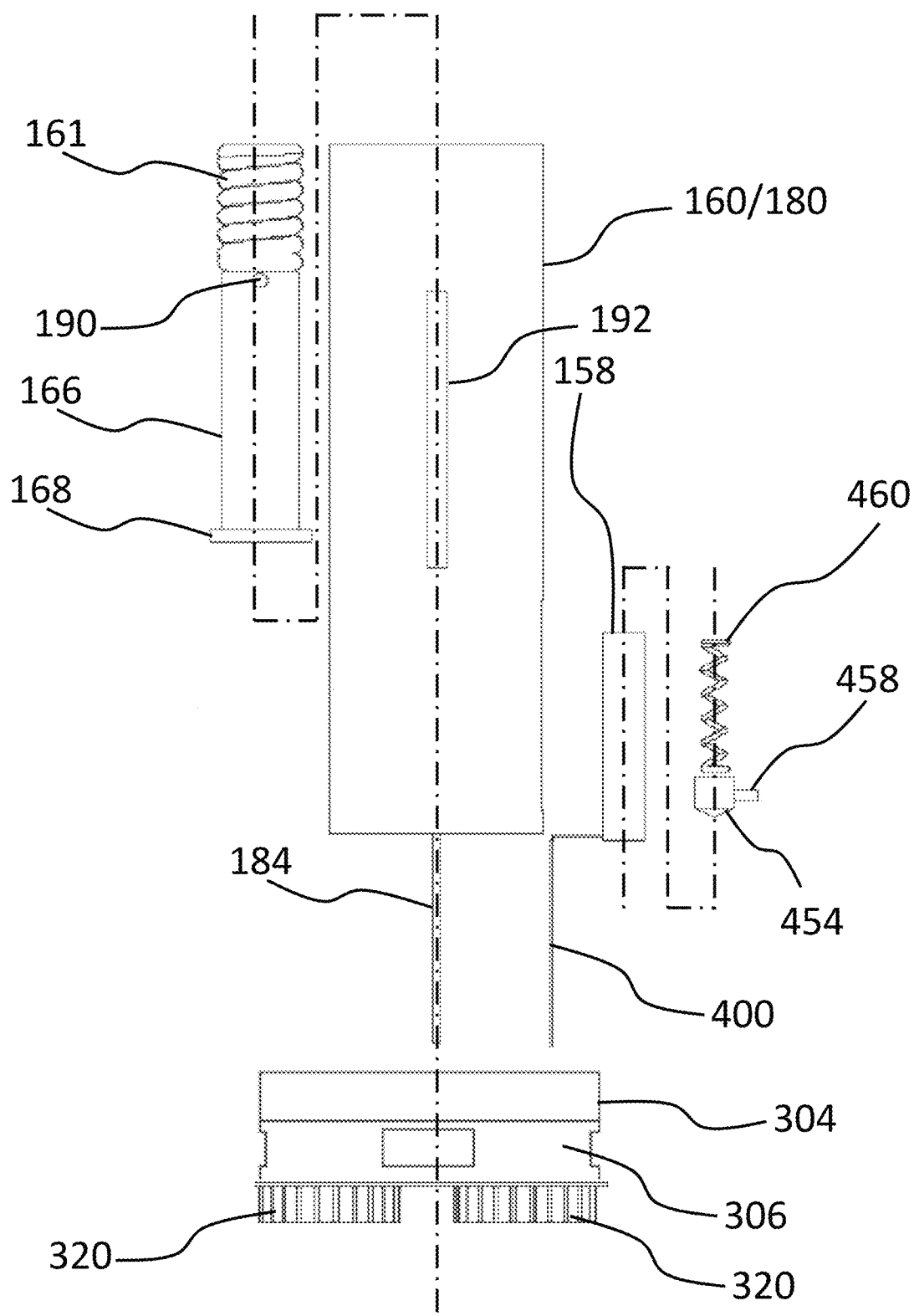
FIG. 34 shows, in isolation, the components of the first exemplary auto-injector within section A-B of FIG. 33, with the outer housing, control cylinder and various other housings omitted for improved clarity.
Figure 35:
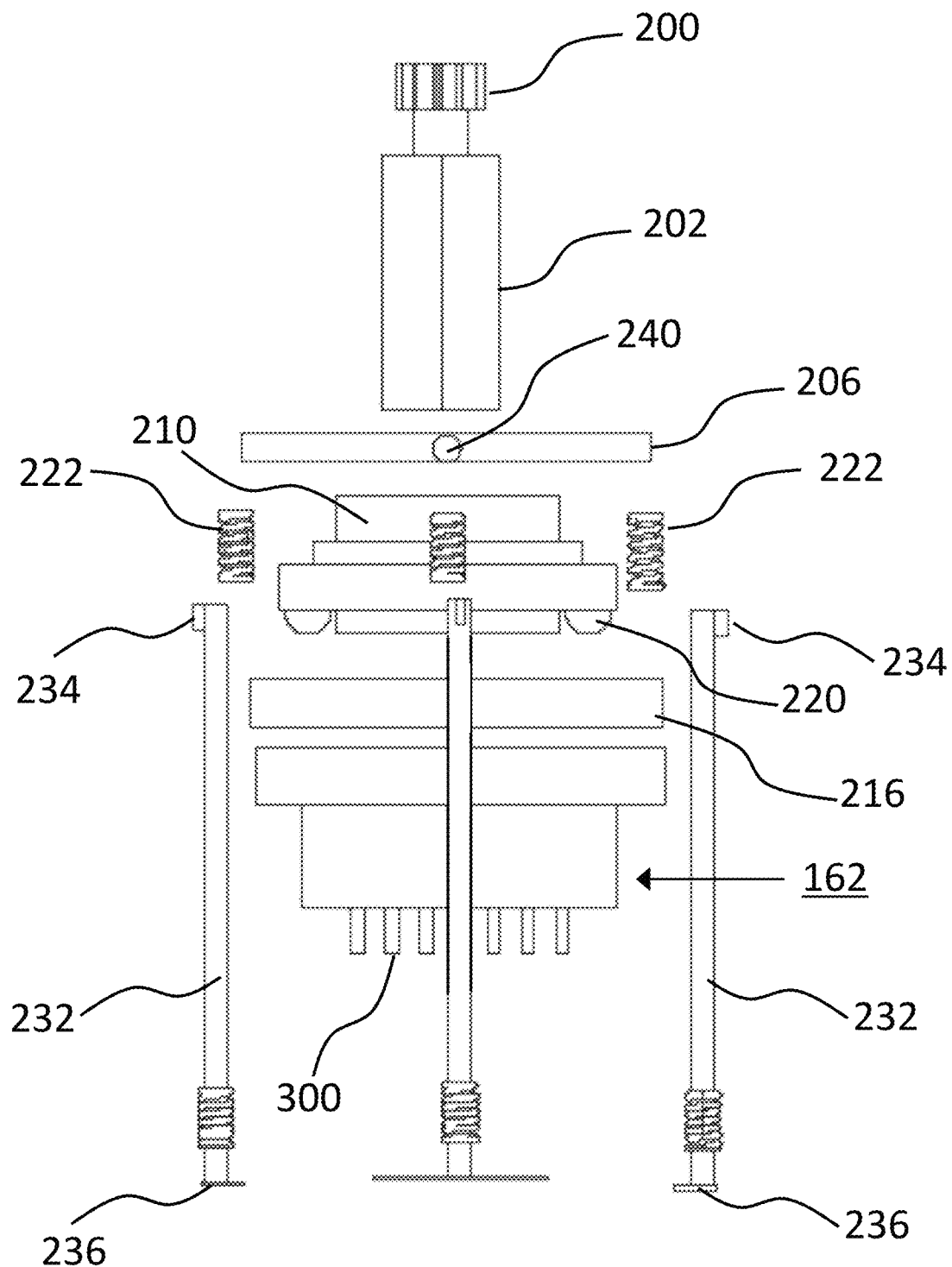
FIG. 35 shows, in isolation, the components of the first exemplary auto-injector within section B-C of FIG. 33, with the outer housing, control cylinder and various other housings omitted for improved clarity.

The major features of the first exemplary auto-injector 100 have already been described above with reference to FIGS. 1-32. FIG. 33 is presented to show the auto-injector 100 in a fully assembled condition. Since the auto-injector 100 comprises a nested arrangement of individual elements, there is a great deal of overlap in FIG. 33 which obscures the arrangement of the various elements. To facilitate a better understanding, regions denoted A-B and B-C have been indicated in FIG. 33. FIG. 34 shows the various elements in region A-B separated from one another, thereby avoiding overlap, such that each element can be seen more clearly. Similarly, FIG. 35 shows the various elements in region B-C separated from one another, thereby avoiding overlap, such that each element can be seen more clearly.

The auto-injector 100 described herein, as well as various modified versions that have been discussed explicitly or implicitly above, may achieve at least some of the following advantageous results.

Dose-sparing of up to ten times, without compromising immunogenicity, versus subcutaneous and intramuscular routes.

Zero dead volume and injection under pressure eliminates wastage of the injectable substance, ensuring the full amount of the injectable substance is injected.

Combination of injection performed with one or more supplemental techniques selected from electroporation, oscillating needle array to cause localized skin damage, and suction (e.g., cupping) above the injection site after the injectable substance has been injected enhances the subject's immune response.

Fool-proof design ensures proper orientation of the auto-injector on the subject's skin prior to triggering an injection.

Easily gripped by the subject receiving the injection or by another user administering the injection to the user without awkward manipulation of a physical plunger etc.

As discussed supra the auto-injector 100 may be modified and adapted to be suitable for purposes such as, e.g., withdrawing fluid samples from the tissues of the subject. In such an embodiment the needle head 162 may include some needles that penetrate the subject's skin to a desired target layer, such as for instance the dermis layer, and may include some needles that do not penetrate all the way to the target layer and act as stabilizing elements during the process of withdrawing the fluid sample. The auto-injector may be modified to include a sampling chip comprising a large number (e.g., 5,000) sample locations, or another suitable sample holding element. Some of the sample locations may be redundant. Diagnostics may be performed on the withdrawn fluid samples.

3. Target Injection Site

Figure 36:
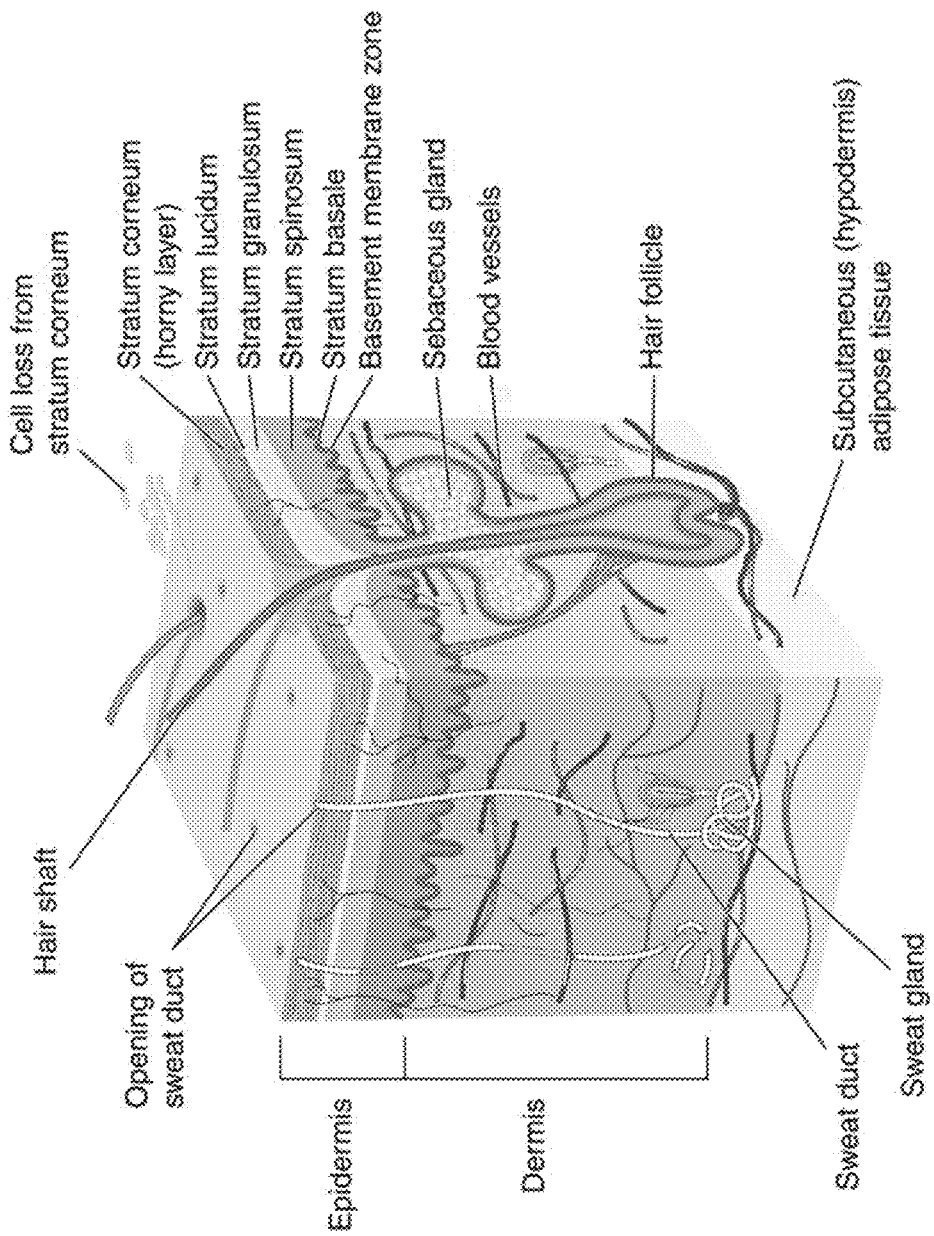
FIG. 36 is a simplified diagram showing layers of the human skin.

Referring now to FIG. 36, shown is a representation of the anatomical structure of the human skin, which is constructed in a layered form including epidermis, dermis, subcutaneous tissue (hypodermis), and muscular tissue. The epidermis is about 0.1 to 2 mm thick and can be distinguished or classified into the horny cell layer and the intradermis. In each of the layers of the skin structure, the tissue and the main cells or the like for constructing the tissue have different features.

Specifically, the horny cell layer in the epidermis is principally composed of keratinocytes and is positioned on the outermost surface side of the skin. In general, the horny cell layer is about 0.01 to 0.015 mm thick and functions as the so-called barrier layer. In order to physically insulate the interior of the human body from the external environment to some extent, a relatively high strength is required. Other cells in the epidermis are Langerhans cells and pigment cells (melanocytes). The pigment cells in the epidermis function to avoid the influence of the ultraviolet light radiated from the external environment. On the other hand, the dermis includes dendritic cells. The dendritic cells in the dermis are cells that participate in the antigen-antibody reaction. They can be joined by Langerhans cells that can be triggered by disruption of the epidermis and can be co-involved in the immunization process. More particularly, the dendritic cells recognize the presence of an antigen by incorporating the antigen, and the antigen-antibody reaction, in which lymphocytes are activated to play a role to attach the foreign matter, is induced.

The dermis contains a network of vessels and capillary vessels, and further includes sweat glands for adjusting body temperature, hair roots of body hair (including hair on the head), and sebaceous glands associated therewith. The dermis is the layer of the skin that communicates between the epidermis and the interior of the human body (subcutaneous tissue and muscular tissue). The dermis also includes fibroblasts and collagen cells.

Figure 37A:
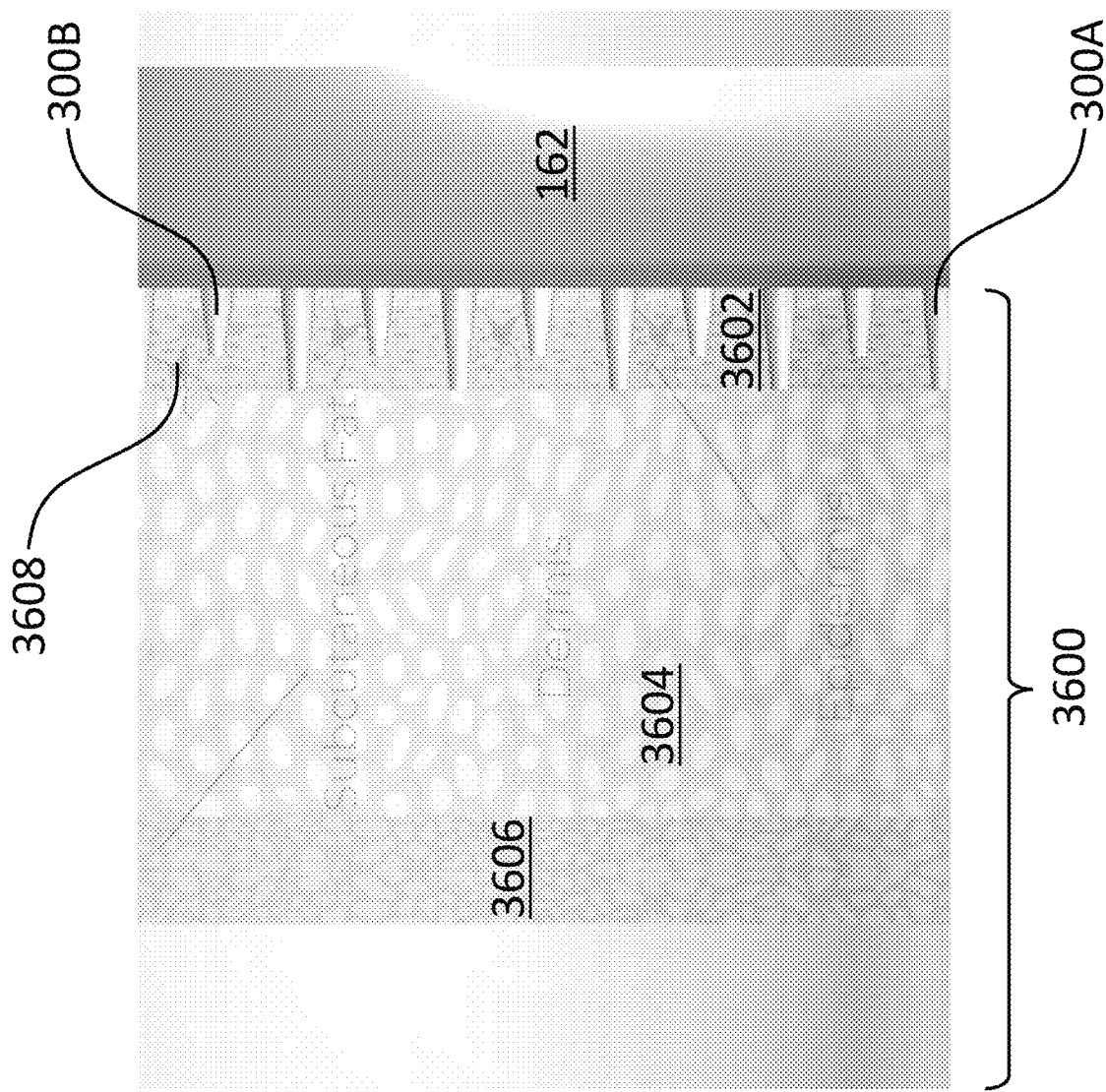
FIGS. 37A-E are a series of schematic diagrams corresponding to different times during an injection of an injectable substance into the tissues of a subject, in which: FIG.

Referring now to FIGS. 37A-D, shown are a series of schematic diagrams corresponding to different times during an injection of an injectable substance into the tissues of a subject. FIG. 37A shows the needles 300 of the head 162 of the auto-injector 100 in contact with the skin 3600 of the subject, which includes the epidermis layer 3602, the dermis layer 3604 and the subcutaneous fat layer 3606. In the presently preferred embodiment, the plurality of needles 300 includes needles of at least two lengths, including relatively long needles 300A and relatively short needles 300B. Langerhans cells 3608 are shown within the epidermis layer 3602.

The auto-injector 100 is configured such that the needles 300 of the needle head 162 is moved into contact with the subject's skin 3600 with sufficient speed and pressure to allow the needles 300A and 300B to penetrate through the dry, protective outer stratum corneum (horny layer). The needles of different length 300A and 300B avoid the "bed of nail" problem that may occur if all of the needles are of the same length. A further advantage of performing an injection using needles 300A and 300B of different lengths is that the delivery of the injectable substance is better targeted to the desired layer of the skin 3600 and can be spread out more evenly over a larger area.

Figure 37B:
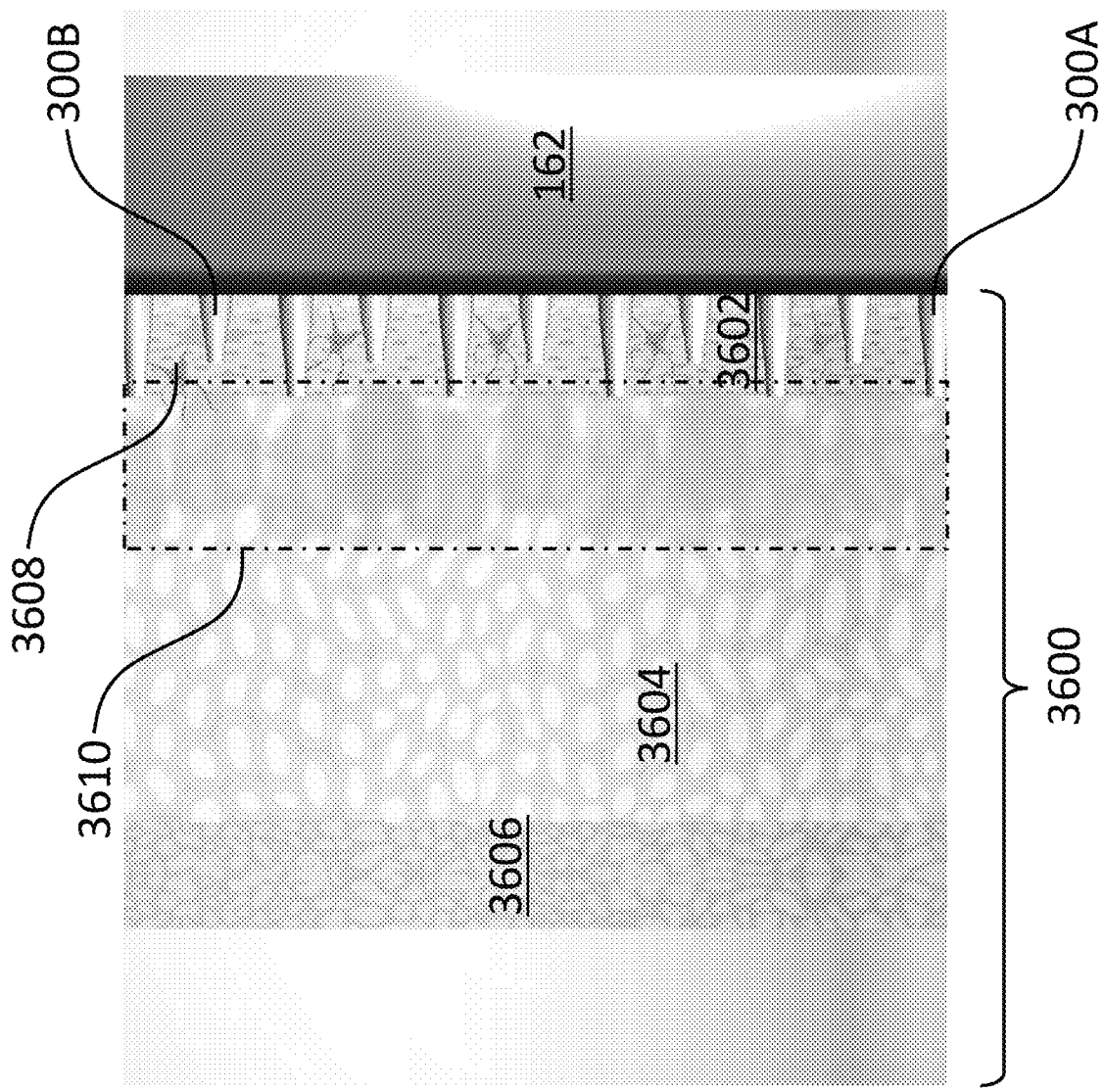

Referring still to FIG. 37A, some of the needles 300A penetrate the subject's skin 3600 to the depth of the dermis layer 3604 and others of the needles 300B penetrate the subject's skin 3600 only to the epidermis layer 3602. The injectable substance is forced out through the needles 300A and 300B, under pressure, during one or more cycles of the oscillatory movement of the needle head 162. FIG. 37B shows the injectable substance after injection into the subject's skin 3600. The dash-dot line rectangle 3610 indicates the distribution of the injectable substance. As will be apparent, the individual needles 300A and 300B each inject a "cloud" of the injectable substance, distributed throughout the epidermis layer 3602 (if injected via needles 300B) and throughout the dermis layer 3604 (if injected via the needles 300A). The internal bores and/or other properties of the different types of needs 300A and 300B may be selected so as to inject the injectable substance in a controlled manner that targets the dermis layer 3604. For instance, the properties of the needles may be tailored such that the pressure under which the injection is performed is sufficient to transport the injectable substance to the target dermis layer 3604 without "blowing through" to the underlying subcutaneous fat layer 3606. The pressure may be tailored, at least in part, considering the properties of the skin tissue layer into which each of the different types of needles is injecting. Injection of the injectable substance via a first subset of needles within the dermis layer 3604 may require a pressure that is different than that required for injection of the injectable substance via a second subset of needles within the epidermis layer 3602.

Figure 37C:
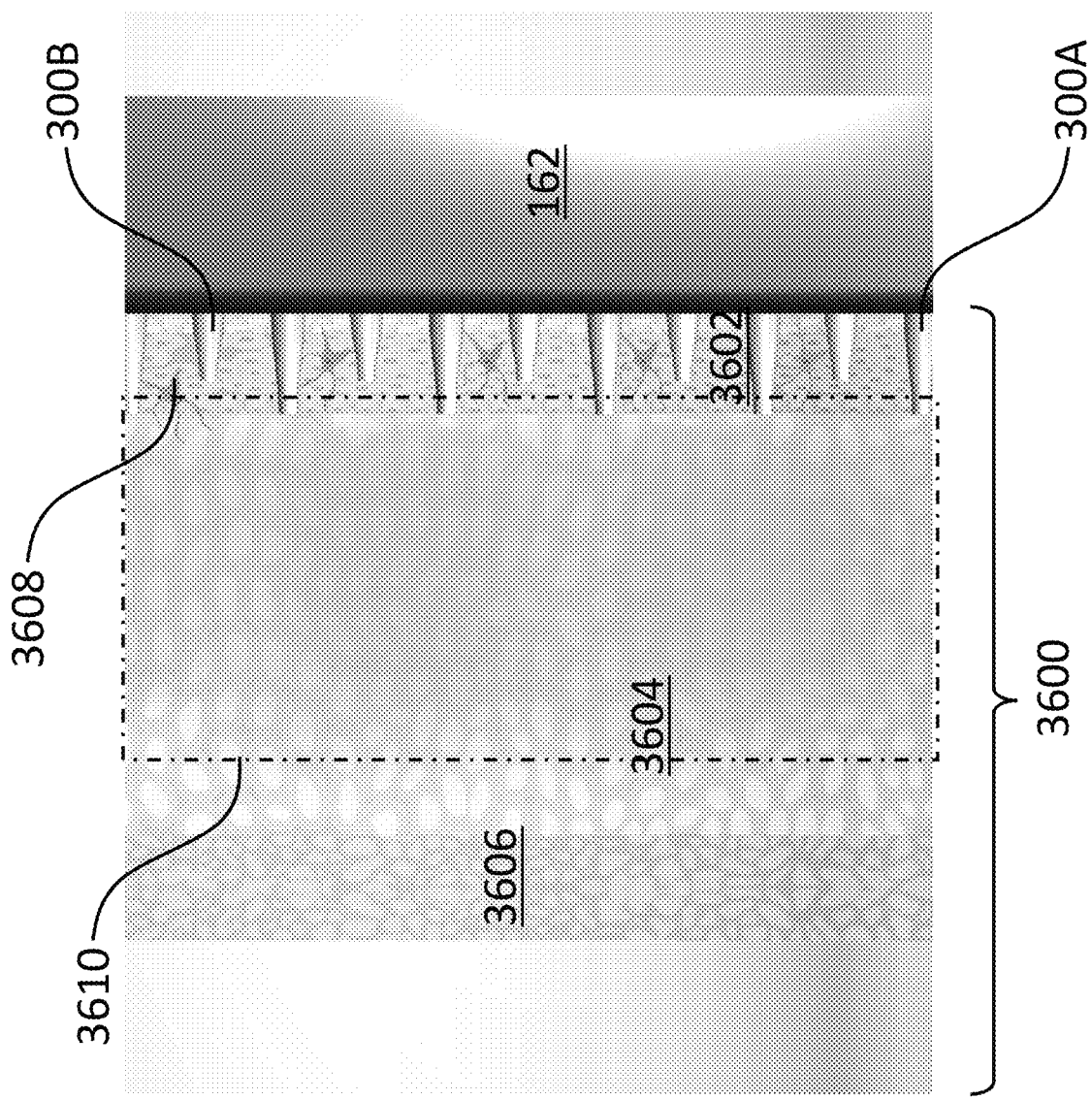
Figure 37D:
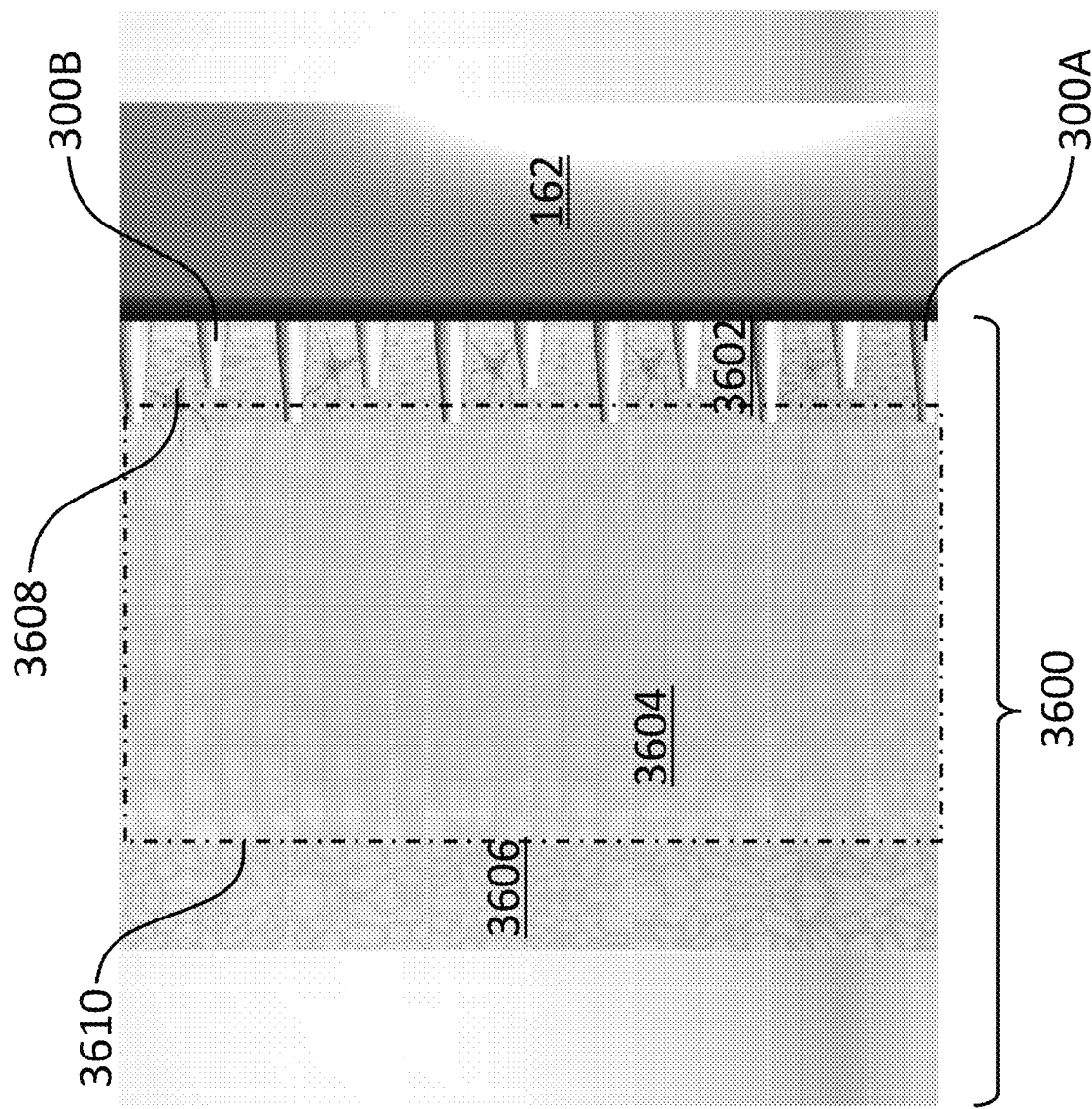
Figure 37E:
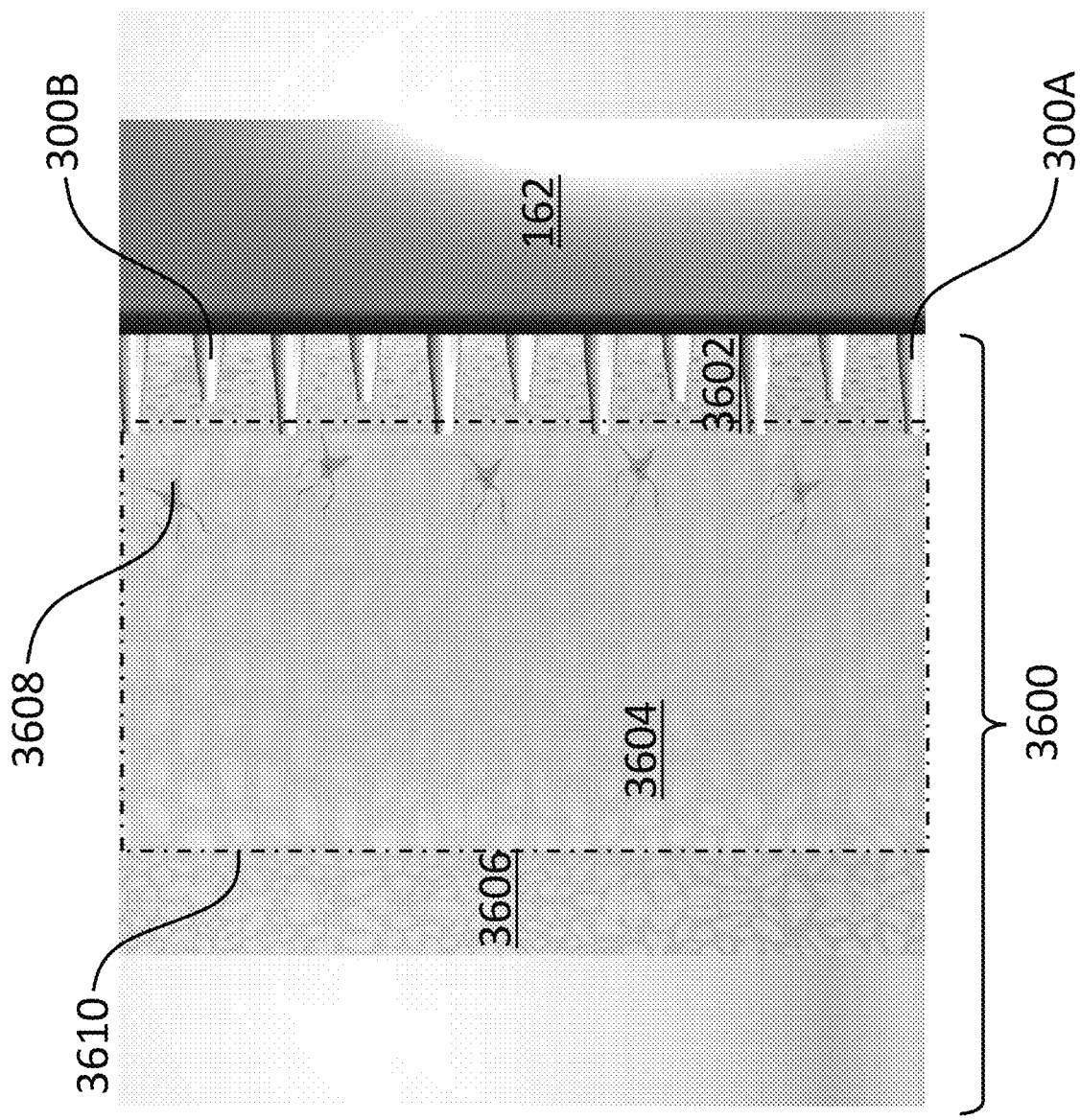

Initially, the individual clouds of the injectable substance are somewhat separated one from another and are localized and generally aligned with the ends of the respective needles through which they were injected into the subject's skin tissues. The clouds of the injectable substance diffuse and spread out within the subject's skin 3600, as is illustrated in FIGS. 37C and 37D by the use of a dash-dot rectangle 3610 that is larger than the one shown in FIG. 37B. The result is a highly uniform distribution of the injectable substance within the target dermis layer 3604.

It is also worth noting that in at least some embodiments the auto-injector 100 induces a translational oscillatory movement of the needle head 162 during an injection, and accordingly the needles 300A and 300B are not static as suggested in FIGS. 37A-D. Instead, the needles 300A and 300B are repeatedly extended to their respective maximum penetration depths and withdrawn at least partially out of the subject's skin tissue. The injection of the injectable substance is preferably controlled to occur when the needles 300A and 300B are extended to their respective maximum penetration depths. Preferably, the injectable substance is injected during a plurality of oscillations of the needle array, with each portion of the injection occurring when the needles 300A and 300B are extended to their respective maximum penetration depths for injecting into respective target layers of the subject's skin.

According to another embodiment, an auto-injector is provided in which a rotational movement of the needle head is performed during the oscillatory translational movement. For instance, each time the needles are at least partially withdrawn from the subject's skin tissue a small rotational movement of the needle array occurs such that new puncture holes are formed when the needles are subsequently extended to their respective maximum penetration depths again. Depending on the nature of the injectable substance, the optimum required number of penetration events (i.e., oscillations and rotations of the needle array) may be different. For instance, between 10 oscillations of the needle array and 100 oscillations of the needle array per second may be suitable for different injectable substances. Multiple penetration events create additional trauma at the injection site to maximize the amount of stimulation of the Langerhans cells 3608, which have the ability to move from the epidermis layer 3602 to the dermis layer 3604 and start the cascade of the immune response. Advantageously, stimulating the Langerhans cells 3608 by mechanically damaging the subject's skin tissue avoids the need to include adjuvants in the injectable substance, which reduces the occurrence and/or severity of undesirable side-effects.

Referring now to FIGS. 38-48, shown are different views of the major components of an alternative needle head 3900 and an alternative needle control sub-assembly 3902 of a second exemplary auto-injector. Bearing element 3940 supports a rotational movement of the needle head 3900 relative to the needle control sub-assembly 3902 during operation. In this embodiment, the needle head 3900 and the needle control sub-assembly 3902 replace the needle head 162 and the needle control sub-assembly 164, respectively, that were described with reference to FIGS. 9-19. In some embodiments, the remainder of the auto-injector 100 remains substantially the same or requires only minor modifications. For instance, the second exemplary auto-injector may include the plunger sub-assembly 154, the vial interface 156, the piezoelectric element 158 and the energy source and storage sub-assembly 159 that were described above. The term "auto-injector 100" will continue to be used when referring to an auto-injector device that includes the needle head 3900 and the needle control sub-assembly 3902.

Figure 38:
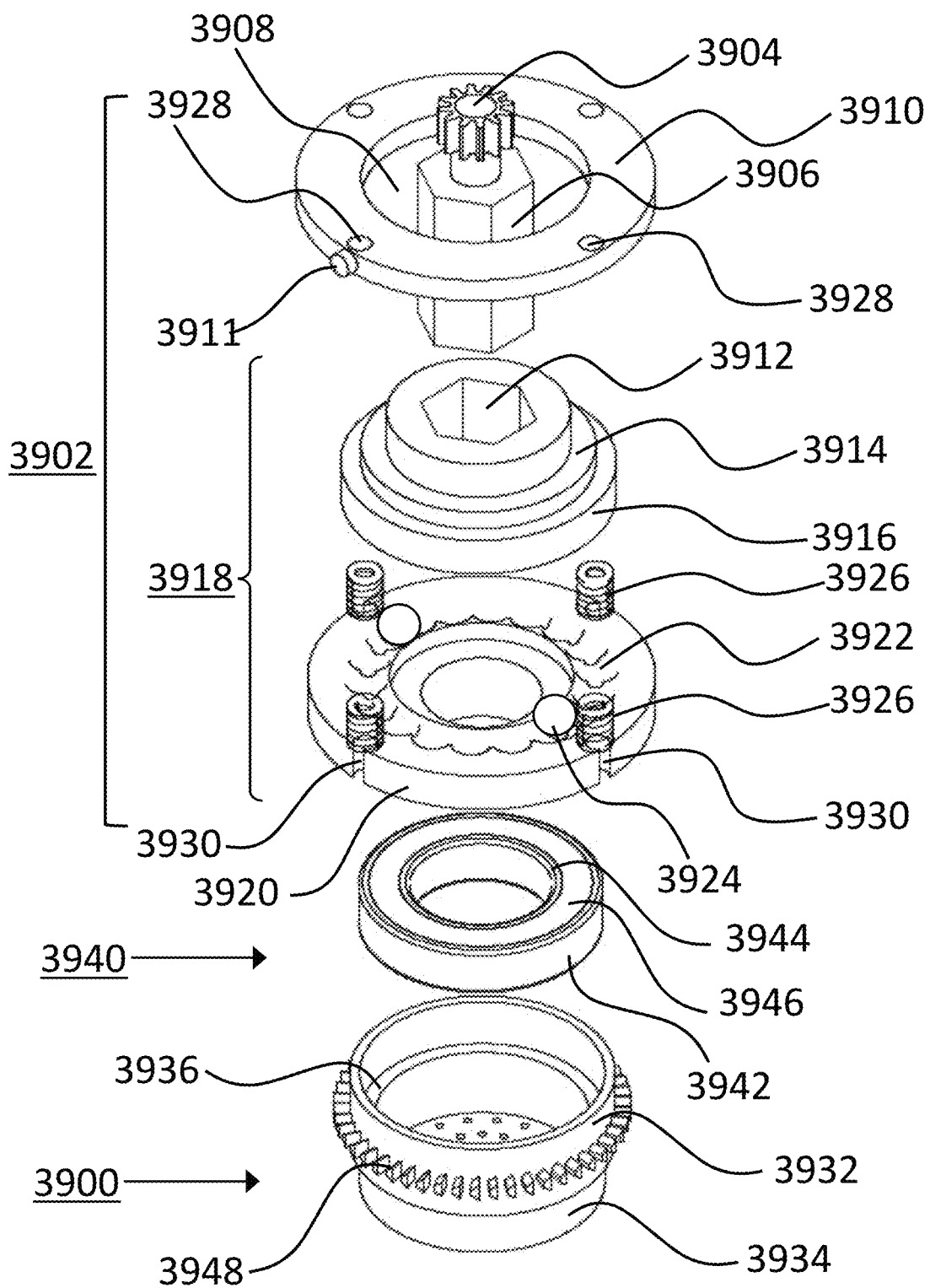
FIG. 38 is a simplified exploded view showing a needle control sub-assembly and a needle head configured to produce a movement of the needle head in a direction normal to an injection direction of the injector, according to another embodiment.

FIG. 38 is an exploded view showing an arrangement of the main components of the needle control sub-assembly 3902 and needle head 3900. A sun gear 3904, which is part of a planetary gear system of the auto-injector 100, is disposed at one end of a shaft 3906. The sun gear 3904 and shaft 3906 may be integrally formed using a molding process, or the sun gear 3904 and shaft 3906 may be separate parts that are assembled together. The sun gear 3904 does not rotate relative to the shaft 3906. In this example the shaft 3906 is generally hexagonal in a cross section taken within a plane that is normal to its length. Alternatively, the shaft 3906 may have a cross section that is generally triangular, square, rectangular, or pentagonal, etc., in shape. The shaft 3906 passes through a central opening 3908 in a follower plate 3910, which has a protrusion 3911 that performs the same function as the protrusion 240 as described above. A lower end of the shaft 3906 is received within a complementary shaped opening 3912 that is formed on an upper side 3914 of an upper plate 3916 of an oscillator element 3918. The oscillator element 3918 further comprises a lower plate 3920 having an upper grooved surface 3922, two spherical spacer elements 3924, and a plurality of extension springs 3926. When in the assembled condition, the two spherical spacer elements 3924 are seated within not illustrated openings formed in the bottom side of the upper plate 3916. The not illustrated openings are arranged 180° apart, such that the two spherical spacer elements 3924 are positioned symmetrically onto the upper grooved surface 3922 of the lower plate 3920. The two spherical spacer elements 3924 are e.g., metallic balls or plastic balls.

Figure 42:
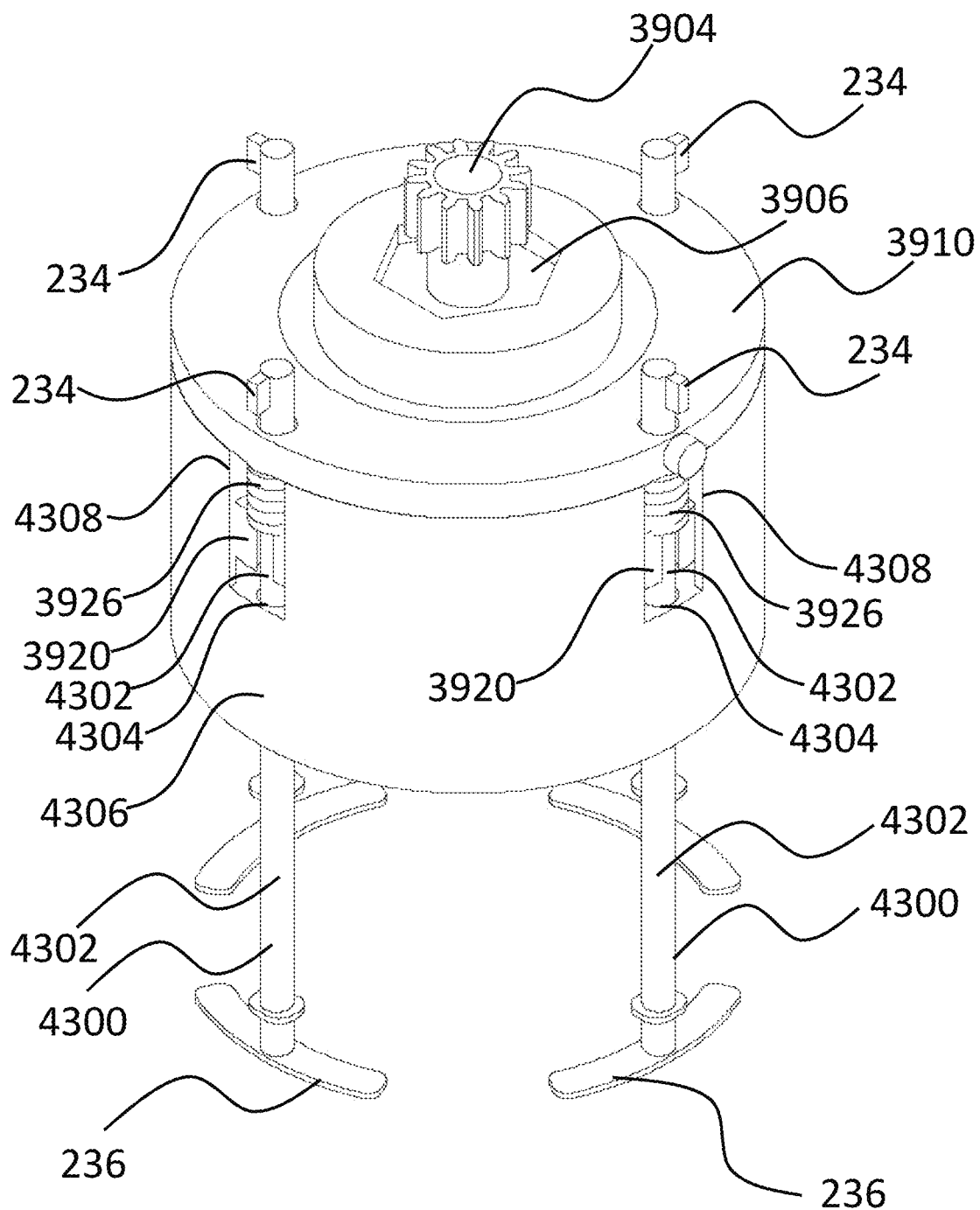
FIG. 42 is a simplified perspective view showing the needle control sub-assembly of FIG. 38 in an assembled condition.

Now referring also to FIG. 42, shown are the components of FIG. 38 in an assembled condition. FIG. 42 also shows a plurality of actuation legs 4300, which are part of a triggering mechanism of the auto-injector 100. Each actuation leg 4300 has a shaft portion 4302 that is configured to extend through one set of a plurality of sets of aligned openings. Each set of aligned openings includes a first opening 3928 formed through the follower plate 3910, a second opening 3930 formed through the lower plate 3920 of the oscillator element 3918, a third opening 4304 formed through a lower portion of the sidewall of a rotation drive housing 4306, as well the previously described openings 113 formed through the end surface 110 and the flange 114 of the outer housing 102. Also, as shown most clearly in FIG. 42, each shaft portion 4302 passes through one of the extension springs 3926, which are disposed between the bottom side of the upper plate 3916 and the upper grooved surface 3922 of the lower plate 3920.

The shaft portions 4302 prevent relative rotational movement between any of the above-mentioned elements. However, the upper plate 3916 has a diameter that is smaller than the respective diameters of the follower plate 3910 and of the lower plate 3920. Accordingly, the upper plate 3916 is accommodated within a space between the shaft portions 4302. Since the upper plate 3916 is rigidly coupled to the shaft 3906, and since the upper plate 3916 is too small to be rotationally constrained by the shaft portions 4302 of the actuation legs 4300, any rotational motion of the shaft 3906 causes corresponding rotational motion of the upper plate 3916 relative to the lower plate 3920 of the oscillator element 3918.

Referring now to FIG. 38 and FIG. 42, the diameter of the lower plate 3920 is also smaller than the diameter of the follower plate 3910, such that the second openings 3930 that are formed through the lower plate 3920 extend through the outer sidewall of the lower plate 3920, forming a plurality of circumferentially spaced-apart gaps in the outer sidewall thereof. The diameter of the lower plate 3920 is configured to permit the lower plate 3920 to be accommodated within the rotation drive housing 4306. As shown in FIG. 42, an upper portion of the sidewall of the rotation drive housing 4306 has a plurality of openings 4308 formed therethrough, which accommodate the shaft portions 4302 of the actuation lets 4300 and the extension springs 3926.

Referring again to FIG. 38, the needle head 3900 includes a first sidewall portion 3932 and a second sidewall portion 3934 of smaller diameter than the first sidewall portion 3932. An internal shoulder feature 3936 is formed between the first sidewall portion 3932 and the second sidewall portion 3934. A bearing element 3940 is disposed between the needle head 3900 and the lower plate 3920. In particular, the bearing element 3940 has an outer ring 3942 that is sized to be inserted within the first sidewall portion 3932 of the needle head 3900 and abut against the internal shoulder feature 3936. The bearing element 3940 also has an inner ring 3944 that is sized to receive a flanged protrusion (i.e., the flanged protrusion 4000 shown in FIG. 39) extending from the lower plate 3920. A rolling element assembly 3946, comprising a plurality of rolling elements (e.g., balls) and a retainer (e.g., ball separator) completes the bearing element 3940. The bearing element 3940 supports rotational movement of the needle head 3900 relative to the lower plate 3920 and other elements that are rotationally constrained by the shaft portions 4302 of the actuation legs 4300.

Figure 39:
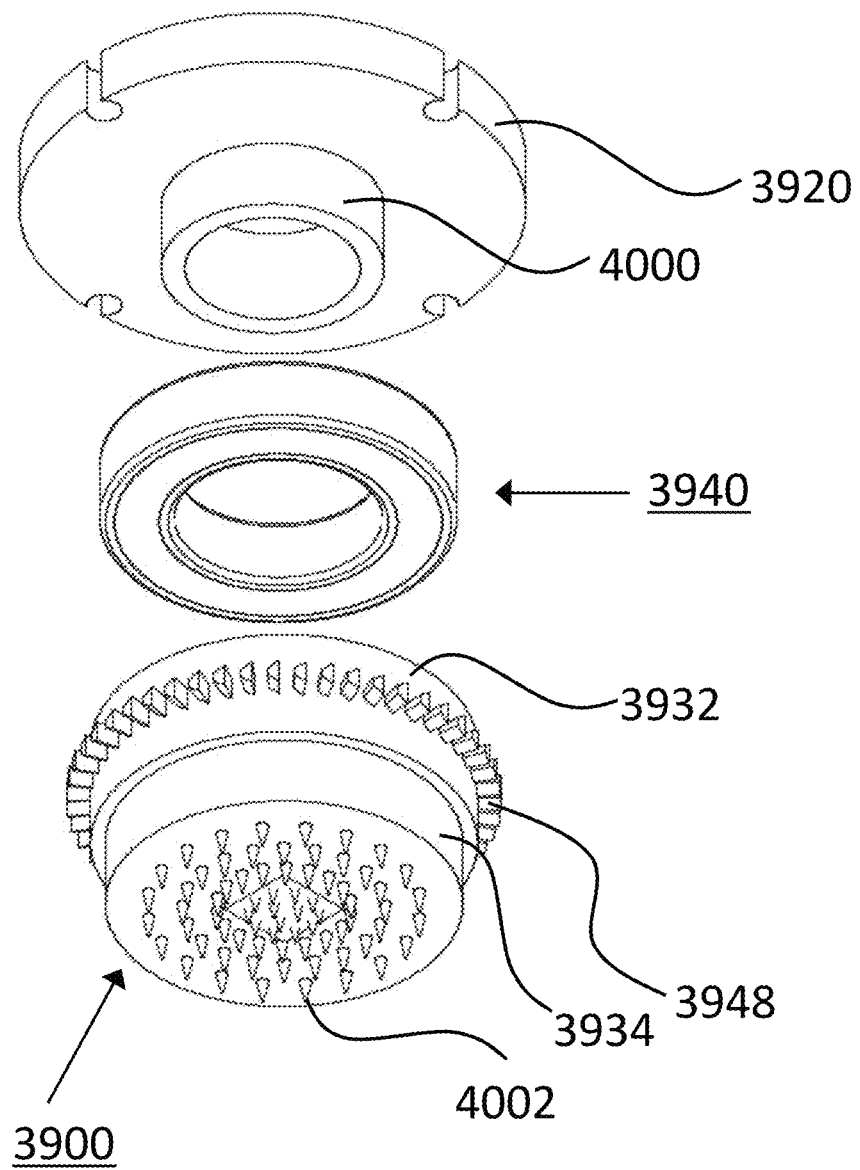
FIG. 39 is a simplified exploded view showing the arrangement of a bearing element between the needle control sub-assembly and needle head of FIG. 38.
Figure 40:
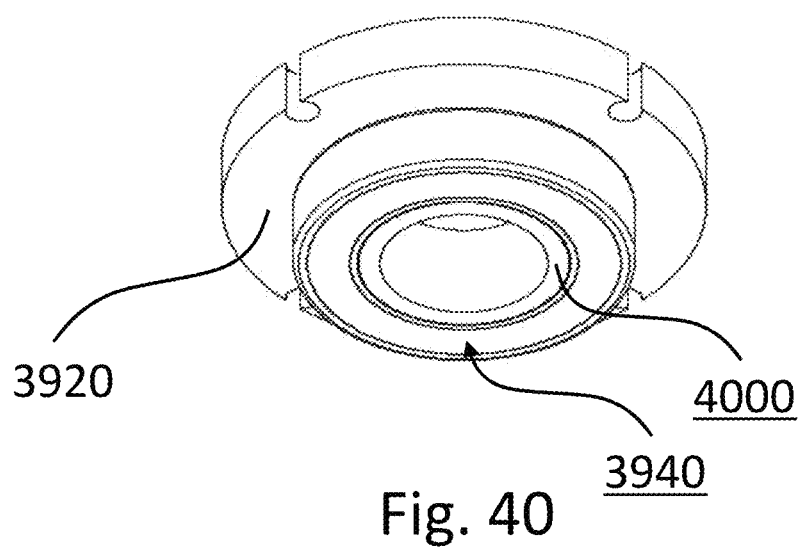
FIG. 40 is a simplified perspective view showing the position of the bearing element relative to the lower plate of the oscillator element of the needle control sub-assembly of FIG. 38 when the injector is in an assembled condition.
Figure 41:
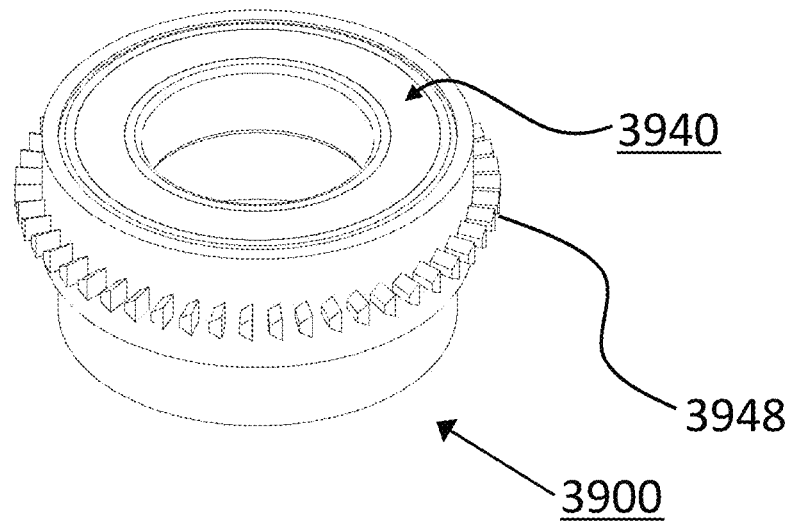
FIG. 41 is a simplified perspective view showing the position of the bearing element relative to the needle head of FIG. 38 when the injector is in an assembled condition.

FIG. 39 is an exploded perspective view showing the lower plate 3920, the bearing element 3940 and the needle head 3900 with needles 4002 in an unassembled but aligned condition. FIG. 40 shows the relationship between the bearing element 3900 and the circular flange 4000 in an assembled condition. FIG. 41 shows the relationship between the bearing element 3940 and the needle head 3900 in the assembled condition. The bearing element 3940 may be secured to the circular flange 4000 and the needle head 3900 by any suitable means, including by friction fit, adhesive, snap-fit, etc.

Figure 43A:
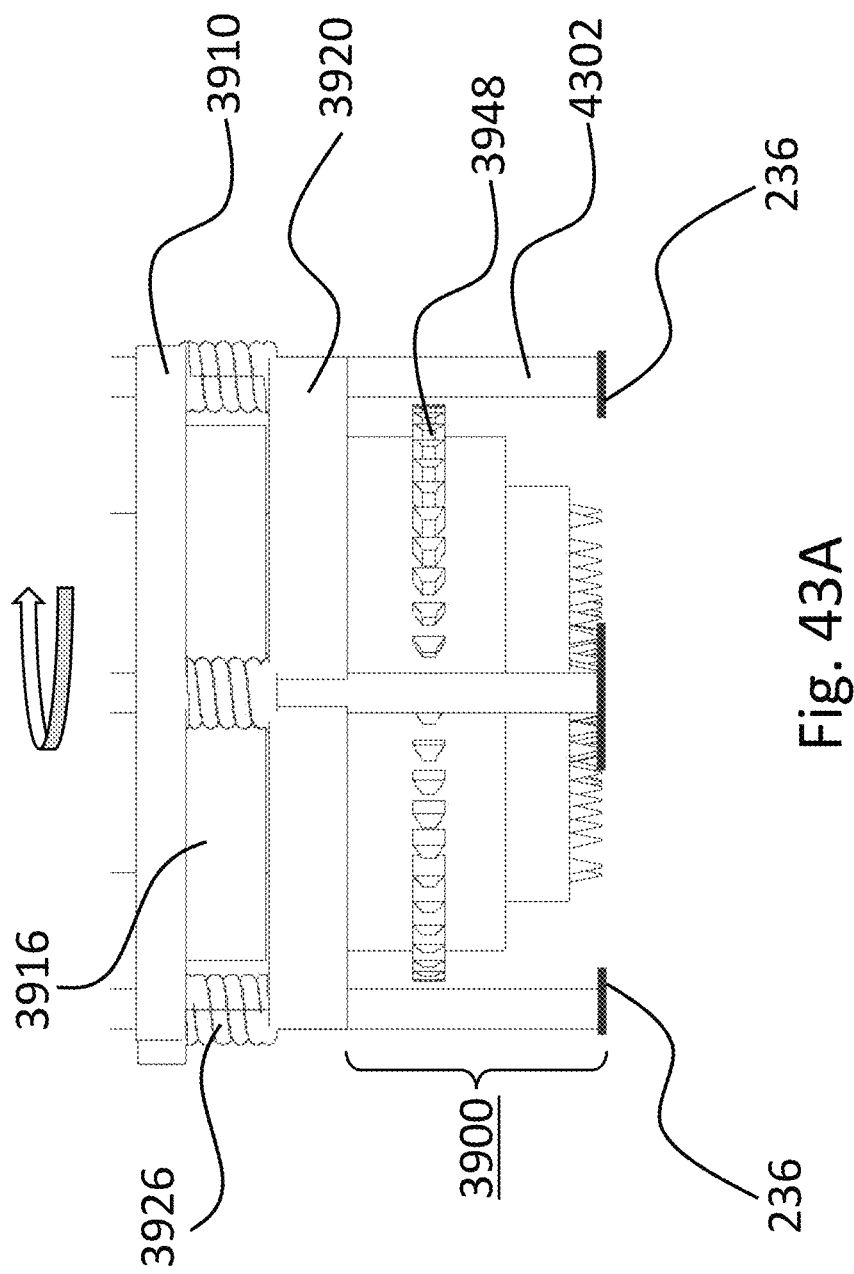
FIGS. 43A and 43B are simplified drawings that illustrate the oscillatory translational motion of the needle head of FIG. 38, with the rotation drive housing omitted improved for clarity.
Figure 43B:
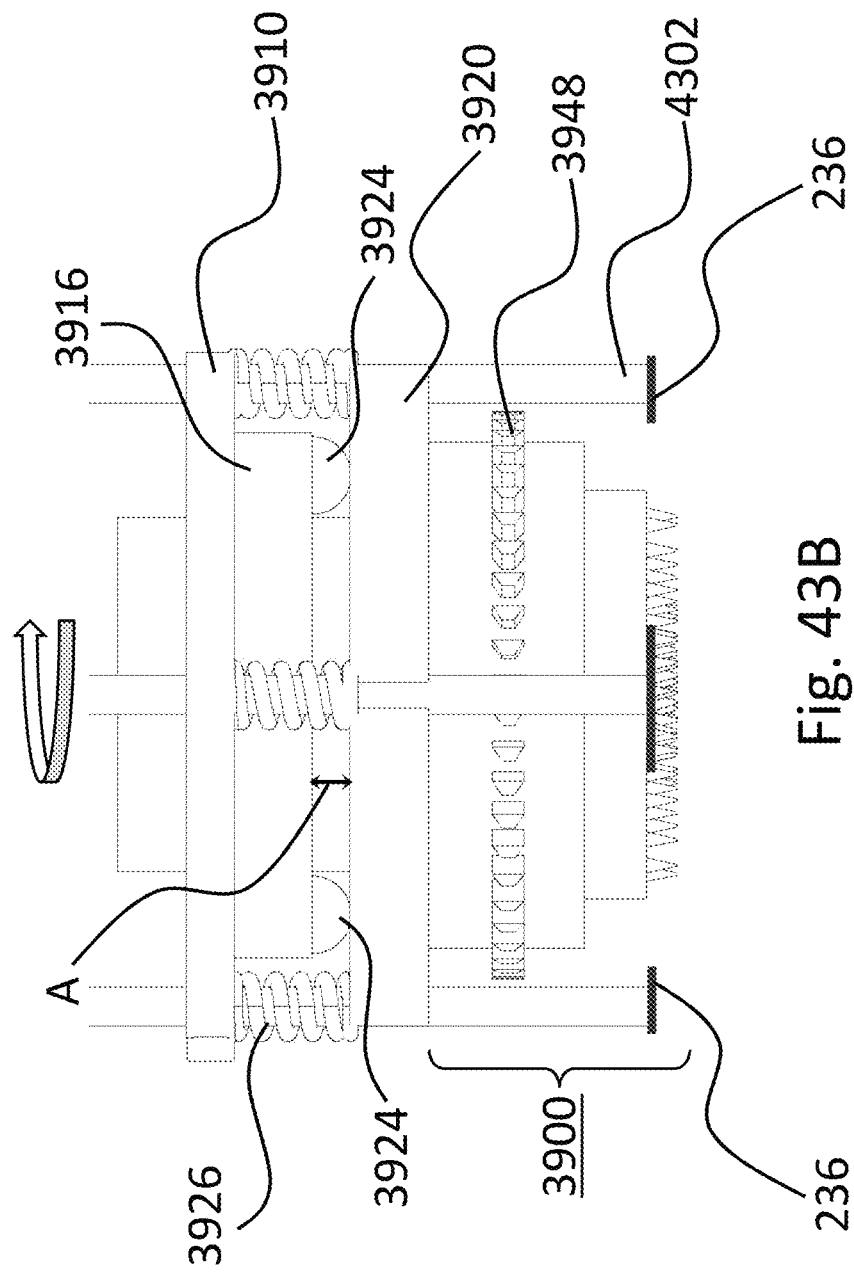

FIGS. 43A and 43B illustrate the oscillatory translation movement of the needle head 3900. During use the upper plate 3916 is caused to rotate relative to the lower plate 3920 in the direction indicated by the arrows in the drawings (i.e., clockwise in this example). As the upper plate 3916 rotates relative to the lower plate 3920, the two spherical spacer elements 3924 that are seated in the not illustrated openings in the bottom side of the upper plate 3916 are guided along a circular path around the grooved upper surface 3922 of the lower plate 3920, as they follow the upper plate 3916. As the two spherical spacer elements 3924 move along the circular path, they pass from one groove to the next along the upper grooved surface 3922 of the lower plate 3920. This motion may be visualized the as spherical spacer elements 3924 initially occupying a depression of one groove such that the upper plate 3916 and the lower plate 3920 are spaced very closely together as shown in FIG. 43A, then rolling up the side of the groove to a peak and forcing the upper plate 3916 and lower plate 3920 away from one another as shown in FIG. 43B, and then rolling back down the side of the next groove to occupy the depression of the next groove such that the upper plate 3916 and the lower plate 3920 are once again spaced very closely together as shown in FIG. 43A. The extension springs 3926 act to pull the upper plate 3916 and the lower plate 3920 back together after they have been forced apart by the spherical spacer elements 3924 passing over the peaks between respective pairs of adjacent depressions.

The structural configuration of the oscillator element 3918 converts the rotational motion of the shaft 3906 into an oscillating translational movement of the lower plate 3920 along the length direction of the auto-injector 100 relative to the upper plate 3916 (as indicated by the double headed arrow "A" in FIG. 43B). Since the upper plate 3916 is stationary relative to the outer housing 102, the result is that the needle array 3900 attached to the lower plate 3920 oscillates (relative to its fully extended position) in the length direction during an injection. The oscillation rate is dependent upon at least the number of peaks and depressions formed along the upper grooved surface 3922 of the lower plate 3920 and the rotational rate of the upper plate 3916.

Figure 44A:
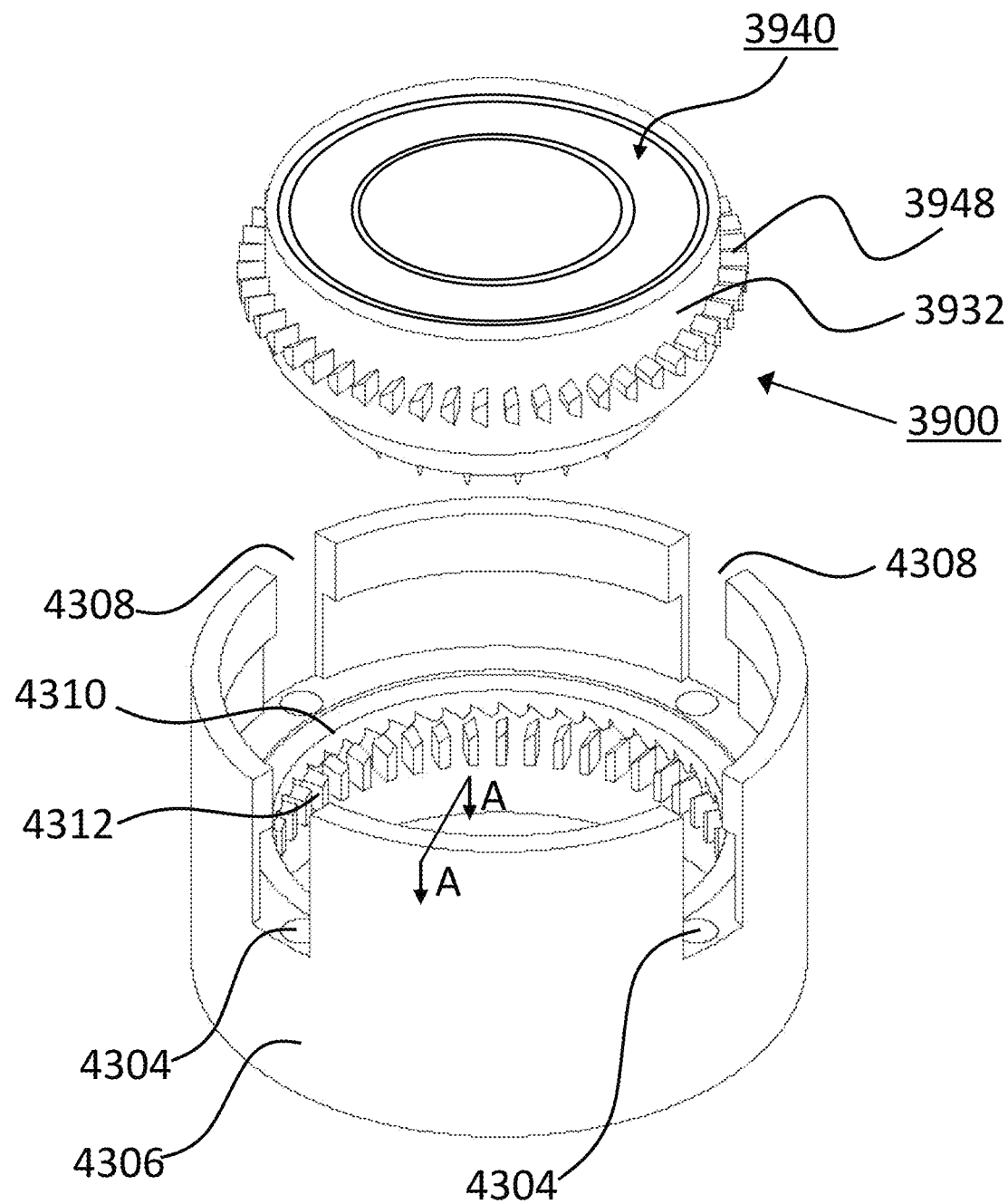
FIG. 44A is a perspective view showing the needle head separate from the rotation drive housing.
Figure 44B:
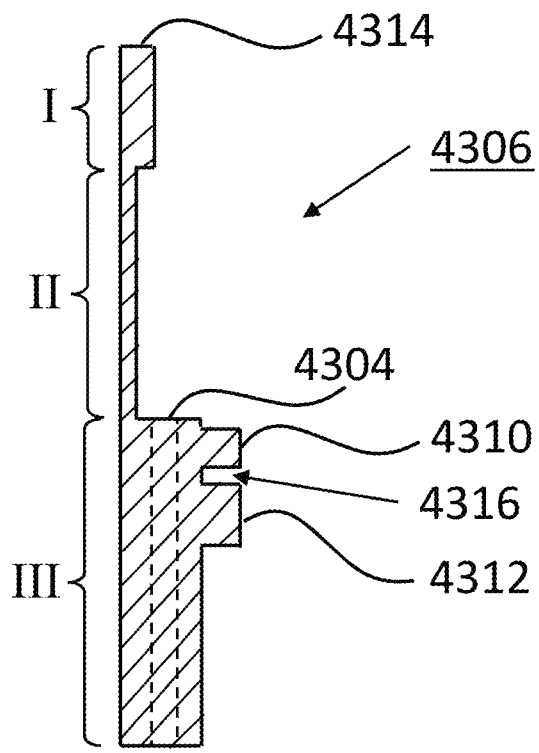
FIG. 44B is a cross-sectional view through the sidewall of the rotation drive housing.

FIG. 44A is a perspective view showing features of the needle array 3900 and features of the rotation drive housing 4306, which cooperate to induce a rotational movement of the needle array 3900 during the oscillating translational movement. FIG. 44B is a cross-sectional view through the sidewall of the rotation drive housing 4306 taken along line A-A in FIG. 44A. As is shown most clearly in FIG. 44A, the needle array 3900 includes a series of protrusions 3948 formed around the circumference of the first sidewall portion 3932. In addition, the rotation drive housing 4306 includes an inwardly extending ring of material 4310, which has a series of teeth formed along a lower edge thereof. The teeth along the lower edge of the ring of material 4310 are asymmetric. The rotation drive housing 4306 also has a series of inwardly extending protrusions 4312 extending around the inner surface thereof, which is disposed below the ring of material 4310 and is spaced-apart therefrom.

FIG. 44B shows, in a cross-sectional view, the ring of material 4310 and the inwardly extending protrusions 4312 arranged along a portion III of the inner surface of the rotation drive housing 4306. As will be apparent, the sidewall thickness of the rotation drive housing 4306 varies along the length direction. The third openings 4304, which receive the shaft portions 4302 of the actuation legs 4300, are formed within portion III. The sidewall is thinnest within portion II, which provides sufficient space to accommodate the lower plate 3920 of the oscillator element 3918. Portion I of the sidewall has a thickness intermediate that of portions II and III, which provides sufficient space to accommodate the upper plate plate 3916 of the oscillator element. As will be apparent from FIG. 42, the outside diameter of the rotation drive housing 4306 is substantially the same as the diameter of the follower plate 3910, which is disposed adjacent the top rim of the rotation drive housing 4306 in the assembled condition.

Figure 44C:
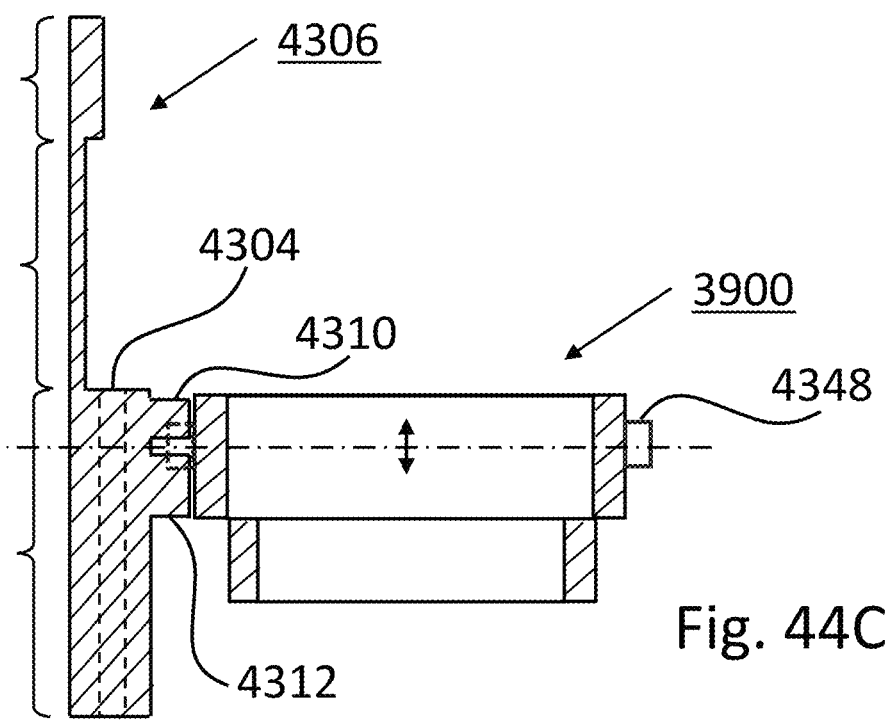
FIG. 44C is a cross-sectional view through the sidewall of the rotation housing with the needle head installed.

Now referring also to FIG. 44C, when in an assembled condition, the protrusions 3948 that are formed around the circumference of the first sidewall portion 3932 of the needle head 3900 are disposed within a circumferential space 4316 between the ring of material 4310 and the inwardly extending protrusions 4312. As is shown more clearly in FIGS. 45A-E, the protrusions 3948 move along the length direction "L" during the oscillatory movement of the needle head 3900. Rotational movement of the needle head 3900 is produced as a result of the interaction between the inclined upper and lower surfaces of the protrusions 3948, the inclined asymmetric lower surfaces of the ring of material 4310, the inclined upper surface of the protrusions 4312, and the offset between the inclined surfaces in the ring of material 4310 and the protrusions 4312.

Figure 45E:
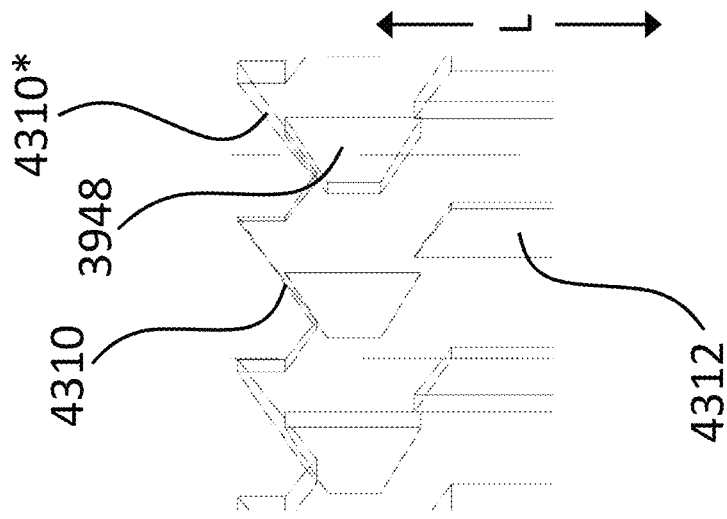
Figure 45D:
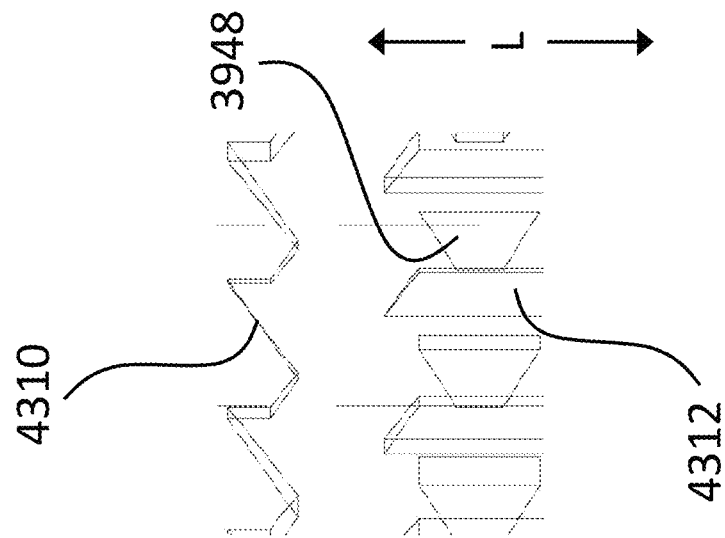

FIG. 45A shows the inclined upper surface of one of the protrusions 3948 abutting against a respective inclined leading surface of the ring of material 4310. This is the configuration that occurs when the upper plate 3916 and the lower plate 3920 of the oscillator element 3918 are spaced very closely together as shown in FIG. 43A. As the upper plate 3916 and the lower plate 3920 of the oscillator element 3918 begin to move away from one another toward the maximum extension of the oscillatory element "A" as shown in FIG. 43B, the lower inclined surface of the protrusion 3948 moves longitudinally toward the upper inclined surface of the protrusion 4312 and begins to slide there along, causing the protrusion 3948 to move to the right in FIG. 45B. The movement of the protrusion 3948 induces the rotational movement of the needle head 3900 as a whole. Referring now to FIG. 45C, as the oscillator element continues to force the upper plate 3916 and the lower plate 3920 of the oscillator element 3918 apart, the needle array 3900 continues to move in the length direction and the lower inclined surface of the protrusion 3948 continues to slide along the upper inclined surface of the protrusion 4312 causing the rotational motion of the needle head 3900 to continue until the protrusion 3948 moves past the end of the upper inclined surface of the protrusion 4312. At this point, as shown in FIG. 45D, the protrusion 3948 moves only in the longitudinal space between two adjacent protrusions 4312. When the oscillatory motion of the needle head 3900 reverses and the upper plate 3916 and the lower plate 3920 of the oscillator element 3918 move back toward one another, the upper inclined surface of the protrusion 3948 moves longitudinally toward the lower inclined surface of the ring of material 4310* and begins to slide there along, causing the protrusion 3948 to move to the right in FIG. 45E. The movement of the protrusion 3948 induces the rotational movement of the needle head 3900 as a whole.

One step of rotational motion of the needle head 3900, as described above, occurs during every oscillatory translational motion of the needle head 3900 along the injection direction. The rotational motion of the needle head 3900 causes the needles 300 extending therefrom, which may include hollow and/or solid needles, needles all having the same length or needles having different lengths, electrically conducting and/or electrically non-conducting needles, which may be arranged in any desired pattern to meet the requirements for a particular type of injection, etc., to undergo a curvilinear translational movement during the oscillatory translational motion. The curvilinear translational movement is along a direction that has a component normal to the injection direction.

Figure 45F:
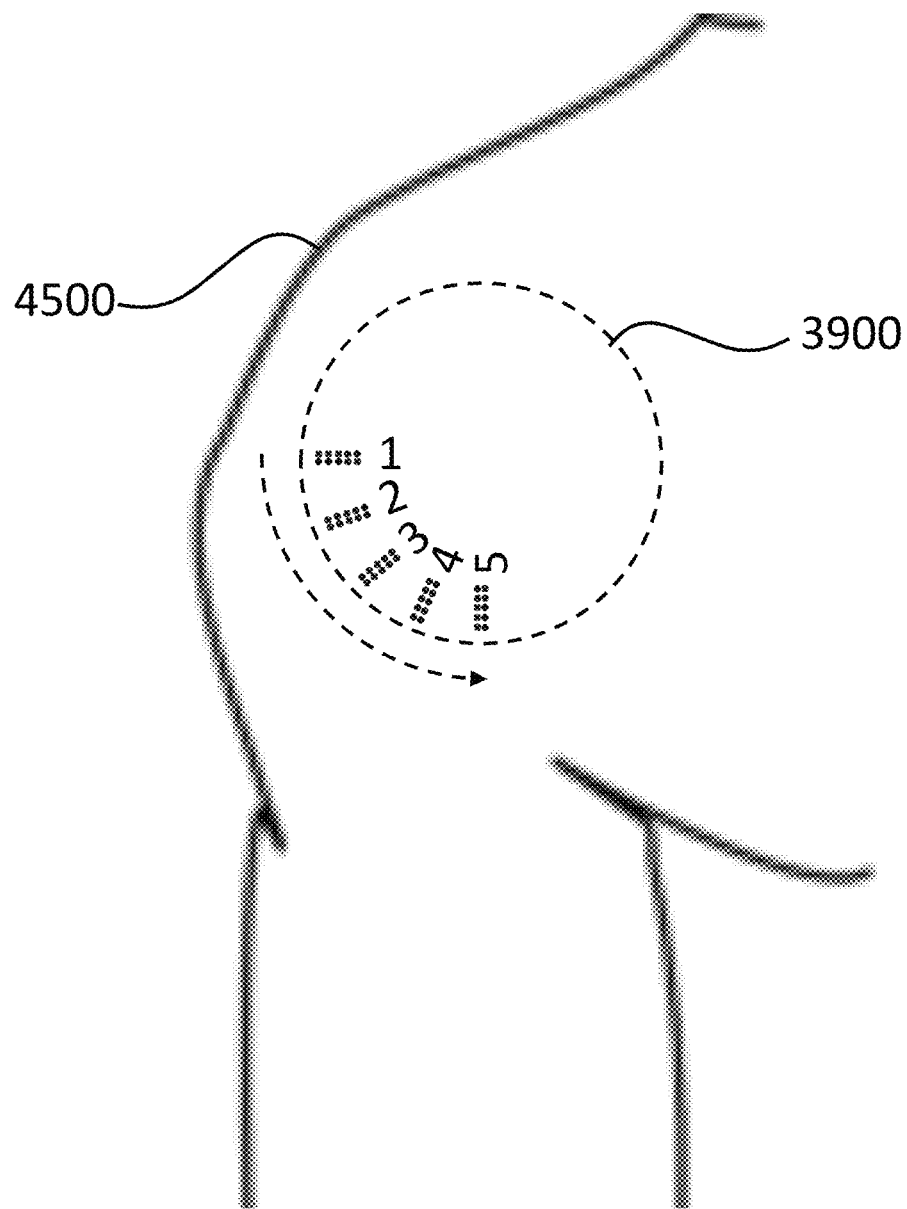
FIG. 45F is a simplified diagram showing a series five distinct puncture patterns in the skin of a subject's arm resulting from a curvilinear translational movement of a needle array during an injection.

FIG. 45F diagrammatically shows, on an enlarged scale, the effect of the curvilinear translational movement of the needles 300 as a result of the needle head 3900 rotating in the direction indicated by the dashed arrow, during an injection. In the specific example that is shown in FIG. 45F, the needles 300 are arranged in an array of two rows of six needles. A sequence of five oscillatory translational motions of the needle head 3900 along the injection direction produces five distinct puncture patterns (numbered 1, 2, 3, 4, 5 along the indicated direction of rotation of needle head 3900) in the skin of a subject's arm 4500. Each of the puncture patterns occurs within a different portion of the subject's skin. In practice, the number of distinct puncture patterns and/or the number of needles 300 in the array of needles may be different than is illustrated in FIG. 45F. The distinct puncture patterns may be more closely spaced together and may even partially overlap.

Alternative, the needles 300 may be caused to undergo a rectilinear translation movement using an injector that includes suitably configured mechanism. One possible example of such a suitably configured mechanism is shown, in relevant part, in FIGS. 45G-I. This alternative configuration is based on a modified version of the needle head 3900 and rotation drive housing 4306, but other suitable configurations may be envisaged. FIG. 45G is a top view of a linear drive housing 4502, which has features 4504 and 4506 that are analogous to the ring of material 4310 and the inwardly extending protrusions 4312, respectively, of the rotation drive housing 4306. These features are shown more clearly in the cross-sectional side view of FIG. 45I, but for simplicity the inclined surfaces of these features are not shown explicitly. It is to be understood that the surfaces of the features 4504 and 4506 are similar to the surfaces of the ring of material 4310 and the inwardly extending protrusions 4312 shown in FIGS. 45A-F. Referring now to FIG. 45H, shown is a top view of a needle head 4508 having outwardly extending protrusions 4410 that are functionally and structurally similar to the outwardly extending protrusions 3948 of needle head 3900.

Figure 45I:
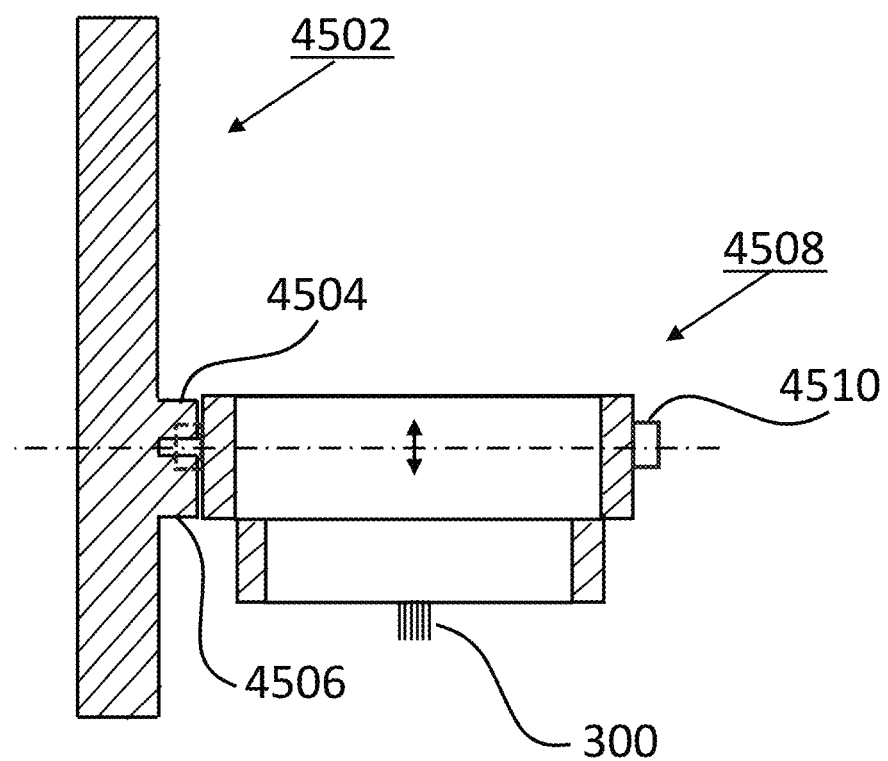
FIG. 45I is a longitudinal cross-sectional view showing the needle head of FIG. 45H installed within the linear drive housing of FIG. 45G.

FIG. 45I, which is a partial cross-sectional view, shows how the needle head 4508 is mounted within the linear drive housing 4502. The outwardly extending protrusions 4410 formed along opposite sides of the needle head 4508 are disposed within a respective space between the features 4504 and 4506 along sides of the linear drive housing 4502.

The mechanism shown in FIGS. 45G-I is essentially a straight version of the mechanism described above with reference to FIGS. 38-45E. During an injection, the needle head 4508 undergoes an oscillatory translational motion along an injection direction of the injector device. The needle head is caused to move along a direction that has a component normal to the injection direction as a result of interactions between (not illustrated) inclined upper and lower surfaces of the protrusions 4410, (not illustrated) inclined asymmetric lower surfaces of the feature 4504, (not illustrated) inclined upper surface of the features 4506, and (not illustrated) offset between the inclined surfaces in the ring of features 4504 and the protrusions 4506, as described with reference to FIGS. 45A-F but with the mechanism having a straight configuration instead of a cylindrical configuration.

Figure 45J:
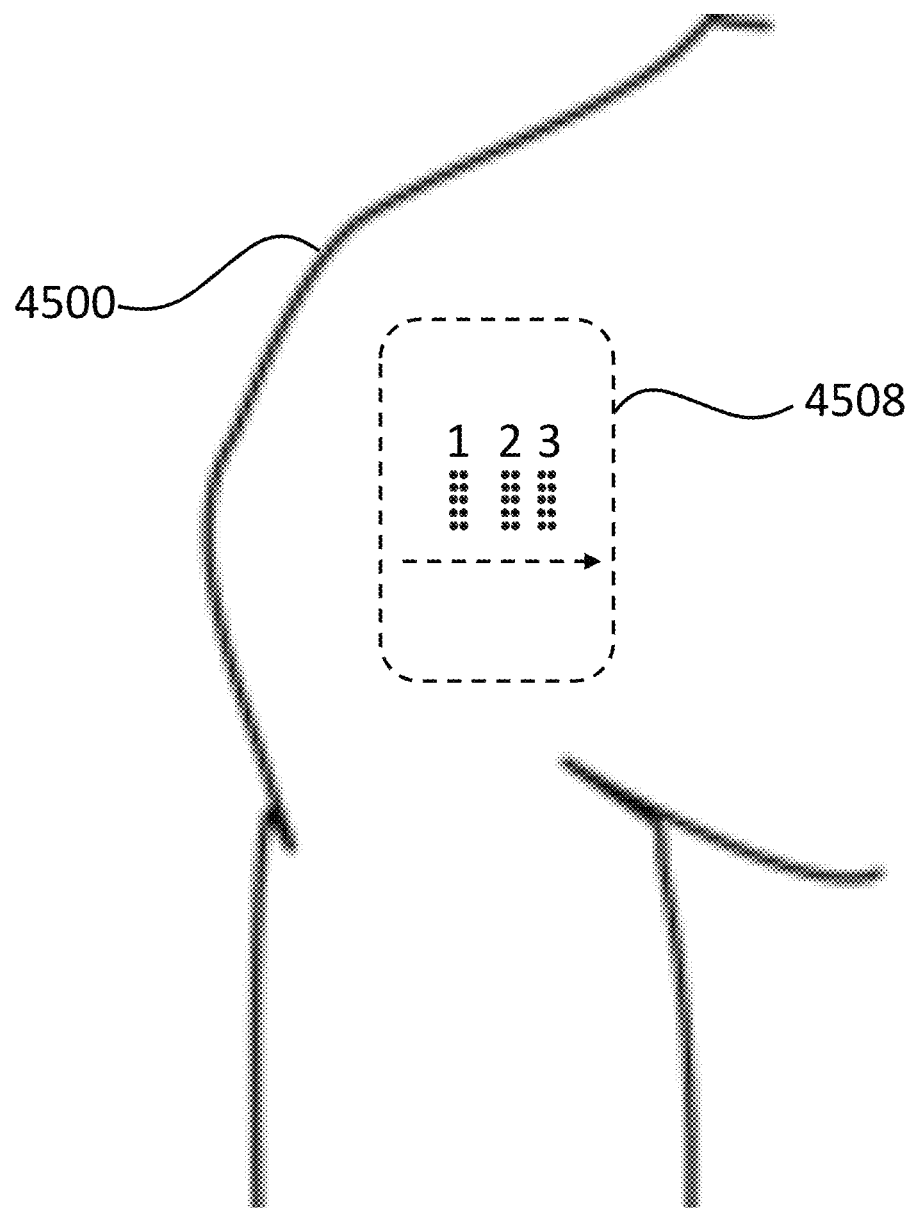
FIG. 45J is a simplified diagram showing a series three distinct puncture patterns in the skin of a subject's arm resulting from a rectilinear translational movement of a needle array during an injection.

FIG. 45J diagrammatically shows, on an enlarged scale, the effect of rectilinear translational movement of the needles 300 as a result of the needle head 4508 moving in the direction indicated by the dashed arrow, during an injection. In the specific example that is shown in FIG. 45J, the needles 300 are arranged in an array of two rows of six needles. A sequence of three oscillatory translational motions of the needle head 4508 along the injection direction produces three distinct puncture patterns (numbered 1, 2, 3 along the indicated direction of movement of needle head 4508) in the skin of a subject's arm 4500. Each of the puncture patterns occurs within a different portion of the subject's skin. In practice, the number of distinct puncture patterns and/or the number of needles 300 in the array of needles may be different than is illustrated in FIG. 45J. The distinct puncture patterns may be more closely spaced together and may even partially overlap.

It is to be understood that the motions indicated by the dashed arrows in FIGS. 45F and 45J occur whilst the injector is being held stationary relative to the skin 4500 of the subject. It is only the needle head that is moving with respect to the skin 4500 of the subject resulting in, e.g., a curvilinear translational motion of the needles 300 as shown in FIG. 45F or a rectilinear translational motion of the needles 300 as shown in FIG. 45J.

Causing the needles 300 to undergo some type of translational movement during the oscillatory translational motion provides several advantages, including injecting a full does of injectable substance in a series of rapid injections of partial doses, with at least a portion of each of the partial doses being injected into a fresh region of skin tissue rather than injecting multiple times into the same set of penetration holes. Since a larger area of the subject's skin becomes mechanically damaged when the needles undergo translational movement during the injection, the body is expected to mount a more robust immune response and thereby increase the effectiveness of the injection.

Figure 46:
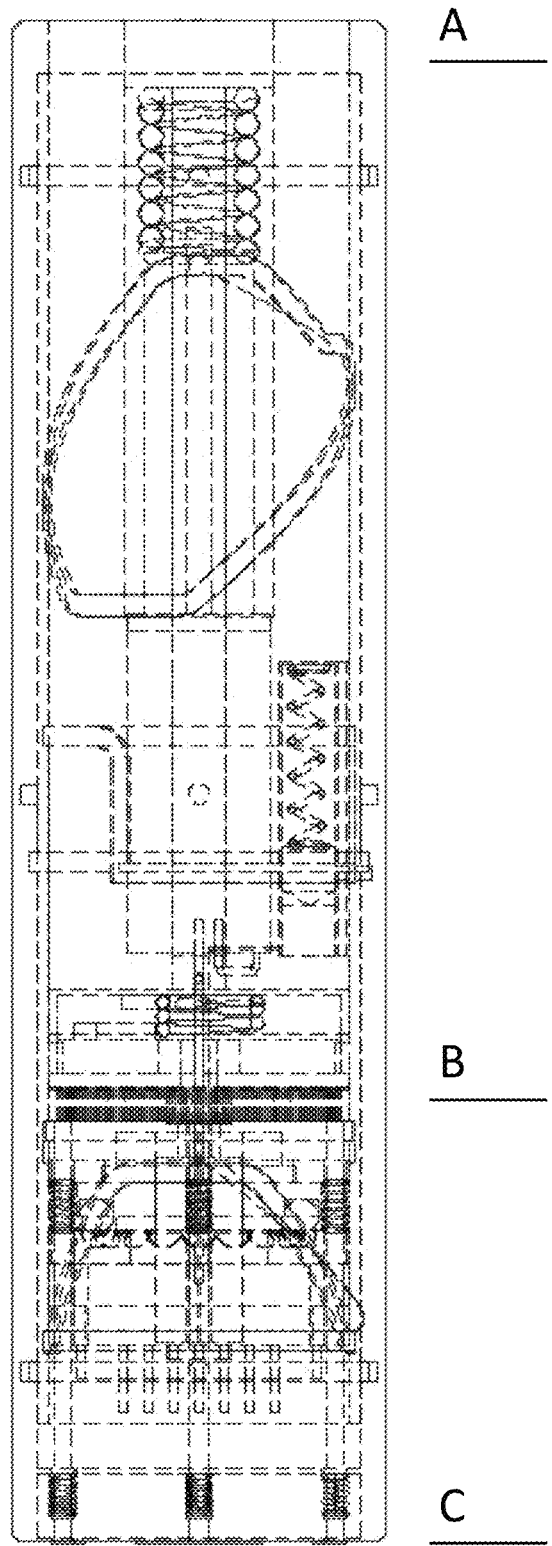
FIG. 46 is a simplified side view showing the second exemplary auto-injector device in a fully assembled condition.
Figure 47:
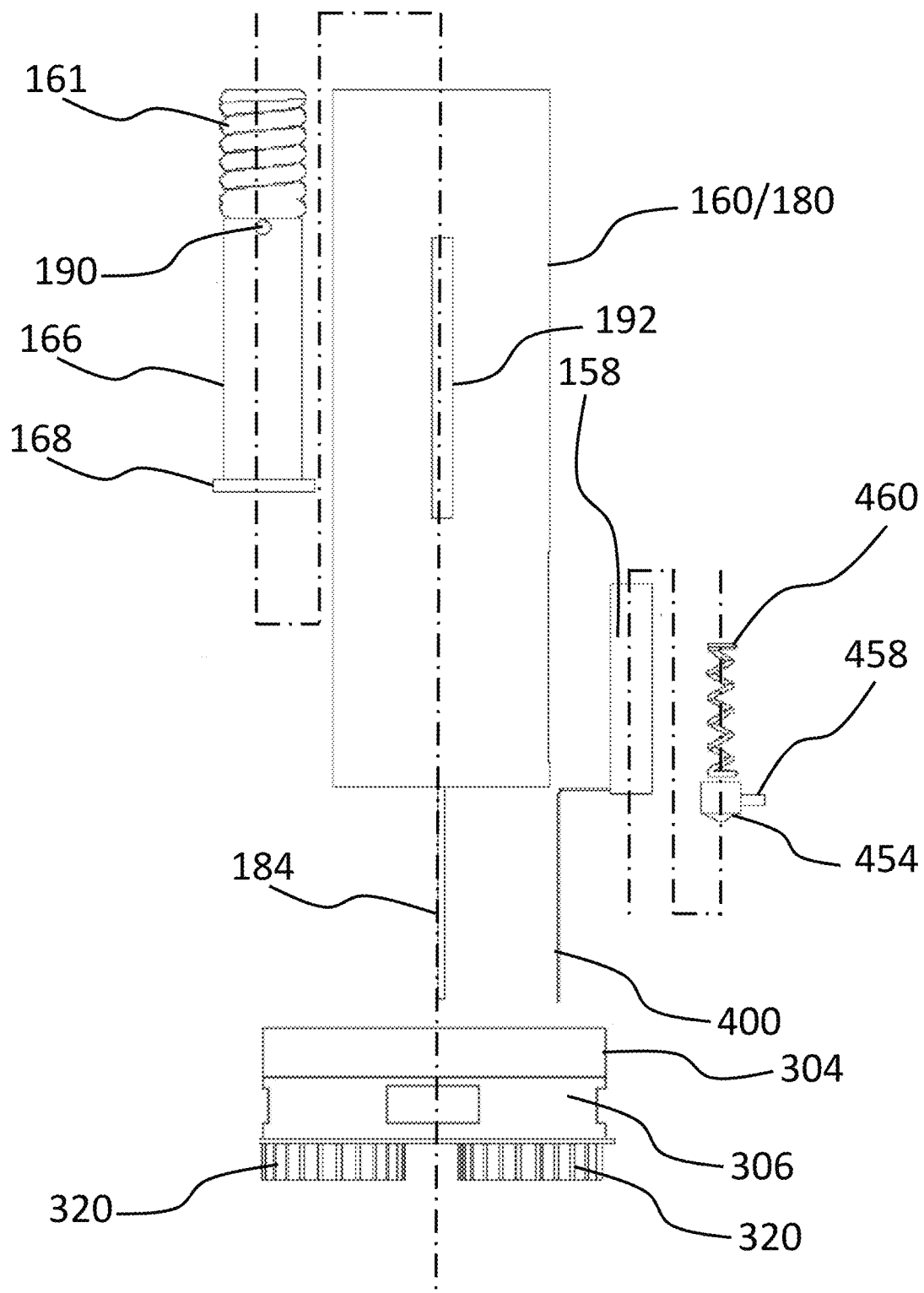
FIG. 47 shows, in isolation, the components of the second exemplary auto-injector within section A-B of FIG. 46, with the outer housing, control cylinder and various other housings omitted for improved clarity.
Figure 48:
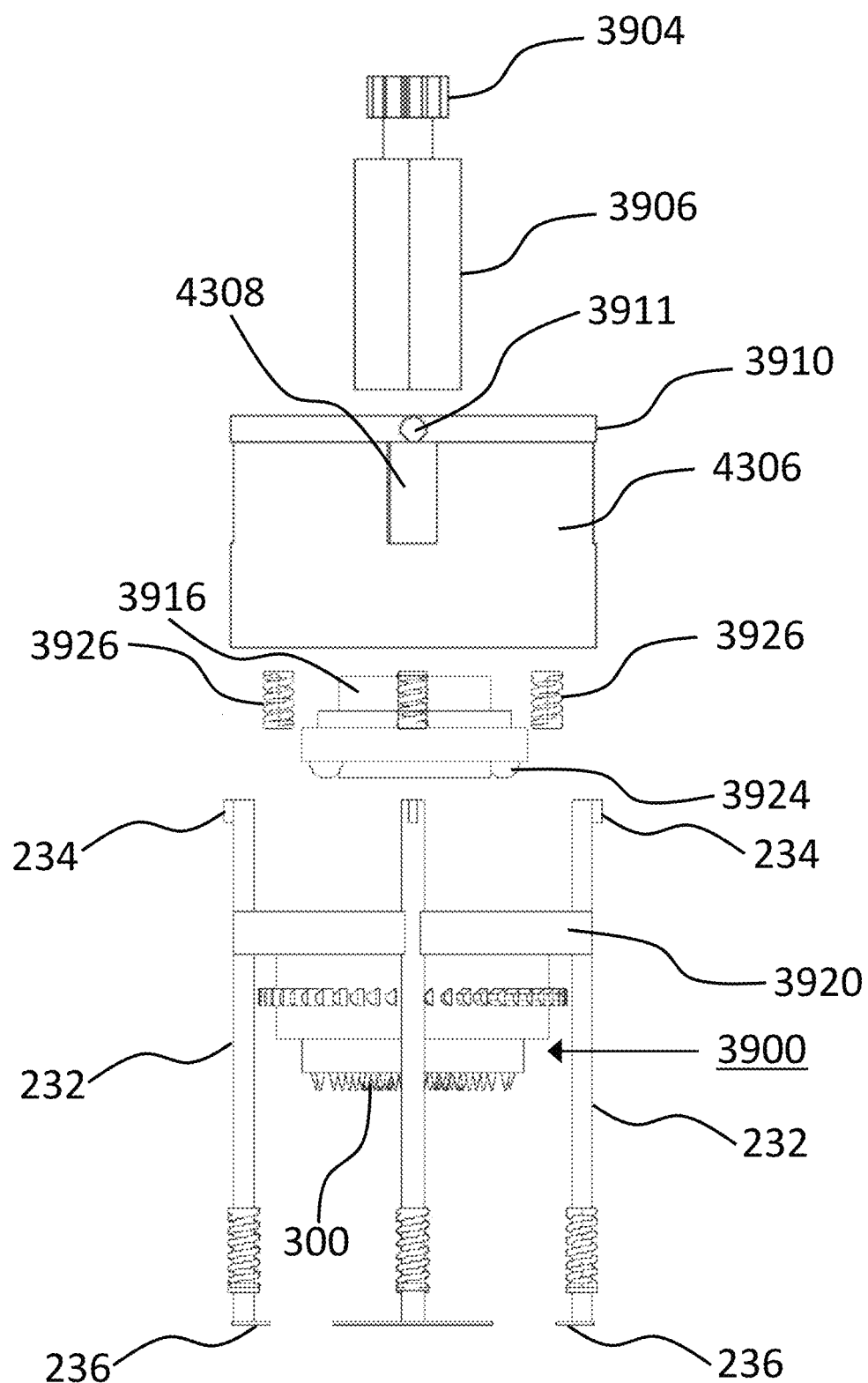
FIG. 48 shows, in isolation, the components of the second exemplary auto-injector within section B-C of FIG. 46, with the outer housing, control cylinder and various other housings omitted for improved clarity.

FIG. 46 is presented to show the second exemplary auto-injector in a fully assembled condition. Since the auto-injector comprises a nested arrangement of individual elements, there is a great deal of overlap in FIG. 33 which obscures the arrangement of the various elements. To facilitate a better understanding, regions denoted A-B and B-C have been indicated in FIG. 33. FIG. 34 shows the various elements in region A-B separated from one another, thereby avoiding overlap, such that each element can be seen more clearly. Similarly, FIG. 35 shows the various elements in region B-C separated from one another, thereby avoiding overlap, such that each element can be seen more clearly.

4. Method of Injecting

The auto-injector 100 described above is suitable for performing an injection of an injectable substance into the skin tissue of a mammalian subject, in particular, the injection may occur into a suitable injection site, such as for instance the epidermal tissue and/or the dermal tissue of the subject's skin as discussed in more detail in Section 3 above.

A method of providing an injection of an injectable substance to a mammalian subject may include all of the following, or only some of the following.

- An array of needles is extended from the outer housing 102 and penetrates the skin of the subject to a known depth.
- The array of needles is oscillated along a length direction of the device.
- The injectable substance is injected under pressure.
- An electrical current is sent to the skin to trigger electroporation.
- The array of needles is moved in a direction normal to the length of the device between oscillations.
- The array of needles retracts back into the outer housing 102 and causes suction effect.

The auto-injector 100 may be fully prepared for administering the injection prior to being shipped to the user that will be performing the injection. In particular, the auto-injector 100 may be provided in a ready-to-be-triggered condition with a vial 176 containing the desired injectable substance pre-loaded within the housing 180 of vial interface 156. Optionally, a protective end-cap or end-seal may be provided at the injectable end of the auto-injector 100.

As discussed above, the auto-injector 100 can be used to apply a transmembrane electric field pulse that induces microscopic pathways (pores) in a bio-membrane, allowing the delivery of one or more antigens from one side of the cellular membrane to the other (electroporation). The method can comprise the steps of administering the antigen to the cells of the epidermal tissues, contacting the epidermal tissues with electrodes within the needle array (i.e., hollow and/or solid metallic needles), and delivering an electroporating pulse to generate an immune response. The method can further comprise simultaneously delivering antigen to the cells and delivering an electroporating pulse to generate an immune response, either using the same needles or separate sets of needles of the needle array.

Figure 49:
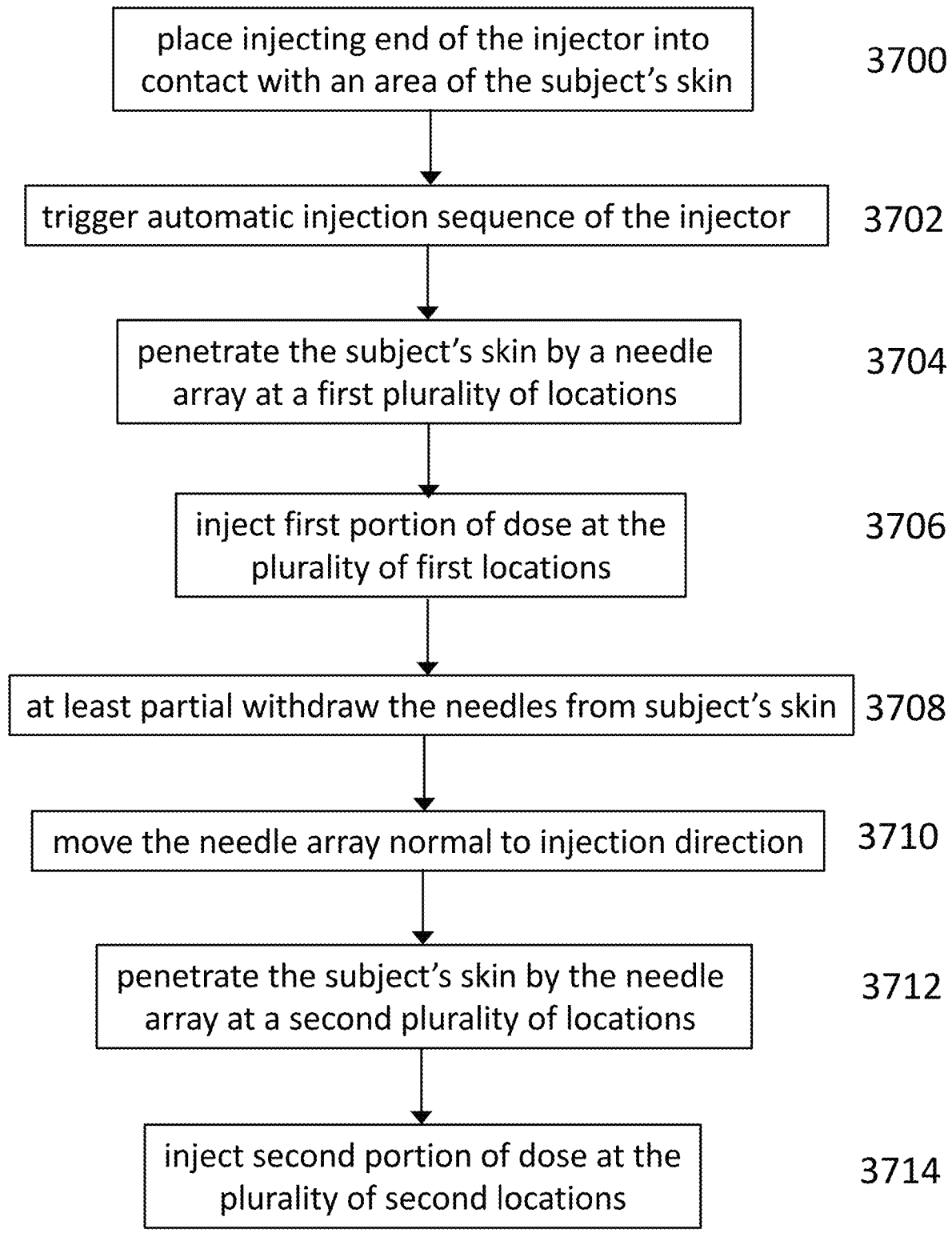
FIG. 49 is a simplified flow diagram of a method according to an embodiment.

Referring now to FIG. 49, shown is a simplified flow diagram of a method of injecting an injectable substance into the skin tissue of a mammalian subject. At step 3700, an injecting end of the injector (i.e., auto-injector 100) is placed into contact with an area of the subject's skin. The injector contains a single dose of the injectable substance having a dose volume. Optionally, a protective cap or seal (if present) is removed from the injecting end of the auto-injector 100 prior to being placed into contact with the subject's skin. In some embodiments, the protective cap may be saved and replaced prior to disposing of the auto-injector 100 after the injection. Optionally, the skin surface of the injection site is prepared, such as for instance by cleaning the skin surface with an alcohol wipe, etc., prior to placing the injecting end of the auto-injector into contact with the subject's skin. At step 3702, an automatic injection sequence of the auto-injector 100 is triggered. In the specific and non-limiting example described herein, triggering is performed by placing the feet 236 of the actuation legs 230 into contact with the subject's skin around the injection site and pressing downwardly so as to move the shafts 232 of the actuation legs 230 upwardly into the outer housing 100 and move the protrusions 234 out of their initial positions within respective notches 138 and into the trigger mechanism control slot 136. Once the auto-injector has been triggered, the injection occurs automatically in a timed sequence controlled by the control cylinder 120. The injection sequence includes the following steps. At step 3704 a needle array of the auto-injector 100, which comprises a plurality of needles, is moved along an injection direction and penetrates the subject's skin at a first plurality of locations. At step 3706 a first portion of the dose volume is injected into the subject's skin at the first plurality of locations. Optionally, an electric current is applied to the subject's skin to trigger electroporation during injecting the first portion of the dose. At step 3708 the plurality of needles is at least partially withdrawn from the subject's skin. At step 3710 the needle array comprising the plurality of needles is moved along a direction having a component that is normal to the injection direction. At step 3712 the needle array is moved along the injection direction and penetrates the subject's skin at a second plurality of locations. At step 3714 a second portion of the dose volume is injected into the subject's skin at the second plurality of locations. Because the needle array is moved along a direction having a component that is normal to the injection direction between penetrating the subject's skin at the first plurality of locations and at the second plurality of locations, at least some of the second plurality of locations are different from at least some of the first plurality of locations. As a result, the first portion of the dose and the second portion of the dose are injected into different areas of the subject's skin. After the injection sequence is completed, the user optionally replaces the protective cap (if present) and discards the auto-injector 100 according to prescribed procedure, such as for instance placing the auto-injector in a medical waste container.

4. Antigen

The present invention is also directed to methods of delivering at least one antigen using the MID 100, 200 having a plurality of electrode arrays 106, 108, as discussed above. The method can be directed to delivery of two or more antigens or a combination thereof using heterogeneous delivery by the MID 100, 200. In certain embodiments, the MID 100, 200 described herein can be used to enhance delivery of an antigen. As used herein, "antigen" refers to any substance or organism that provokes an immune response.

Throughout the description and claims of this specification, the words "comprise", "including", "having" and "contain" and variations of the words, for example "comprising" and "comprises" etc., mean "including but not limited to", and are not intended to, and do not exclude other components.

The terminology used herein is for the purpose of describing particular embodiments only and is not intended to be limiting. As used in the specification and the appended claims, the singular forms "a," "and" and "the" include plural references unless the context clearly dictates otherwise.

For the recitation of numeric ranges herein, each intervening number therebetween with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

It will be appreciated that variations to the foregoing embodiments of the disclosure can be made while still falling within the scope of the disclosure. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the disclosure are applicable to all aspects of the disclosure and may be used in any combination. Likewise, features described in non-essential combinations may be used separately (not in combination).

What is claimed is:

1. An injector for injecting an injectable substance into at least one of an epidermal tissue of a skin of a subject, a dermal tissue of the skin of the subject, a subcutaneous tissue of the subject, and a muscular tissue of the subject, the injector comprising:
    an outer housing;
    a control member disposed within the outer housing;
    a needle head configured to support a plurality of needles;
    first means in communication with the control member and configured to be driven by the control member for converting a movement of the control member into a movement of the needle head along an injection direction and toward an injecting position of the needle head;
    second means configured to move the needle head in a direction having a component that is normal to the injection direction and absent movement of the outer housing relative to the skin of the subject; and
    third means configured to produce an oscillatory movement of the needle head along the injection direction, the third means comprising a rotatable plate disposed in a stacked arrangement with a stationary plate, the stationary plate having a grooved surface facing the rotatable plate and defining a series of depressions and ridges, and further comprising a pair of spherical spacer elements retained within openings formed in the rotatable plate, and wherein each one of the pair of spherical spacer elements is guided over the ridges between respective adjacent pairs of depressions when the rotatable plate rotates such that a separation distance between the rotatable plate and the stationary plate varies in an oscillatory fashion over time to produce the oscillatory movement of the needle head along the injection direction.

2. The injector of claim 1, wherein the second means and the third means cooperate to move the needle head by one increment of motion in the direction having a component that is normal to the injection direction per oscillatory movement of the needle head along the injection direction.

3. The injector of claim 2, further comprising a plurality of needles supported by the needle head and forming a needle array having a predetermined arrangement, wherein the motion along the direction having a component that is normal to the injection direction induces one of a rectilinear translational motion of the needles of the needle array and a curvilinear translational motion of the needles of the needle array.

4. The injector of claim 1, comprising:
    a plurality of needles supported by the needle head and forming an array of needles having a predetermined arrangement;
    a plunger assembly including a plunger and a gas cylinder that contains a known volume of a gas prior to injecting the injectable substance; and
    an interface for receiving a container containing the injectable substance, the interface fluidly coupled to the gas cylinder via a first conduit, and the interface fluidly coupled to the array of needles via a second conduit, wherein the known volume of gas is equal to a combined volume of the first conduit, the second conduit, the container received within the interface, and a dead volume of the array of needles.

5. The injector of claim 4, wherein the interface comprises a housing that is keyed or shaped to receive only a correspondingly keyed or shaped container, and wherein the keying or shaping is specific to a known injectable substance or to a known set of injectable substances.

6. The injector of claim 1, comprising a plurality of needles supported by the needle head and forming an array of needles having a predetermined arrangement, wherein the plurality of needles comprises at least one hollow needle and at least one solid needle.

7. The injector of claim 6, wherein a length of some needles of the array of needles is different from a length of other needles of the array of needles.

8. The injector of claim 6, comprising an electric current source in electrical communication with at least some needles of the array of needles via a conductor, for providing an electroporation current to the at least one of the epidermal tissue and the dermal tissue of the subject during injecting the injectable substance, wherein said at least some needles are hollow needles or solid needles fabricated from an electrically conductive material.

9. The injector of claim 1, comprising a plurality of needles supported by the needle head and forming an array of needles having a predetermined arrangement, wherein the plurality of needles comprises at least one hollow needle and at least one solid needle and further comprising an electric current source in electrical communication with at least some of the plurality of needles via a conductor, for providing an electroporation current to the at least one of the epidermal tissue and the dermal tissue of the subject during injecting the injectable substance, wherein said at least some needles are hollow needles or solid needles fabricated from an electrically conductive material.

10. The injector of claim 1, wherein the needle head has a central cavity for receiving the injectable substance from a source of the injectable substance, and comprising a removable cap configured to sealingly mount to the needle head, the removable cap having through holes formed in an end surface thereof, each through hole in fluid communication with a hollow needle of a plurality of hollow needles forming a needle array, wherein during use the injectable substance is provided into the central cavity and is forced out through the through holes and into the needles by a fluid pressure to be injected into the at least one of the epidermal tissue and the dermal tissue of the subject.

11. The injector of claim 10, wherein the needle array further comprises at least one solid needle fabricated from an electrically conductive material.

12. An injector for injecting an injectable substance into at least one of an epidermal tissue of a skin of a subject, a dermal tissue of the skin of the subject, a subcutaneous tissue of the subject, and a muscular tissue of the subject, the injector comprising:
    an outer housing;
    a control member disposed within the outer housing;
    a needle head configured to support a plurality of needles forming a needle array;
    first means in communication with the control member and configured to be driven by the control member for converting a movement of the control member into a movement of the needle head along an injection direction and toward an injecting position of the needle head; and second means configured to move the needle head in a direction having a component that is normal to the injection direction and absent movement of the outer housing relative to the skin of the subject, wherein the second means comprises:
a plurality of first surfaces that are each inclined relative to the injection direction and are disposed at respective locations that are fixed relative to the outer housing; and
a plurality of second surfaces that are each inclined relative to the injection direction and that face toward a respective one of the plurality of first surfaces, the second surfaces disposed at respective locations that are fixed relative to the needle array,
wherein the second surfaces slide on the first surfaces when the needle array moves along the injecting direction, thereby causing the needle head to rotate about a rotation axis and producing one increment of movement of the needle head in the direction having a component that is normal to the injection direction.

13. An injector for injecting an injectable substance into at least one of an epidermal tissue of a skin of a subject, a dermal tissue of the skin of the subject, a subcutaneous tissue of the subject, and a muscular tissue of the subject, the injector comprising:

an outer housing;
a control member disposed within the outer housing;
a needle head configured to support a plurality of needles forming a needle array;
first means in communication with the control member and configured to be driven by the control member for converting a movement of the control member into a movement of the needle head along an injection direction and toward an injecting position of the needle head; and
second means configured to move the needle head in a direction having a component that is normal to the injection direction and absent movement of the outer housing relative to the skin of the subject,
wherein the control member is a rotatable control member comprising a control cylinder having a first control groove formed along an inner surface thereof and wherein the first means comprises a follower plate including a protrusion seated within the first control groove, wherein during rotational movement of the rotatable control member the protrusion is guided along the first control groove including a portion thereof having a component along the injection direction for converting the rotational movement of the rotatable control member into the movement of the needle array along the injection direction.

14. The injector of claim 13, comprising an energy source in communication with the first means for providing energy to rotate the rotatable control member.

15. The injector of claim 14, wherein the energy source comprises:
a torsion spring configured to store mechanical potential energy and to release the stored mechanical potential energy; and
a flywheel for converting the stored mechanical potential energy released from the torsion spring into stored rotational kinetic energy.

16. The injector of claim 14, wherein the energy source comprises:
an electric motor; and
a DC electrical power supply or an AC electrical power supply in electrical communication with the electric motor.

17. The injector of claim 7, comprising:
a plunger assembly including a plunger and a gas cylinder that contains a known volume of a gas prior to injecting the injectable substance;
an interface for receiving a container containing the injectable substance, the interface fluidly coupled to the gas cylinder via a first conduit, and the interface fluidly coupled to the plurality of needles of the needle array via a second conduit, wherein the known volume of gas is equal to a combined volume of the first conduit, the second conduit, the container received within the interface, and a dead volume of the needle array,
wherein the plurality of needles comprises at least one hollow needle and at least one solid needle, and further comprising:
an electric current source in electrical communication with at least some needles of the needle array via a conductor, for providing an electroporation current to the at least one of the epidermal tissue and the dermal tissue of the subject during injecting the injectable substance, wherein said at least some needles are hollow needles or solid needles fabricated from an electrically conductive material, and
wherein the control cylinder further includes a second control groove and a third control groove each formed along the inner surface of the control cylinder, wherein the second control groove is coupled to the plunger for controlling movement of the plunger and the third control groove is coupled to the electric current source for controlling actuation of the electric current source,
wherein shapes of the first, second and third control grooves are configured to control a translational movement of the needle head, the movement of the plunger, and the actuation of the electric current source in a pre-determined timed-sequence for injecting the injectable substance.

* * * * *